United States Patent
Gupta

(10) Patent No.: US 10,239,871 B2
(45) Date of Patent: Mar. 26, 2019

(54) COMPOUNDS AND METHODS FOR REGULATING INTEGRINS

(71) Applicant: ADHAERE PHARMACEUTICALS, INC., Skokie, IL (US)

(72) Inventor: Vineet Gupta, Glenview, IL (US)

(73) Assignee: ADHAERE PHARMACEUTICALS, INC., Skokie, IL (US)

(*) Notice: Subject to any disclaimer, the term of this patent is extended or adjusted under 35 U.S.C. 154(b) by 0 days.

(21) Appl. No.: 15/040,651

(22) Filed: Feb. 10, 2016

(65) Prior Publication Data
US 2016/0151336 A1 Jun. 2, 2016

Related U.S. Application Data

(60) Division of application No. 14/517,667, filed on Oct. 17, 2014, now Pat. No. 9,328,105, which is a
(Continued)

(51) Int. Cl.
*A61K 31/737* (2006.01)
*A61K 31/427* (2006.01)
(Continued)

(52) U.S. Cl.
CPC .......... *C07D 417/06* (2013.01); *A61K 31/337* (2013.01); *A61K 31/427* (2013.01);
(Continued)

(58) Field of Classification Search
None
See application file for complete search history.

(56) References Cited

U.S. PATENT DOCUMENTS 6,251,395 B1 6/2001 Gallatin et al.
7,718,680 B2 5/2010 Pellecchia et al.
(Continued)

FOREIGN PATENT DOCUMENTS

FR      2858324 A1   2/2005
WO   2000/010573 A1   3/2000
(Continued)

OTHER PUBLICATIONS

Tuttle. Linking metabolism and immunology: diabetic nephropathy is an inflammatory disease. J. Am. Soc. Nephrol. 16: 1537-1538. 2005.*
(Continued)

*Primary Examiner* — Anna Pagonakis
(74) *Attorney, Agent, or Firm* — Kilpatrick Townsend & Stockton LLP

(57) ABSTRACT

A method of treating inflammation, by administering an effective amount of a β2 integrin agonist to a patient, and reducing inflammation. A method of treating cancer, by administering an effective amount of a β2 integrin agonist to a patient, and reducing tumor growth. A method of treating a patient exposed to radiation, by administering an effective amount of a β2 integrin agonist to the patient after radiation exposure, and mitigating the effects of radiation exposure in the patient. A method of preventing effects of radiation, by administering an effective amount of a β2 integrin agonist to the patient prior to radiation exposure, and preventing the effects of radiation exposure on the patient. A method of treating acquired bone marrow failure (BMF), by administering an effective amount of a β2 integrin agonist to a patient. Methods of improving the health of damaged vasculature in a patient and activating β2 integrins.

6 Claims, 31 Drawing Sheets

Related U.S. Application Data continuation of application No. PCT/US2013/037548, filed on Apr. 22, 2013.

(60) Provisional application No. 61/791,523, filed on Mar. 15, 2013, provisional application No. 61/635,968, filed on Apr. 20, 2012.

(51) Int. Cl.
  *A61K 31/5377* (2006.01)
  *A61K 45/06* (2006.01)
  *C07D 417/06* (2006.01)
  *A61K 31/337* (2006.01)
  *A61N 5/10* (2006.01)
  *C07D 417/14* (2006.01)

(52) U.S. Cl.
  CPC .......... *A61K 31/5377* (2013.01); *A61K 45/06* (2013.01); *A61N 5/10* (2013.01); *C07D 417/14* (2013.01)

(56) References Cited

U.S. PATENT DOCUMENTS

| | | | |
|---|---|---|---|
| 9,023,876 B2* | 5/2015 | Gupta | C07D 417/06 514/369 |
| 9,328,105 B2 | 5/2016 | Gupta | |
| 2002/0052396 A1 | 5/2002 | Bailey et al. | |
| 2004/0002526 A1 | 1/2004 | Klein et al. | |
| 2004/0116468 A1 | 6/2004 | Nakagawa et al. | |
| 2005/0042213 A1* | 2/2005 | Gelder | A61K 31/075 424/94.64 |
| 2005/0227296 A1 | 10/2005 | Arnaout | |
| 2005/0282840 A1 | 12/2005 | Ross et al. | |
| 2006/0224234 A1 | 10/2006 | Jayaraman et al. | |
| 2006/0287319 A1 | 12/2006 | Jiang et al. | |
| 2007/0048216 A1 | 3/2007 | Norenberg et al. | |
| 2008/0033025 A1 | 2/2008 | Pellecchia et al. | |
| 2009/0069288 A1 | 3/2009 | Breinlinger et al. | |
| 2009/0130098 A1 | 5/2009 | Goodman et al. | |
| 2010/0055077 A1 | 3/2010 | Shakhov et al. | |
| 2010/0056503 A1 | 3/2010 | Gupta et al. | |
| 2010/0331315 A1 | 12/2010 | Haddach et al. | |
| 2012/0010255 A1 | 1/2012 | Gupta | |

FOREIGN PATENT DOCUMENTS

| | | |
|---|---|---|
| WO | 2004/093803 A2 | 11/2004 |
| WO | 2005/007118 A2 | 1/2005 |
| WO | 2005/016227 A2 | 2/2005 |
| WO | 2005/020990 A1 | 3/2005 |
| WO | 2005/041951 A2 | 5/2005 |
| WO | 2005/076695 A2 | 8/2005 |
| WO | 2006/024699 A1 | 3/2006 |
| WO | 2008/082537 | 7/2008 |
| WO | 2009/121031 A1 | 10/2009 |
| WO | 2010/118979 A1 | 10/2010 |
| WO | 2012/005800 A1 | 1/2012 |

OTHER PUBLICATIONS

Walzog et al. A role for beta2 integrins (CD11/CD18) in the regulation of cytokine gene expression of polymorphonuclear neutrophils during the inflammatory response. FASEB Journal, vol. 13, No. 13, pp. 1855-1865, Oct. 1999.*
Lim et al. Review article: Inflammation in diabetic nephropathy. Mediators of Inflammation. vol. 2012, Article ID 146154, 12 pages.*
Chow et al. Intercellular adhesion molecule-1 deficiency is protective against nephropathy in type 2 diabetic db/db mice. J. Am. Soc. Nephrol., 16: 1711-1722, 2005.*

Bjorklund et al., "Stabilization of the Activated $\alpha_M\beta_2$ Integrin by a Small Molecule Inhibits Leukocyte Migration and Recruitment," Biochemistry, 2006, vol. 45, pp. 2862-2871.
Carter et al., PNAS (2001), 98(21), pp. 11879-11884.
Celik et al., "Agonist Leukadherin-1 Increases CD11b/CD18-Dependent Adhesion Via Membran Tethers," Biophysical Journal, 2013, vol. 105, pp. 2517-2527.
Cheng et al., "Role of PPARα and Its Agonist in Renal Diseases," PPAR Research, Oct. 2010, vol. 2010, 6 pages.
Faridi et al., "Identification of novel agonists of the integrin CD11b/CD18," Bioorganic & Medicinal Chemistry Letters, 2009, vol. 19, pp. 6902-6906, DOI: 10.1016/j.bmcl.2009.10.077.
Faridi et al., "Small molecule agonists of integrin CD11b/CD18 do not induce global conformational changes and are significantly better than activating antibodies in reducing vascular injury," Biochimica et Biophysica Acta 1830 (2013) pp. 3696-3710.
Forino et al., PNAS (2005) 102(27):9499-9504.
Gill et al., JOC 2005, 70(26):10726-10731.
Jiang et al., "Design, synthesis, and biological activity of a novel series of 2,5-disubstituted furans/pyrroles as HIV-1 fusion inhibitors targeting gp41," Bioorganic & Medicinal Chemistry Letters, 2011, vol. 21, pp. 6895-6898.
Maiguel et al., "Small Molecule-Mediated Activation of the Integrin CD11b/CD18 Reduces Inflammatory Diseases," Science Signaling, 2011, vol. 4(189), ra57, DOI: 10.1126/scisignal.2001811.
Lee et al., Crystal Structure of the A domain from the alpha subunit of Integrin CR3 (CD11B/CD18), Cell, Feb. 1995; vol. 80, pp. 631-633.
Nathan et al., "Tumor necrosis factor and CE11/CD18 (beta2) integrins act syngeristically to lower cAMP in human neutrophils," J Cell Biology, 1990, vol. 111, pp. 2171-2181.
Park et al., "A Simple, No-Wash Cell Adhesion-Based High-Throughput Assay for the Discovery of Small-Molecule Regulators of the Integrin CD11b/CD18," Journal of Biomolecular Screening, 2007, vol. 12, pp. 406, DOI: 10.1177/1087057106299162.
Reed et al., "Complement Receptor 3 Influences Toll-like Receptor 7/8-Dependent Inflammation," Journal of Biological Chemistry, 2013, vol. 288(13), pp. 9077-9083.
Reyes et al., J. Biomed Mater Res, 2003, vol. 67A, pp. 3288-3333.
Shah, "Inflammation, Neointimal Hyperplasia, and Restenosis: As the Leukocytes Roll, the Arteries Thicken," Circulation, 2003, vol. 107(17), pp. 2175-2177, DOI: 10.1161/01.cir.0000069943.41206.bd.
Simon et al., "Opening the Field of Integrin Biology to Biased Agonism," Circulation Research, 2011, vol. 109, pp. 1199-1201.
Tautz et al., J. Biological Chemistry, 2005, 280(10):9400-9408.
Verma et al., Molecular Pharmaceuticals, 2008, 5(5):745-759.
Xiong et al., The J. of Immunology, 2003, vol. 171, pp. 1042-1050.
Chemical Abstracts RN 344897-95-6; entered STN Jul. 8, 2001, 1 page.
ChemBridge Catalog # 5679982 4-{5-[(Z)-(3-Benzyl-4-oxo-2-thioxo-1,3-thiazolidin-5-ylidene)methyl]-2-furyl}benzoic acid, http//:www.hit2lead.com/result.asp?search=14662037, retrieved on Jan. 7, 2014.
ChemBridge Catalog # 6789780 Ethyl [(5Z)-5-{[5-(2,4-dichlorophenyl)-2-furyl]methylene}-2,4-dioxo-1,3-thiazolidin-3-yl]acetate, http//:www.hit2lead.com/result.asp?search=13199976, retrieved on Jan. 8, 2014.
ChemBridge Catalog # 6528335 2-Chloro-5-(5-{(Z)[3-(4-fluorobenzyl)-2,4-dioxo-1,3-thiazolidin-5-ylidene]methyl}-2-furyl)benzoic acid, http//:www.hit2lead.com/result.asp?search=30881677, retrieved on Jan. 8, 2014.
ChemBridge Catalog # 6725132 Ethyl {(5Z)-2,4-dioxo-5-[(5-phenyl-2-furyl)methylene]-1,3-thiazolidin-3-yl}acetate, http//:www.hit2lead.com/result.asp?search=85021953, retrieved on Jan. 8, 2014.
ChemBridge Catalog #: 7476685 (5Z)-3-(2-Furylmethyl)-5-[(5-phenyl-2-furyl)methylene]-2-thioxo-1,3-thiazolidin-4-one, http//:www.hit2lead.com/result.asp?search=17650479, retrieved on Jan. 8, 2014.
EP Application No. 11 80 3961, Supplementary European Search Report, Date of completion Oct. 16, 2013, 1 page.
PCT Application No. PCT/US2011/034753, International Search Report, dated Oct. 3, 2011, 3 pages.
PCT Application No. PCT/US2013/037548, International Search Report, dated Aug. 20, 2013, 1 page.

(56) References Cited

OTHER PUBLICATIONS

Hudkins et al. "BTBR Ob/Ob Mutant Mice Model Progressive Diabetic Nephropathy," *J Am Soc Nephrol.*, Jul. 15, 2010, vol. 21, pp. 1533-1542.

\* cited by examiner

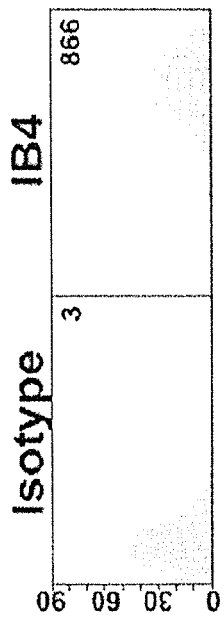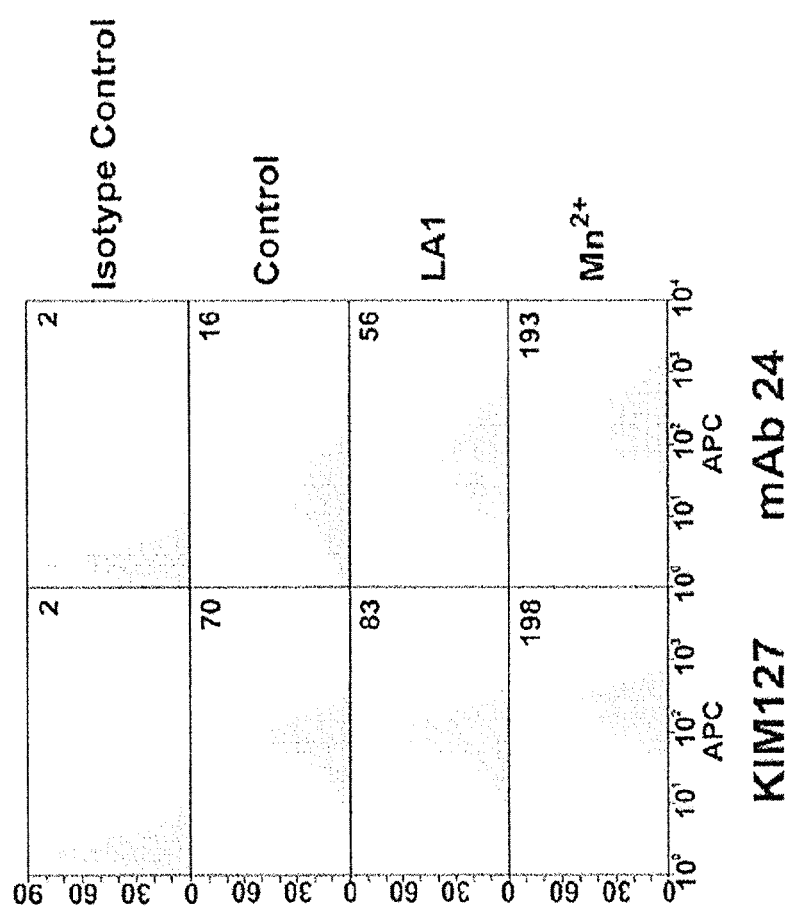
Fig. 7A
Fig. 7B

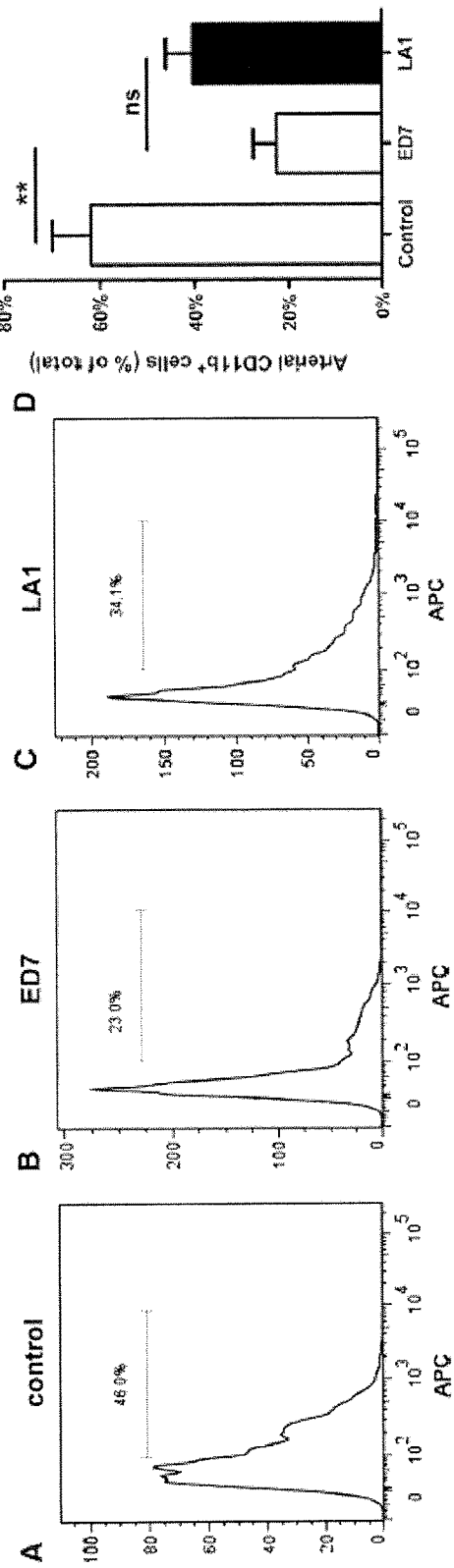

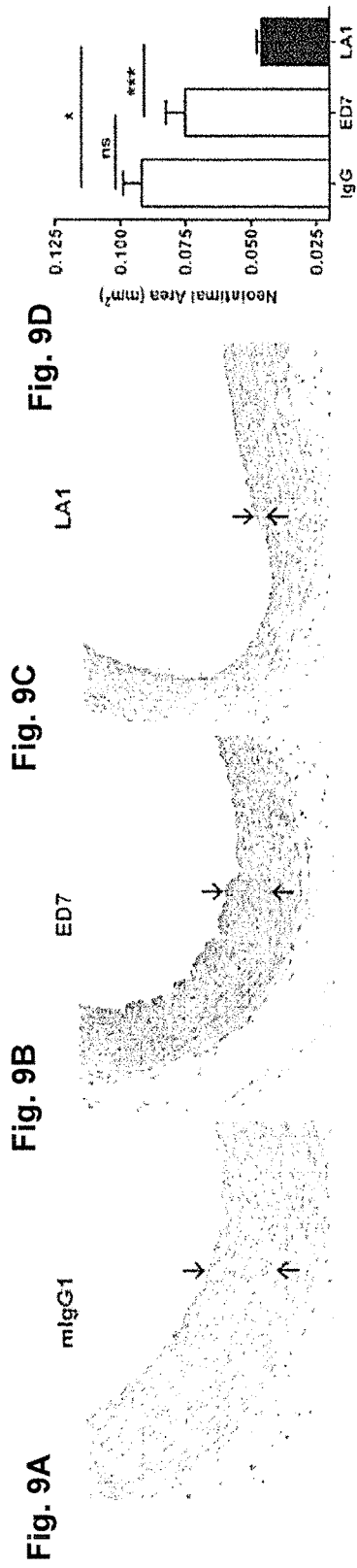

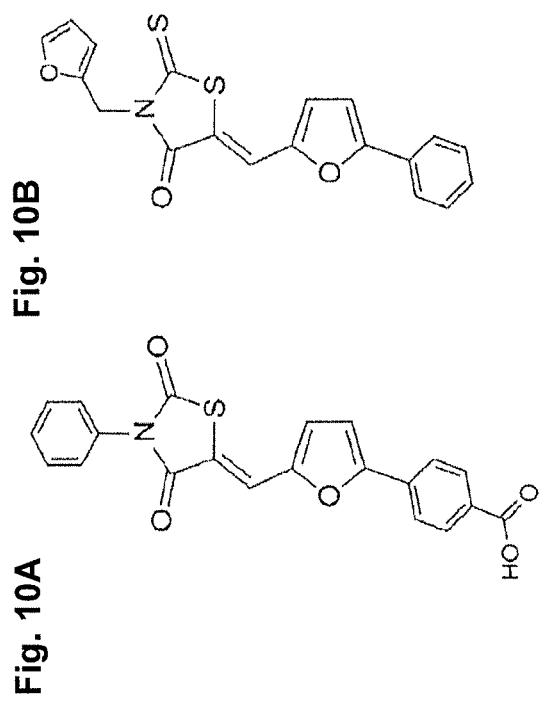

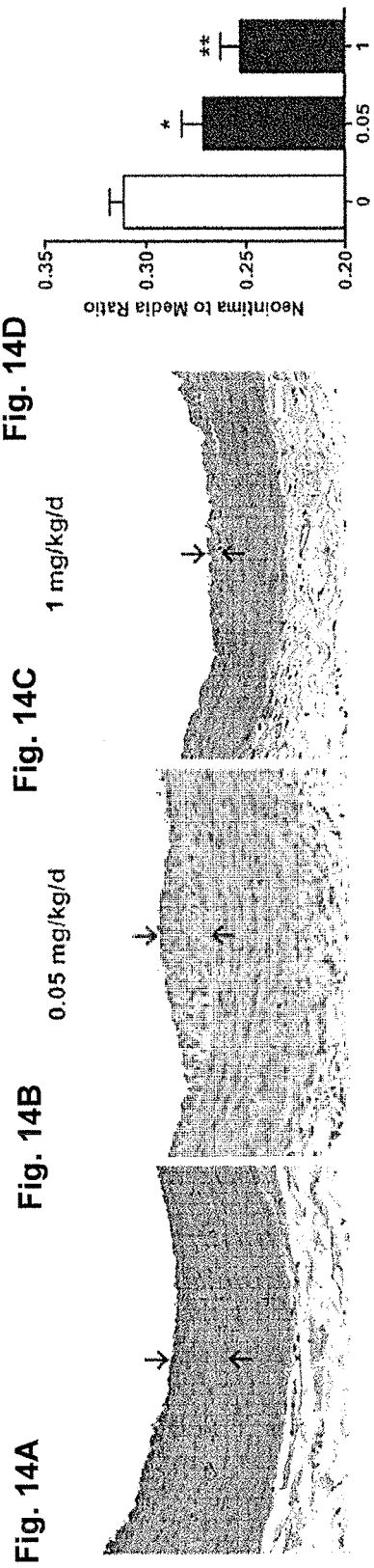

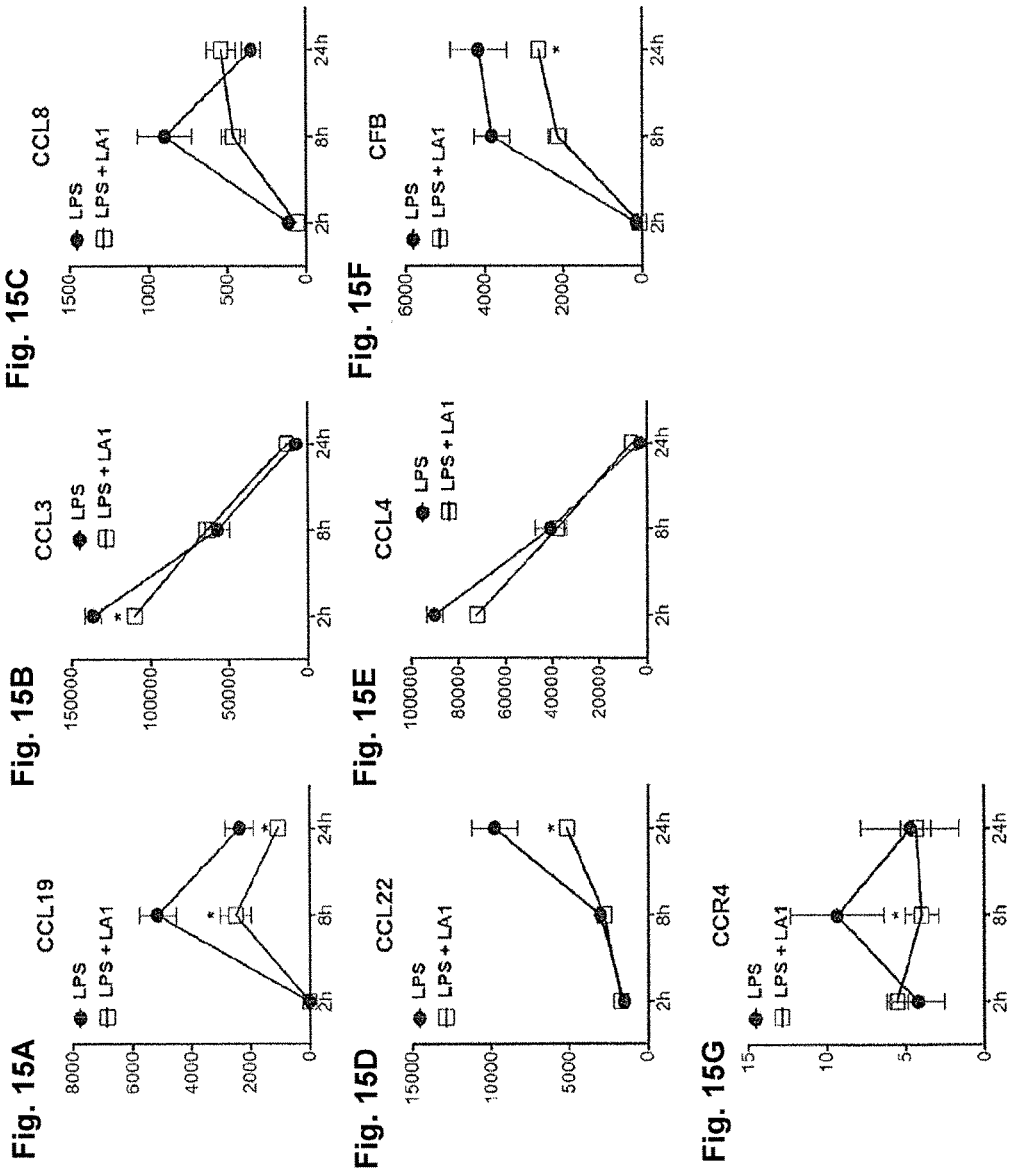

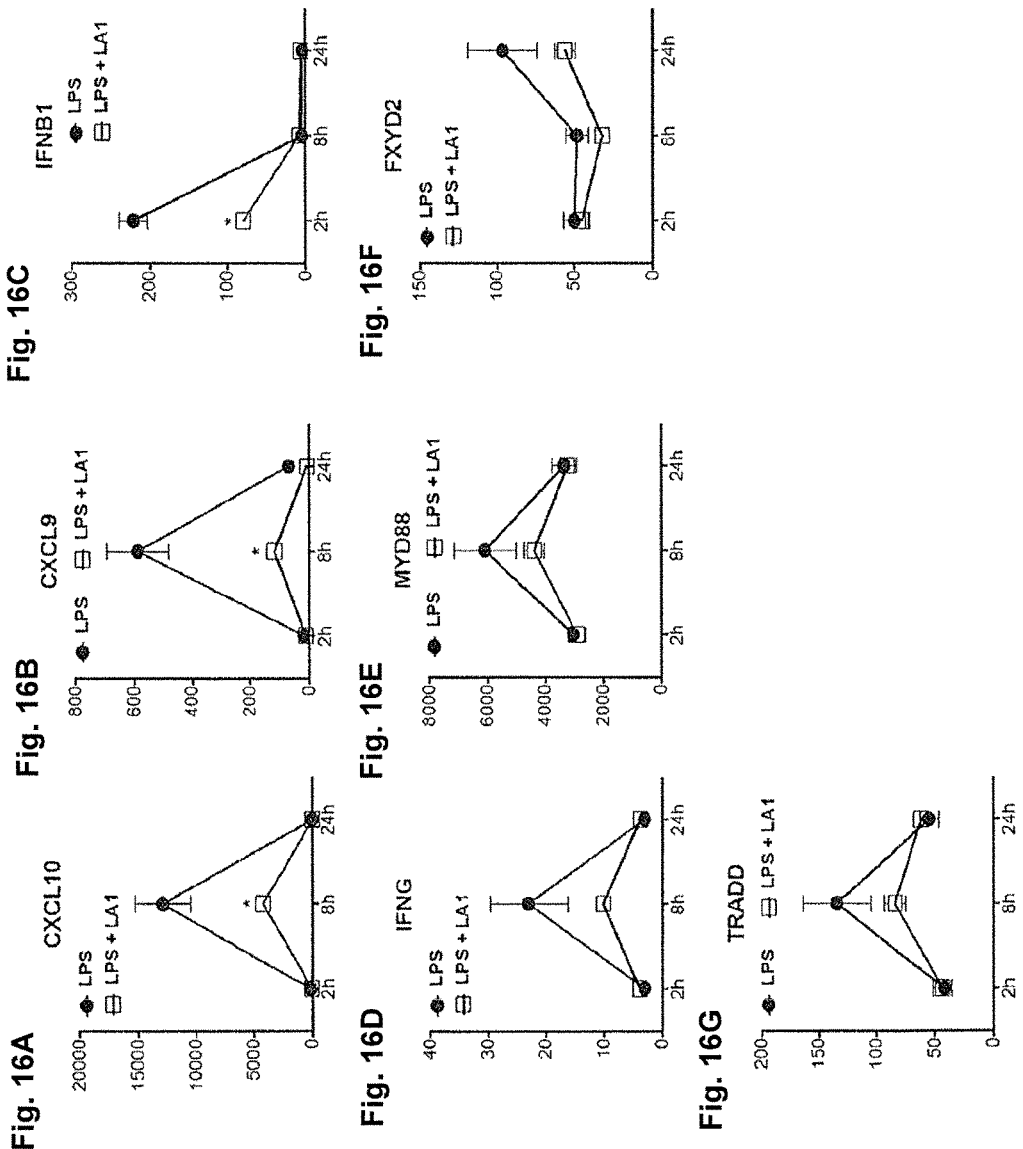

| Upregulated by LA1 |
|---|
| hsa-miR-125b |
| hsa-miR-330-3p |
| hsa-miR-363 |
| hsa-miR-134 |
| hsa-miR-523 |
| hsa-miR-1266 |
| hsa-miR-15b* |
| hsa-miR-877* |
| hsa-miR-130b* |
| hsa-miR-1237 |
| hsa-miR-26b* |
| hsa-miR-191* |

| Downregulated by LA1 |
|---|
| hsa-miR-181d |
| hsa-miR-151-3p |
| hsa-miR-526b |
| hsa-miR-199a-3p |
| hsa-miR-361-5p |
| hsa-miR-95 |
| hsa-miR-551a |
| hsa-miR-365* |
| hsa-miR-1908 |
| hsa-miR-624* |
| hsa-miR-1913 |
| hsa-miR-330-5p |
| hsa-miR-520d-3p |
| hsa-miR-224* |
| hsa-miR-505* |

Fig. 17

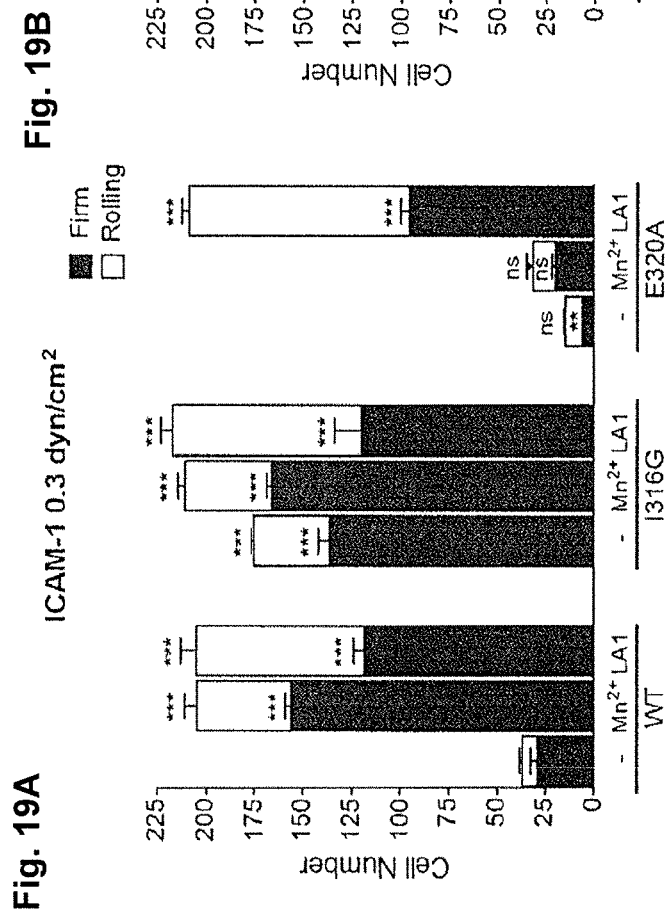

|  |  | Vehicle | LA1 |
|---|---|---|---|
| Hematology | | | |
| Weight | g | 340.57 ± 47.62 | 331.00 ± 39.69 |
| White BCC | × $10^3$/μl | 9.5 ± 1.57 | 8.34 ± 1.27 |
| Red BCC | × $10^6$/μl | 7.66 ± 0.60 | 8.00 ± 0.17 |
| Hemaglobin | g/dl | 13.83 ± 0.76 | 14.50 ± 0.43 |
| Hematocrit | % | 41.14 ± 2.73 | 42.60 ± 1.67 |
| MCV | fL | 53.86 ± 2.67 | 53.20 ± 1.30 |
| MCH | pg | 17.86 ± 0.69 | 18.20 ± 0.45 |
| MCHB | % | 33.71 ± 0.76 | 34.20 ± 0.45 |
| Segmented Neutrophils | % | 9.14 ± 4.18 | 11.80 ± 2.95 |
| Band Neutrophils | % | 0.00 ± 0.00 | 0.00 ± 0.00 |
| Lymphocytes | % | 85.86 ± 7.73 | 82.60 ± 4.28 |
| Monocytes | % | 4.71 ± 3.20 | 5.60 ± 2.30 |
| Eosiniphils | % | 0.29 ± 0.76 | 0.00 ± 0.00 |
| Basophils | % | 0.00 ± 0.00 | 0.00 ± 0.00 |
| NRBC |  | 0.00 ± 0.00 | 0.00 ± 0.00 |
| RBC Morphology |  | Normal | Normal |
| Platelet Morphology |  | Normal | Normal |
| WBC Morphology |  | Normal | Normal |
| Serum Chemistry | | | |
| Glucose | mg/dL | 144.14 ± 20.63 | 120.63 ± 15.21 |
| BUN | mg/dL | 15.86 ± 2.27 | 17.88 ± 1.38 |
| CREA | mg/dL | 0.40 ± 0.08 | 0.46 ± 0.07 |
| Na | mmol/L | 145.57 ± 0.79 | 142.75 ± 3.01 |
| K | mmol/L | 4.61 ± 0.86 | 7.26 ± 3.78 |
| Cl | mmol/L | 106.00 ± 2.52 | 104.25 ± 1.28 |
| CO2 | mmol/L | 27.57 ± 0.98 | 26.25 ± 1.91 |
| Amylase | U/L | 1765.14 ± 503.31 | 1988.50 ± 572.21 |
| Ca | mg/dL | 10.64 ± 0.17 | 10.58 ± 0.40 |
| PO4 | mg/dL | 7.56 ± 1.42 | 7.59 ± 1.68 |
| Cholesterol | mg/dL | 106.57 ± 16.97 | 103.25 ± 6.98 |
| Tryglycerides | mg/dL | 84.86 ± 39.00 | 71.50 ± 30.04 |
| Uric Acid | mg/dL | 0.66 ± 0.27 | 1.70 ± 1.20 |
| Albumin | g/dL | 3.34 ± 0.39 | 3.60 ± 0.48 |
| AST | U/L | 69.86 ± 9.99 | 89.25 ± 9.13 |
| ALT | U/L | 45.86 ± 13.38 | 50.38 ± 13.09 |
| LDH | U/L | 563.86 ± 124.83 | 1057.88 ± 895.96 |
| CPK | U/L | 104.71 ± 16.42 | 135.50 ± 75.20 |
| Alkaline Phosphatase | U/L | 208.14 ± 95.07 | 178.13 ± 29.85 |
| Total Bilirubin | mg/dl | 0.33 ± 0.05 | 0.41 ± 0.11 |

Fig. 20

| Animal # | HEART | KIDNEY | LIVER | LUNG | SPLEEN |
|---|---|---|---|---|---|
| 1 | WNL | WNL | WNL | WNL | WNL |
| 2 | WNL | WNL | WNL | 1+ | WNL |
| 3 | WNL | WNL | WNL | WNL | WNL |
| 4 | WNL | WNL | WNL | WNL | WNL |
| 5 | WNL | WNL | WNL | WNL | WNL |
| 6 | WNL | WNL | WNL | WNL | WNL |
| 7 | WNL | WNL | WNL | WNL | WNL |
| 8 | WNL | WNL | WNL | WNL | WNL |
| 9 | WNL | WNL | WNL | WNL | WNL |
| 10 | WNL | WNL | WNL | WNL | WNL |
| 11 | WNL | WNL | WNL | 1+ | WNL |
| 12 | WNL | WNL | WNL | WNL | WNL |
| 13 | WNL | 2+;3+ | WNL | WNL | WNL |
| 14 | WNL | WNL | WNL | WNL | WNL |
| 15 | WNL | WNL | WNL | WNL | WNL |

| LEGEND | INTENSITY |
|---|---|
| WNL–Within Normal Limits | + = Mild |
| 1) Perivascular Lymphoplasmacytic Infiltration | ++ = Moderate |
| 2) Inflammation chronic, focal, mild | +++ = Extensive |
| 3) Nephrosis tubular, focal, mild | ++++ = Severe |

COMMENTS:

All tissues were within normal limits. The few changes observed were incidental findings.

Fig. 21

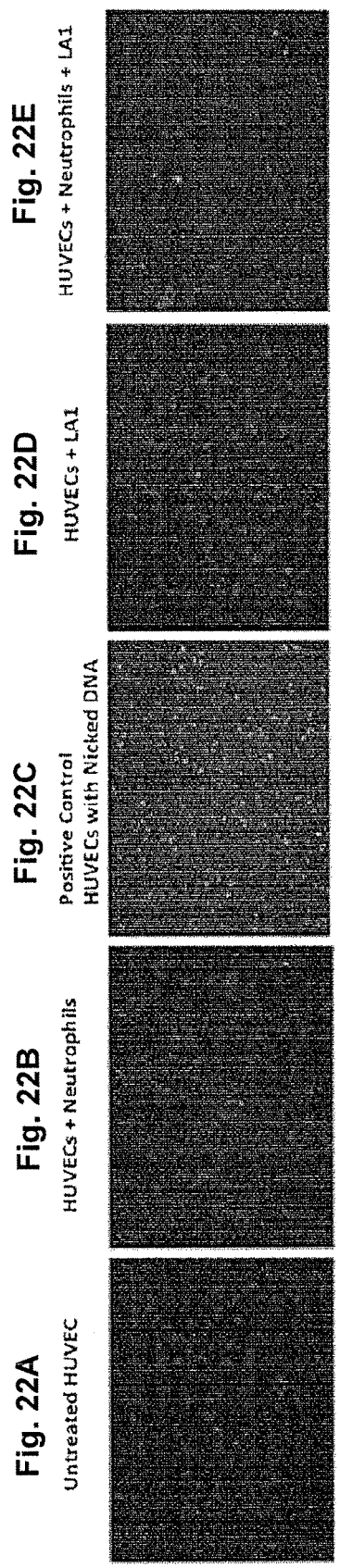

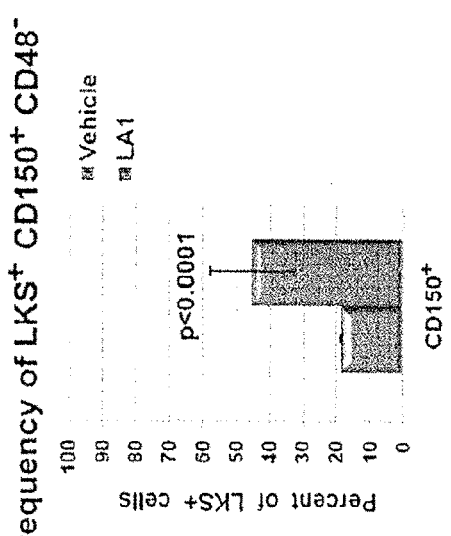
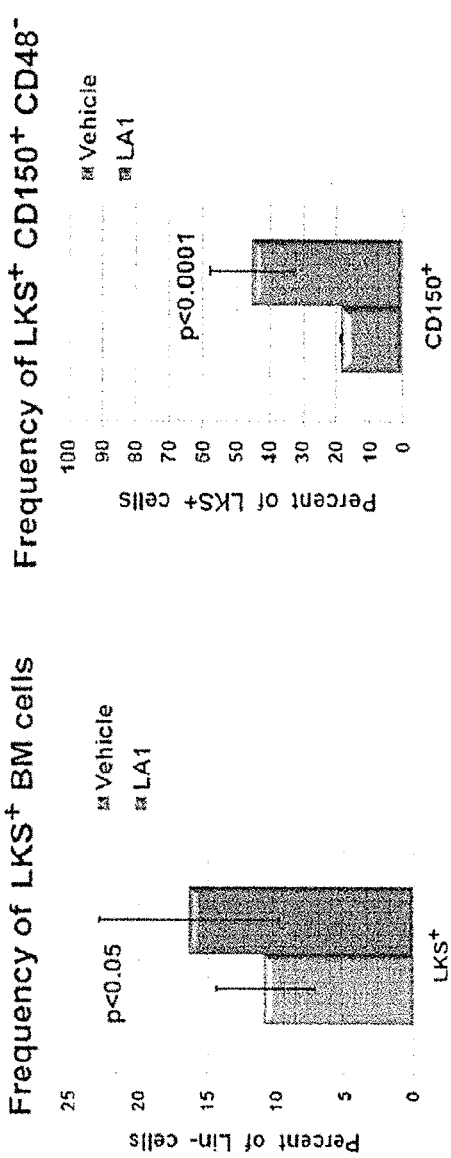
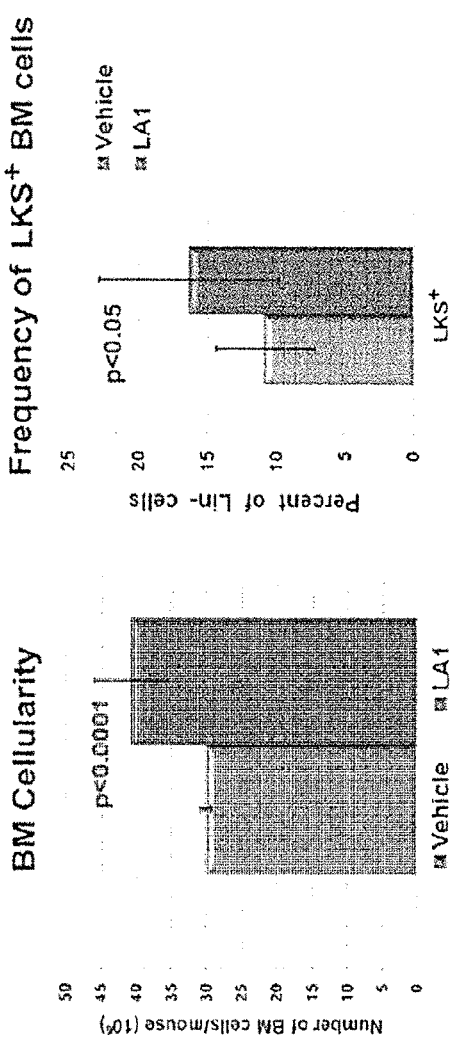

COMPOUNDS AND METHODS FOR REGULATING INTEGRINS

CROSS-REFERENCE TO RELATED APPLICATIONS

This application is a divisional of U.S. application Ser. No. 14/517,667, filed Oct. 17, 2014, which is a continuation of PCT/US2013/037548, filed Apr. 22, 2013, which application claims the benefit of priority to U.S. Provisional Application Ser. No. 61/635,968 filed Apr. 20, 2012, and to U.S. Provisional Application Ser. No. 61/791,523, filed Mar. 15, 2013, which are each incorporated herein by reference in their entirety for all purposes.

BACKGROUND OF THE INVENTION

1. Technical Field

The present invention relates to priming or activation of β2 (beta2) family of integrins with various agents. The present invention further relates to treating various diseases and conditions that involve beta2 family of integrins.

2. Background Art

Integrins are non-covalently linked α/β heterodimeric receptors that mediate cell adhesion, migration and signaling. Together with their ligands, integrins play central roles in many processes including development, hemostasis, inflammation and immunity, and in pathologic conditions such as cancer invasion and cardiovascular disease. Key leukocyte functions, such as activation, migration, tissue recruitment and phagocytosis, are essential for their normal immune response to injury and infection and in various conditions, including inflammatory and autoimmune disorders [1, 2]. The β2 (b2) integrins, a sub-family of α/β heterodimeric integrin receptors have a common β-subunit (β2, CD18) but distinct α-subunits (CD11a, CD11b, CD11c and CD11d [3]) [4]. They regulate leukocyte functions, including via highly expressed integrins CD11a/CD18 (also known as LFA-1) and CD11b/CD18 (also known as Mac-1, CR3 and αMβ2) [2] that recognize a variety of ligands. For example, CD11b/CD18 recognizes >30 ligands, including the complement fragment iC3b, Fibrinogen, CD40L and ICAM-1 as ligands, among various others. CD11b/CD18 has been implicated in many inflammatory and autoimmune diseases. These include ischemia-reperfusion injury (including acute renal failure and atherosclerosis), Multiple Sclerosis (MS), tissue damage, transplantation, lupus, lupus nephritis, macular degeneration, glaucoma, stroke, neointimal thickening in response to vascular injury and the resolution of inflammatory processes [5-9]. For example, leukocyte infiltration and plaques of demyelination in the brain and spinal cord of patients are a hallmark of MS and CD11b/CD18 has been shown to play a key role in mediating leukocyte adhesion, migration and trafficking in MS and is a validated target for MS. Similarly, influx of inflammatory leukocytes potentiates anti-GBM nephritis, which is a model of rapidly progressive glomerulonephritis and lupus nephritis, and is characterized by proteinuria, leukocyte infiltration and glomerular crescent formation [10, 11]. Leukocytes play a critical role in the pathogenesis of anti-GBM nephritis, and their number correlates with the percentage of crescentic glomeruli. CD11b$^{-/-}$ animals show no proteinuria and strong protection of renal function [12], suggesting that agents targeting this integrin have a potential to treat this disease.

According to the American Cancer Society, worldwide, nearly 8 M people die from cancer every year. This number is expected to rise to 13.1 M deaths per year by the year 2030. There were 13.2 M new cases of cancer in the world in 2008, with an associated cost burden of $290 B, and these cases are expected to rise to 22.2 M by 2030, with a cost burden of $458 B. The developing world sees twice as many new cases of cancer as the developed world. Cancer is the second most common cause of death in the US; nearly 600,000 Americans are expected to die of cancer in 2013, almost 1,600 people per day, accounting for nearly 1 of every 4 deaths. About 1.6 M new cancer cases are expected to be diagnosed in 2013.

Breast cancer (BC) is the second most common cancer among women in the US; 1 in 8 women will have BC in their lifetime; BC is also a leading cause of cancer death among women of all races; ~226,000 new cases of invasive BC in 2012; almost 40,000 women die from BC every year. Besides being female, age is the most important risk factor for BC. BC produces no symptoms when the tumor size is small and large tumors may become evident as a breast mass, but are also often painless. Breast pain is more likely to be caused by benign conditions and is not a common early symptom of BC.

Currently, surgical removal of part or whole breast is the most effective treatment for early-stage BC, in combination with radio- and chemo-therapy. Postmenopausal women with early stage breast cancer that tests positive for hormone receptors benefit from treatment with an aromatase inhibitor (e.g., letrozole, anastrozole, or exemestane) in addition to, or instead of, tamoxifen. For women whose cancer tests positive for HER2/neu, approved targeted therapies include trastuzumab (Herceptin) and, for advanced disease, lapatinib (Tykerb) and pertuzumab (Perjetal). The US Food and Drug Administration (FDA) revoked approval of bevacizumab (Avastin) for the treatment of metastatic breast cancer in 2011 because of evidence showing minimal benefit and some potentially dangerous side effects. Thus, additional therapeutics that are more effective and have fewer side effects are greatly needed. Furthermore, adjuvant therapeutics that can significantly reduce the dose of toxic chemo- and radio-therapeutic regimens in patients with BC are greatly needed.

Also, a majority of currently used anticancer therapies have significant cardiovascular safety concerns. Dose-dependent and progressive left ventricular (LV) dysfunction manifesting as symptomatic heart failure is well documented in patients receiving anthracyclines. In women with early breast cancer, particularly those >65 years of age, cardiovascular disease (CVD) is now the most common cause of death as indicated by Surveillance, Epidemiology, and End Results (SEER)-Medicare linked data. Additionally, these women are also at increased risk of CVD compared with age-matched women without a history of breast cancer. Paclitaxel is arrythmogenic cytotoxic drug and leads to bradycardia, with incidence rate with paclitaxel ranging from 0.5% to 5% (and 1.7% with docetaxel). While the main cardiotoxicity of taxanes is bradycardia, ischaemia has also been described. Importantly, clinical trials with the newer therapeutics, such as human epidermal growth factor receptor 2 (HER2)-directed monoclonal antibodies (i.e. trastuzumab) and other newer multi-targeted small-molecule inhibitors show that interfere with molecular pathways crucial to normal cardiac homeostasis, resulting in relatively high incidences of subclinical and overt cardiac toxicity. Even more significantly, while the cardiac toxicity with newer therapies may be reversible, the recovery of LV function after treatment cessation is uncertain at this time. Trastuzumab (Herceptin, a humanized monoclonal antibody against the HER2 tyrosine kinase receptor) shows the incidence of LVEF decrease or asymptomatic heart failure (HF) by ~7%, but it can rise to 13% when trastuzumab is administered with concurrent paclitaxel and to 27% with concurrent anthracyclines. Thus, there is a great need for newer therapeutics for BC, which, in addition to being more efficacious, also lower the cardiovascular risk.

Inflammatory Leukocytes Recruited to Tumor Microenvironment are Targets for Cancer Therapy. Inflammation is directly linked to rumor growth and re-growth post treatment with surgery, anti-cancer agents and radiation. CD45+ leukocytes are significantly upregulated in naïve human breast tumors and after chemo-therapy. Myeloid cells (e.g.; neutrophils and macrophages) are among the cell types that are highly upregulated in the tumors, especially post treatment. In multiple animal models, reducing infiltration of myeloid cells leads to significant reduction in tumor burden, improves efficacy of cancer therapies and reduces BC metastasis. For example, it was recently shown that anti-CD11b antibodies enhance tumor response to radiation in models of squamous cell carcinoma.

Leukocytic β2 integrins also modulate tumor infiltration. For example, tumors also secrete inflammatory cytokines to recruit CD11b-expressing myeloid cells to facilitate neovascularization [13]. During cancer treatments, irradiated tumors recruit large numbers of specific leukocytes, such as bone marrow-derived CD11b-expressing myeloid cells expressing matrix metalloproteinase-9 (MMP-9), that restore tumor vasculature and allow tumor re-growth and recurrence [14]. Recent studies have shown that treatment with CD11b antagonists (anti-CD11b antibody) reduces CD11b-expressing myeloid cell infiltration and an enhancement of tumor response to radiation in mice [14], suggesting that agents targeting this integrin have a potential to be used as therapeutics in oncology.

Additionally, exposure to ionizing radiation (IR) causes injury in animals, eliciting an influx of inflammatory leukocytes that is partly responsible for early (acute) and late (chronic) injury and progressive functional impairment of multiple critical organs in mammals [15-20]. These include the hematopoietic system. The consequences of exposure to ionizing radiation (IR) are of major concern for patients that have, for example, undergone radiation therapy and individuals that are exposed to IR due to nuclear accident or attack. Moreover, exposure to sublethal IR also causes dose-dependent injury, including the hematological toxicity and also affects both the hematopoietic stem cell (HSC) numbers and their function (functional damage), including their capacity for long-term repopulation [21-26]. Therefore, blockage or reduction of inflammatory responses after radiation exposure could help mitigate early (acute) and late (chronic) effects of radiation in exposed patients.

Furthermore, acquired bone marrow failure (BMF) develops after an injury to the bone marrow (BM) by ionizing radiation (IR), chemotherapy drugs and antibiotics (e.g. busulfan and chloramphenicol), toxic chemicals (benzene, carbon tetrachloride), or viral infection (hepatitis, HIV, CMV, parvovirus). Another form of acquired BMF called aplastic anemia is an immune-mediated BMF that develops after lymphocyte infusion, and is characterized by an immune-mediated functional impairment of hematopoietic stem cells (HSCs). Functional damage in HSCs can over time lead to development of acquired BMF.

CD11b/CD18 is also expressed on short-term repopulating hematopoietic stem cells (HSCs) and hematopoietic progenitors (HPCs), and has been shown to participate in the retention and anchoring of HPCs in the bone marrow during enforced mobilization, suggesting that agents targeting CD11b/CD18 can have a protective effect on the number and function of HSCs and HPCs, in vitro, ex vivo, and in vivo.

Studies over the last several years have shown that blocking CD11b/CD18 and its ligands with antibodies and ligand mimics (anti-adhesion therapy) [24-26] and genetic ablation of CD11b or CD18 decreases the severity of inflammatory response in vivo in many experimental models [27, 28]. However, such blocking agents have had little success in treating inflammatory/autoimmune diseases in humans [28, 29], perhaps because complete blockage of CD11b/CD18 with antibodies is difficult due to availability of a large mobilizable intracellular pool of CD11b/CD18 [30, 31] or because suppressing leukocyte recruitment with blocking agents requires occupancy of >90% of active integrin receptors [2]. Anti-integrin β2 antibodies have also shown unexpected side effects [33]. Additionally, whether transient activation of a fraction of native integrin receptors in vivo, as is expected from treatment with an activating agent, will have any significant biological effect in physiologically relevant settings remains an open question.

A number of published reports in the literature show that, in addition to increasing cell adhesion and modulating migration, CD11b/CD18 activation mediates a number of intracellular signaling events, mediate a number of intracellular signaling events, including production of reactive oxygen species and modulation of a number of pro- and anti-inflammatory genes in inflammatory cells [27-32]. Integrin activation and ligand binding leads to its clustering on the cell surface and initiates outside-in signaling, including the activation of PI3-K/Akt and MAPK/ERK1/2 pathways [28, 33], thereby mimicking the anchorage-dependent pro-survival signals in most cells. Ligation and clustering of integrins also synergistically potentiates intracellular signaling by other receptors (such as, Toll-like receptors (TLRs) and cytokine receptors interleukin-1 receptor (IL-1R) and TNFR) and both induce transcription factor (such as, NF-κB) dependent expression of pro-inflammatory cytokines (e.g.; IL1β, IL6, TNF-α) as well as release of other factors (e.g.; Tissue Factor). CD11b/CD18 deficiency enhances TLR4-triggered production of pro-inflammatory cytokines. The above suggests that CD11b/CD18 and its activation has a protective role in healthy mammals and that in inflammatory conditions or diseases, CD11b/CD18 activation would also suppress inflammation, inflammatory injury and disease by negatively regulating pro-inflammatory pathways in CD11b/CD18-expressing cells [34-36].

The above also suggests that there is a considerable potential for agents that modulate the function of CD11b/CD18 as therapeutic agents for the treatment of various inflammatory conditions. CD11b/CD18 is normally expressed in a constitutively inactive conformation in circulating leukocytes and in many other cells, but is rapidly activated to mediate its various biological functions [23]. CD11b/CD18 is also expressed on many cell types and tissues, including microgila, hepatocytes, HSCs, HPCs and a sub-type of T- and B-cells. CD11b/CD18 is also found in its cleaved, soluble form in some instances [37].

Blocking beta2 integrins, including CD11b/CD18, and their ligands with antibodies and ligand mimics (anti-adhesion therapy) [38-40] and genetic ablation of CD11a, CD11b, CD11c or CD18 decreases the severity of inflammatory response in vivo in many experimental models [41-43]. However, such blocking agents have had little success in treating inflammatory/autoimmune diseases in humans [42, 44], perhaps because complete blockage of integrins with antibodies is difficult due to availability of a large mobilizable intracellular pool of such integrins (for example, CD11b/CD18) [45, 46] or because suppressing leukocyte recruitment with blocking agents requires occupancy of >90% of active integrin receptors [47]. Anti-integrin β2 antibodies have also shown unexpected side effects [48]. Additionally, whether transient activation of a fraction of native integrin receptors in vivo, as is expected from treatment with an activating agent, will have any significant biological effect in physiologically relevant settings remains an open question.

Therefore, there is a considerable need for novel agents, such as antibodies, proteins, peptides, chemical compounds and small molecules, that selectively regulate the ligand binding and function of β2 integrins, including integrins CD11a/CD18, CD11b/CD18 and CD11c/CD18. Additionally, there is a need for agents that activate integrins (agonists). Such agonists can enhance the function of β2 integrins by, for example, targeting or binding to an allosteric regulatory site, such as the hydrophobic site-for-isoleucine (SILEN) pocket in CD11b/CD18, and other similar sites, but not the ligand-binding site on the integrin. Thus, there is a need for integrin activating agents that do not block ligand-binding functions of integrins. Moreover, agents and methods to enhance or promote integrin-mediated cell-adhesion and cellular functions are highly desired. However, progress towards identifying such agonists has been slow, especially agonists that selectively target and activate β2 integrins, including CD11b/CD18, with only a few reported discoveries [49, 50].

The present invention describes novel CD11b/CD18 agonists and a novel approach that involves integrin CD11b/CD18 priming for activation or activation, rather than its blockade, as a strategy for modulating CD11b/CD18 function. Such biological functions include cell adhesion, ligand binding, migration, phagocytosis, and the generation of effector molecules, such as cytokines. The present invention further describes compounds and approaches for modulating the function of CD11b/CD18 expressing cells (such as leukocytes, microglia, hepatocytes and lymphocytes), including their adhesion, migration, recruitment and other biological functions. It was strategized that various agents, such as small molecules, which are easily delivered in vivo and can be readily optimized for use in different mammals, would be the best approach for activating integrins. Here, it is shown that, without limitation, inflammatory disease can be reduced by CD11b/CD18 activation with novel small molecules. This shows that integrin activation is a novel, useful, pharmacologically targetable methodology to treat, without limitation, a variety of inflammatory and autoimmune diseases and conditions.

The present invention also shows that CD11b/CD18 activating agents that activate the normal wild type form of CD11b/CD18 and any of its mutant forms, such as the R77H mutant commonly found in many autoimmune disease carrying patients [51], would be highly beneficial. This invention describes a novel strategy, as an alternative to the anti-adhesion strategy that is currently practiced in literature, for regulating the biological function of integrins and integrin-expressing cells. Many different types of agents can activate integrins, such as biologics, antibodies, antibody fragments, proteins, lipids, oligonucleotides and chemical compounds.

An important requirement of useful agonists and compositions that regulate β2 integrins, including CD11b/CD18, is that they do not negatively impact the cell, tissue and animal viability. It is an object of the present invention to describe such agonists, compositions and methods. In addition, it is an objective of the present invention to show that transient activation of a fraction of native receptors in vivo, as is expected from treatment with an agonist and method of this invention, has a biological effect in physiologically relevant model systems. In addition, the present invention provides other related advantages. Moreover, an important requirement of useful compounds and compositions that regulate beta2 integrins, including CD11b/CD18, is that they not negatively impact the cell, tissue and animal viability. Some have suggested that integrin agonists might induce killing of target cells (Yang et al., *J Biol Chem* 281, 37904 (2006)), which is not desirable. Also, there is some prior art on the thiazolidine-one family of compounds, including U.S. Pat. No. 5,225,426, U.S. Pat. No. 7,566,732, U.S. Pat. No. 7,348,348, US 2006/0281798, US 2006/0183782, US 2006/0106077, US 2008/0108677, US 2010/0056503, WO 2009026346, WO/1995/029243. However, no compounds or methods with above described desirable properties have so far been described in the literature. It is an object of the invention to describe such compounds and methods. In addition, the present invention provides other related advantages.

Furthermore, integrins are now shown to exist in more than two conformations (closed and open). For example, CD11a/CD18 has been shown to exist in at least three conformations—closed, intermediate and open—based on its affinity for its ligand ICAM-1 in each of these states [52]. This also suggests, although has not been previously shown, that these different integrin conformations will induce different intracellular signaling pathways. It is an object of the current invention to describe β2 integrin agonists that, upon binding to β2 integrins, activate the β2 integrins and induce intracellular signaling pathways that are different from the ligand-bound β2 integrin conformation(s).

Moreover, a number of agents currently under development as anti-inflammatory agents are targeted towards specific kinases, such as spleen tyrosine kinase (Syk), T cell receptor-associated protein kinase (ZAP70), Janus kinases (JAKs) and Bruton's tyrosine kinase (BTK) [53]. There remains a need for compounds and methods that effectively treat inflammation, especially targeting those kinases.

SUMMARY OF THE INVENTION

The present invention provides for a method of treating inflammation, by administering an effective amount of a β2 integrin agonist to a patient, and reducing inflammation.

The present invention provides for a method of treating cancer, by administering an effective amount of a β2 integrin agonist to a patient, and reducing tumor growth.

The present invention provides for a method of treating a patient exposed to radiation, by administering an effective amount of a β2 integrin agonist to the patient after radiation exposure, and mitigating the effects of radiation exposure in the patient.

The present invention also provides for a method of preventing effects of radiation, by administering an effective amount of a β2 integrin agonist to the patient prior to radiation exposure, and preventing the effects of radiation exposure on the patient.

The present invention provides for a method of treating acquired bone marrow failure (BMF), by administering an effective amount of a β2 integrin agonist to a patient.

The present invention further provides for a method of improving the health of damaged vasculature in a patient, by administering a β2 integrin agonist to the patient, and improving re-vascularization in the patient.

The present invention provides for a method of activating β2 integrins, by interacting the β2 integrin with an agonist, and stabilizing the b2 integrin in an intermediate affinity conformation.

DESCRIPTION OF THE DRAWINGS

Other advantages of the present invention are readily appreciated as the same becomes better understood by reference to the following detailed description when considered in connection with the accompanying drawings wherein:

FIG. 2A is a graph of tumor growth, FIG. 2B is an in vivo bioluminescence image of a control group, and FIG. 2C is an in vivo bioluminescence image of a LA1 treatment group;

FIG. 4A is a histogram showing quantitation of the wound-healing data presented in the photograph of FIG. 4B, representative images shown are from one well of a triplicate well experiment from one of at least two to three independent experiments, dotted lines represent the wound margins at the beginning of the experiment (0 hours), black scale bar represents 50 μm;

FIG. 5A shows confocal microscopy images of CD11b distribution on the surface of K562 WT cells, and FIG. 5B is a histogram showing ImageJ based quantitation of the number of CD11b macro clusters per cell from each of the conditions shown in FIG. 5A;

FIG. 6A is an immunoblot of whole cell lysates from K562 WT cells treated in suspension for 45 min at 37° C. with either PKC agonist PMA (positive control), DMSO (vehicle), non-selective agonist $Mn^{2+}$ (1 mM), activating mAb KIM127 (1:100 dilution of ascites fluid), activating mAb 24 (20 □g/mL) or the agonist LA1 (15 □M) probed for phosphorylated ERK (pERK; pThr202/pTyr204) and total ERK, FIG. 6B is an immunoblot of the cell lysates probed for phosphorylated JNK (pJNK; pThr183/pTyr185) and total JNK, FIGS. 6C and 6D are immunoblots of whole cell lysates from K562 WT cells treated as in 6A and 6B but in the presence of ligand fibrinogen (50 □g/mL);

FIGS. 7A-7B show that agonist LA1 does not induce global conformational changes in CD11b/CD18, FIG. 7A is a histogram showing the level of CD11b/CD18 expression on the surface of live K562 WT cells using heterodimer specific antibody IB4 (right) and the isotype IgG2a control mAb (left), as measured using flow cytometry, and FIG. 7B is a FACS analysis on live K562 WT cells showing the reactivity of CD11b/CD18 conformation reporter probe antibodies KIM127 (1:50 dilution of ascites) and mAb 24 (15 ug/mL) under various conditions;

FIGS. 8A-8D show that agonists LA1 and ED7 similarly reduce the influx of macrophages in injured arteries, FIGS. 8A-8C are representative FACS analyses plots of single cell suspensions for $CD11b^+$ macrophages (based on binding with anti-rat CD11b antibody WT.5) in arteries 7 days after balloon injury from rats treated post-surgery with a vehicle control (8A), activating anti-CD11b mAb ED7 (3.3 mg/kg/d) (8B) or LA1 (1 mg/kg/d) (8C), and FIG. 8D is a bar graph showing quantitation of $CD11b^+$ macrophages in the injured arteries from multiple animals (n=4-6/group);

FIGS. 9A-9D show that agonist LA1 is better at ameliorating vascular injury as compared to activating anti-CD11b antibody ED7, FIGS. 9A-9C are representative photomicrographs of arteries 21 days after balloon injury from rats treated post-surgery with a control irrelevant mouse IgG (mIgG1, 4 mg/kg/d) (9A), activating anti-CD11b mAb ED7 (4 mg/kg/d) (9B) or LA1 (1 mg/kg/d) (9C) (arrows point to the neoinitmal thickening), and FIG. 9D is a bar graph showing the neointima to media ratio determined by morphometric analysis of the injured arteries from the treated animals (n=6-7/group);

FIG. 10A shows the chemical structure of agonist LA2, and FIG. 10B shows the chemical structure of agonist LA15;

FIG. 13A is confocal microscopy images of CD11b distribution on the surface of K562 WT cells, FIG. 13B is a histogram showing ImageJ based quantitation of the number of CD11b macro clusters per cell from each of the conditions shown in 13A above;

FIGS. 14A-14D show that agonist LA1 dose-dependently reduces vascular injury in wild type rats, FIGS. 14A-14C are representative photomicrographs of arteries 21 days after balloon injury from rats treated post-surgery with vehicle control (14A), low dose of agonist LA1 (0.05 mg/kg/d) (14B) or a more effective dose of LA1 (1 mg/kg/d) (14C) (arrows point to the neoinitmal thickening), and FIG. 14D is a bar graph showing the neointima to media ratio determined by morphometric analysis of the injured arteries from the treated animals (n=6-7/group).

FIGS. 15A-15G are graphs showing mRNA levels of pro-inflammatory factors that are upregulated by LPS treatment are significantly reduced in cells co-treated with LA1;

FIGS. 16A-16G are graphs showing mRNA levels of pro-inflammatory factors that are upregulated by LPS treatment are significantly reduced in cells co-treated with LA1;

FIG. 17 is a chart showing that levels of a number of micro RNAs are modulated;

FIGS. 19A-19B are graphs showing adhesive behavior of vehicle-, Mn2+ or LA-treated various CD11b/CD18 transfectants under the wall shear stress of 0.3 dyn/cm2;

FIG. 20 shows that the biochemical measurements in serum and liver of LA1-treated rats revealed no appreciable changes in enzyme levels or serum constituents, such as proteins, cholesterol, urea and creatinine;

FIG. 21 shows no significant alterations either in relative organ weights or their histology were discernible at terminal autopsy;

FIGS. 22A-22E are confocal images of DAPI-stained Human Umbilical Vein Endothelial Cells;

FIGS. 26A-26C are graphs showing the analysis of hematopoiesis and HSC compartment in LA1 (Red bars), Vehicle control (Blue bars) treated groups of mice at 4 weeks after 6 Gy of total body irradiation (TBI);

DETAILED DESCRIPTION OF THE INVENTION

Figure 1:
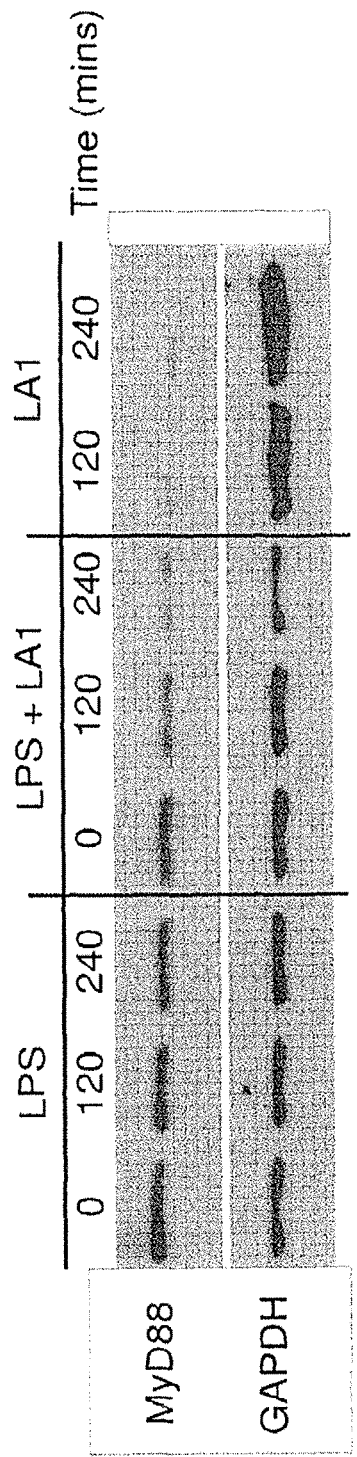
FIG. 1 is a photograph showing that β2 integrin agonist leukadherins, such as LA1, accelerate MyD88 degradation.

The present invention is generally directed to various agents, including chemical compounds termed leukadherins, and methods for priming or activating β2 integrins, especially CD11b/CD18. In other words, the agents of the present invention act as agonists of β2 integrins, rather than antagonists. The agonists and methods are useful for treating various inflammatory and autoimmune diseases, and cancer among other diseases.

One aspect of the invention relates to a compound of Formula (I)

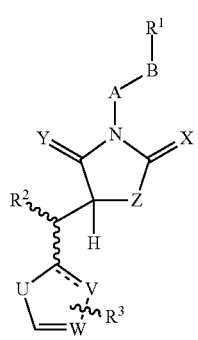

(I)

wherein

A is absent or is selected from alkyl and alkenyl;

B is absent or is selected from alkyl, alkenyl, O, S and $NR^4$;

N is nitrogen;

X and Y are independently selected from O and S;

Z is selected from $CR^4$, O, S and $NR^4$;

U, V and W are independently selected from $CR^4$, O, S and $NR^4$;

$R^1$ and $R^3$ are independently selected from acyl, alkyl, alkenyl, alkynyl, hydroxyalkyl, aminoalkyl, thioalkyl, aryl, aralkyl, carboxyaryl, alkoxyalkyl, alkoxyaryl, alcoxycarbonylaryl, aminoaryl, amidoaryl, haloaryl, heteroaryl, heteroaralkyl, carbocyclyl, heterocyclyl, heterocyclylalkyl, alkoxycarbonyl, alkylaminocarbonyl, alkylthiocarbonyl, sulfonate, alkylsulfonate, arylsulfonate, sulfone, alkylsulfone, arylsulfone, sulfoxide, alkylsulfoxide, arylsulfoxide, alkylsulfonamide, arylsulfonamide, and sulfonamide, piperidinyl, morpholinyl, pyrrolidinyl, phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzyl, benzofuryl, dibenzofuryl, benzthienyl, benzoxazolyl, benzothiazolyl, benzimidazolyl, pyridoimidazolyl, pyrimidoimidazolyl, pyridopyrazolyl, pyrazolopyrimidinyl, and any of which is optionally substituted with 1-6 independent substituents;

$R^2$ selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl; and $R^4$ is absent or is selected from hydrogen and alkyl.

In certain embodiments, Z is S. In certain embodiments, X and Y are O. In certain other embodiments, X and Y are S. In certain other embodiments, X is S and Y is O. In certain other embodiments, X and Y are O and Z is S. In certain other embodiments, X, Y and Z are S. In certain other embodiments, X and Z are S and Y is O. In certain embodiments, U is O and V and W are $CR^4$. In certain such embodiments, $R^4$ is hydrogen. In certain other embodiments, U is S and V and W are $CR^4$. In certain such embodiments, $R^4$ is hydrogen. In certain other embodiments, U is $CR^4$, V is N and W is O. In certain such embodiments, $R^4$ is hydrogen. In certain other embodiments, U is $CR^4$, V is O and W is N. In certain such embodiments, $R^4$ is hydrogen. In certain embodiments, B is alkyl and A is absent. In certain such embodiments, $R^1$ is selected from alkoxycarbonyl, aryl, heteroaryl, carbocyclyl, heterocyclyl and alkoxycarbonyl. In certain embodiments, B is methylene and A is absent. In certain such embodiments, $R^1$ is selected from alkoxycarbonyl, aryl, heteroaryl, carbocyclyl, heterocyclyl and alkoxycarbonyl. In certain such embodiments, B is methylene and A is absent. In certain embodiments, where A is alkyl and B is absent, $R^1$ is alkoxycarbonyl. In certain embodiments, A and B are both absent. In certain such embodiments, $R^1$ is selected from alkoxycarbonyl, aryl, heteroaryl, carbocyclyl, heterocyclyl and alkoxycarbonyl. In certain embodiments, $R^1$ substituent is further substituted with 1-6 independent substituents. In certain embodiments, $R^1$ is selected from furan, phenyl, benzyl, tetrahydrofuran, tetrahydrothiophene, pyrrolidine, tetrahydropyran, tetrahydrothiopyran, piperidine, piperazine, and morpholine. In certain embodiments $R^1$ is selected from tetrahydrofuran, tetrahydrothiophene, and pyrrolidine, preferably tetrahydrofuran. In certain embodiments, $R^1$ is phenyl, preferably substituted phenyl. In certain such embodiments, $R^1$ is phenyl substituted one to five, preferably one to three, more preferably one or two times. In certain such embodiments, $R^1$ is phenyl substituted with one or two, preferably one substituent independently selected from halogen, nitro, cyano, hydroxyl, thiol, amino, alkoxy, alkylamino, alkylthio, hydroxyalkyl, alkoxyalkyl, aminoalkyl, thioalkyl, and alkyl, more preferably from alkyl and halogen, e.g., from methyl, fluoro and chloro. In certain embodiments, $R^2$ is selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, $R^3$ is selected from alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, $R^2$ is hydrogen and $R^3$ is selected from aryl, aralkyl, heteroaryl, heteroaralkyl, carbocyclyl, carbocyclylalkyl, heterocyclyl, and heterocyclylalkyl, preferably aryl, heteroaryl, carbocyclyl, and heterocyclyl. In certain embodiments, $R^3$ is heteroaryl selected from pyrrole, furan, pyrimidine, oxazole, isooxazole and thiophene, preferably furan. In certain embodiments, $R^3$ is furan substituted one to three, preferably one to two times, more preferably once. In certain such embodiments, $R^3$ is furan substituted once with a substituent selected from aryl, aralkyl, heteroaryl, heteroaralkyl, carbocyclyl, carbocyclylalkyl, heterocyclyl and heterocyclylalkyl, preferably aryl, heteroaryl, carbocyclyl, and heterocyclyl. In certain embodiments, $R^3$ is furan substituted once with an aryl group, which itself is optionally substituted, preferably one to two times with alkyl, carboxyl, alkoxycarbonyl and halogen, e.g., chlorophenyl, dichlorophenyl, carboxyphenyl. In certain embodiments, $R^3$ is aryl, preferably phenyl. In certain such embodiments, $R^3$ is phenyl substituted with one or two, preferably two substituents independently selected from halogen, nitro, cyano, hydroxyl, thiol, amino, alkoxy, alkylamino, alkylthio, hydroxyalkyl, alkoxyalkyl, aminoalkyl, thioalkyl, and alkyl. In certain such embodiments, $R^3$ is phenyl substituted once with a halogen, preferably bromo.

One aspect of the invention relates to a compound of Formula (II)

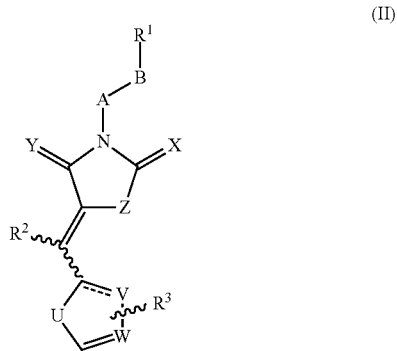

(II)

wherein

A is absent or is selected from alkyl and alkenyl;

B is absent or is selected from alkyl, alkenyl, O, S and $NR^4$;

N is nitrogen;

X and Y are independently selected from O and S;

Z is selected from $CR^4$, O, S and $NR^4$;

U, V and W are independently selected from $CR^4$, O, S and $NR^4$;

$R^1$ and $R^3$ are independently selected from acyl, alkyl, alkenyl, alkynyl, hydroxyalkyl, aminoalkyl, thioalkyl, aryl, aralkyl, carboxyaryl, alkoxyalkyl, alkoxyaryl, alcoxycarbonylaryl, aminoaryl, amidoaryl, haloaryl, heteroaryl, heteroaralkyl, carbocyclyl, heterocyclyl, heterocyclylalkyl, alkoxycarbonyl, alkylaminocarbonyl, alkylthiocarbonyl, sulfonate, alkylsulfonate, arylsulfonate, sulfone, alkylsulfone, arylsulfone, sulfoxide, alkylsulfoxide, arylsulfoxide, alkylsulfonamide, arylsulfonamide, and sulfonamide, piperidinyl, morpholinyl, pyrrolidinyl, phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzyl, benzofuryl, dibenzofuryl, benzthienyl, benzoxazolyl, benzothiazolyl, benzimidazolyl, pyridoimidazolyl, pyrimidoimidazolyl, pyridopyrazolyl, pyrazolopyrimidinyl, and any of which is optionally substituted with 1-6 independent substituents;

$R^2$ selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl; and $R^4$ is absent or is selected from hydrogen and alkyl.

In certain embodiments, Z is S. In certain embodiments, X and Y are O. In certain other embodiments, X and Y are S. In certain other embodiments, X is S and Y is O. In certain other embodiments, X and Y are O and Z is S. In certain other embodiments, X, Y and Z are S. In certain other embodiments, X and Z are S and Y is O. In certain embodiments, U is O and V and W are $CR^4$. In certain such embodiments, $R^4$ is hydrogen. In certain other embodiments, U is S and V and W are $CR^4$. In certain such embodiments, $R^4$ is hydrogen. In certain other embodiments, U is $CR^4$, V is N and W is O. In certain such embodiments, $R^4$ is hydrogen. In certain other embodiments, U is $CR^4$, V is O and W is N. In certain such embodiments, $R^4$ is hydrogen. In certain embodiments, B is alkyl and A is absent. In certain such embodiments, $R^1$ is selected from alkoxycarbonyl, aryl, heteroaryl, carbocyclyl, heterocyclyl and alkoxycarbonyl. In certain embodiments, B is methylene and A is absent. In certain such embodiments, $R^1$ is selected from alkoxycarbonyl, aryl, heteroaryl, carbocyclyl, heterocyclyl and alkoxycarbonyl. In certain such embodiments, B is methylene and A is absent. In certain embodiments, where A is alkyl and B is absent, $R^1$ is alkoxycarbonyl. In certain embodiments, A and B are both absent. In certain such embodiments, $R^1$ is selected from alkoxycarbonyl, aryl, heteroaryl, carbocyclyl, heterocyclyl and alkoxycarbonyl. In certain embodiments, $R^1$ substituent is further substituted with 1-6 independent substituents. In certain embodiments, $R^1$ is selected from furan, phenyl, benzyl, tetrahydrofuran, tetrahydrothiophene, pyrrolidine, tetrahydropyran, tetrahydrothiopyran, piperidine, piperazine, and morpholine. In certain embodiments $R^1$ is selected from tetrahydrofuran, tetrahydrothiophene, and pyrrolidine, preferably tetrahydrofuran. In certain embodiments, $R^1$ is phenyl, preferably substituted phenyl. In certain such embodiments, $R^1$ is phenyl substituted one to five, preferably one to three, more preferably one or two times. In certain such embodiments, $R^1$ is phenyl substituted with one or two, preferably one substituent independently selected from halogen, nitro, cyano, hydroxyl, thiol, amino, alkoxy, alkylamino, alkylthio, hydroxyalkyl, alkoxyalkyl, aminoalkyl, thioalkyl, and alkyl, more preferably from alkyl and halogen, e.g., from methyl, fluoro and chloro. In certain embodiments, $R^2$ is selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, $R^3$ is selected from alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, $R^2$ is hydrogen and $R^3$ is selected from aryl, aralkyl, heteroaryl, heteroaralkyl, carbocyclyl, carbocyclylalkyl, heterocyclyl, and heterocyclylalkyl, preferably aryl, heteroaryl, carbocyclyl, and heterocyclyl. In certain embodiments, $R^3$ is heteroaryl selected from pyrrole, furan, pyrimidine, oxazole, isooxazole and thiophene, preferably furan. In certain embodiments, $R^3$ is furan substituted one to three, preferably one to two times, more preferably once. In certain such embodiments, $R^3$ is furan substituted once with a substituent selected from aryl, aralkyl, heteroaryl, heteroaralkyl, carbocyclyl, carbocyclylalkyl, heterocyclyl and heterocyclylalkyl, preferably aryl, heteroaryl, carbocyclyl, and heterocyclyl. In certain embodiments, $R^3$ is furan substituted once with an aryl group, which itself is optionally substituted, preferably one to two times with alkyl, carboxyl, alkoxycarbonyl and halogen, e.g., chlorophenyl, dichlorophenyl, carboxyphenyl. In certain embodiments, $R^3$ is aryl, preferably phenyl. In certain such embodiments, $R^3$ is phenyl substituted with one or two, preferably two substituents independently selected from halogen, nitro, cyano, hydroxyl, thiol, amino, alkoxy, alkylamino, alkylthio, hydroxyalkyl, alkoxyalkyl, aminoalkyl, thioalkyl, and alkyl. In certain such embodiments, R³ is phenyl substituted once with a halogen, preferably bromo.
In certain embodiments, a compound of Formula II is selected from
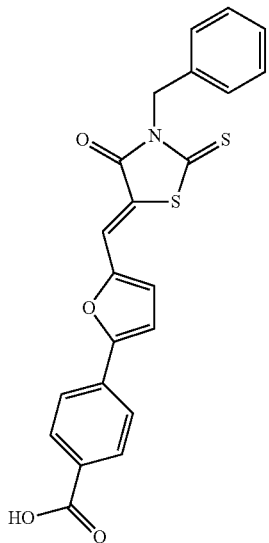
1
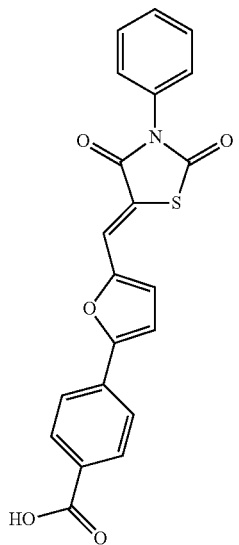
2
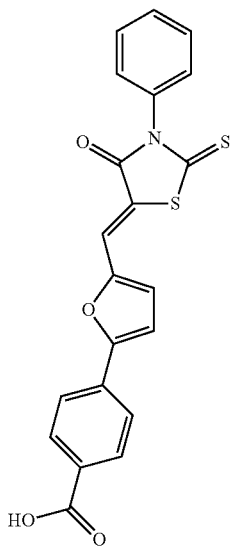
3
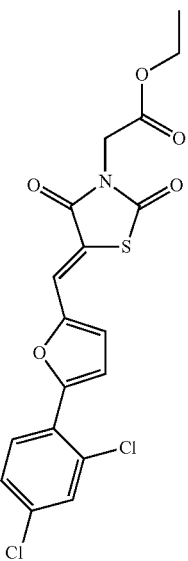
4
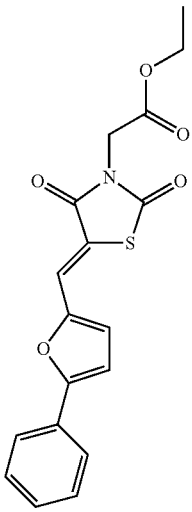
5

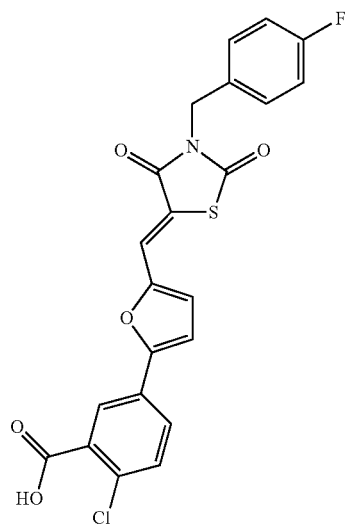
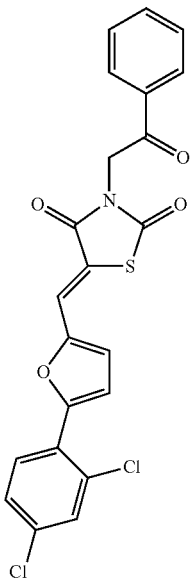
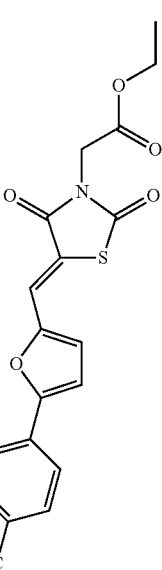

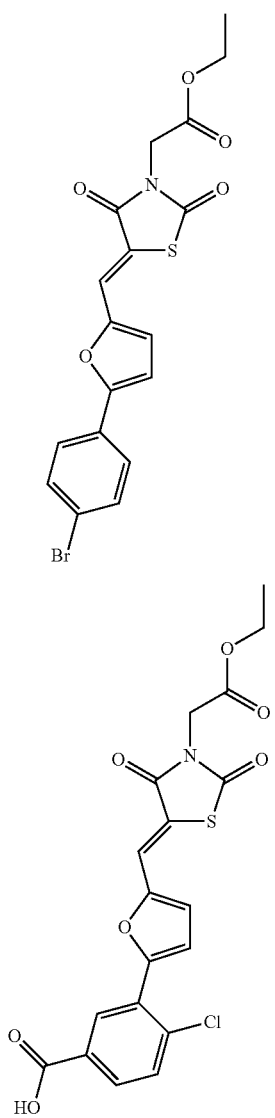
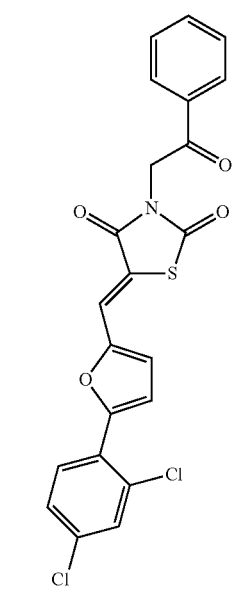
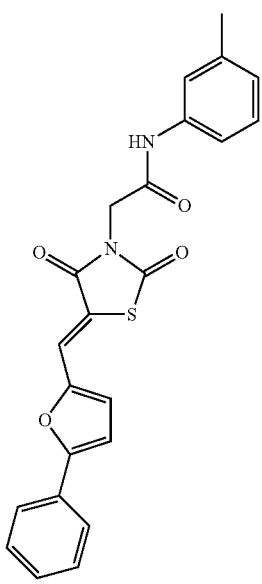
In certain embodiments, a compound of Formula II selected from the following compounds is less preferred
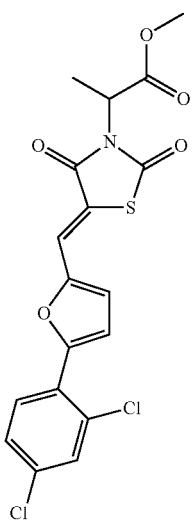

16
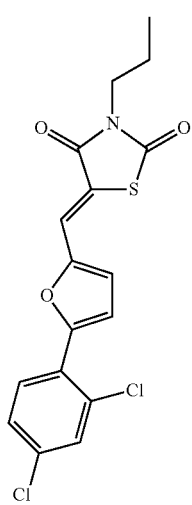
17
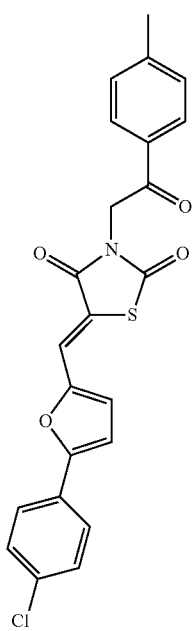
18
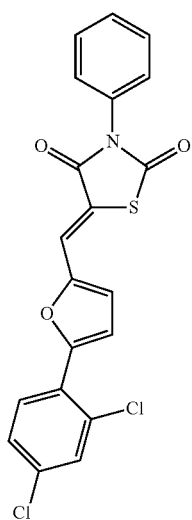
19
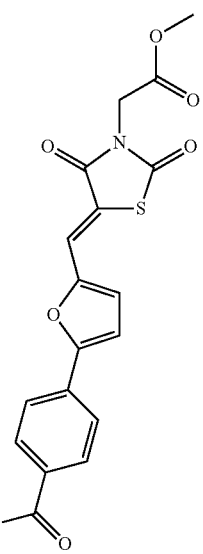
20
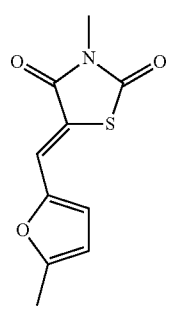
21
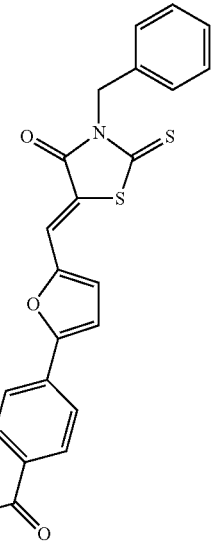

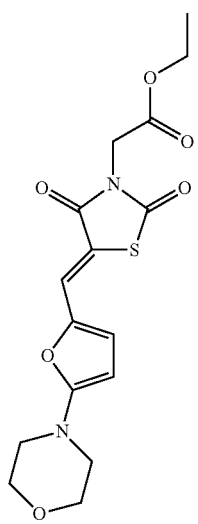
22
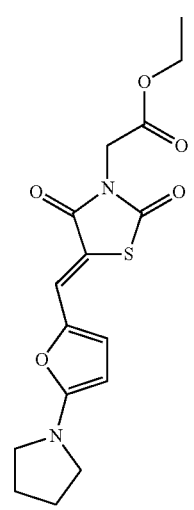
23
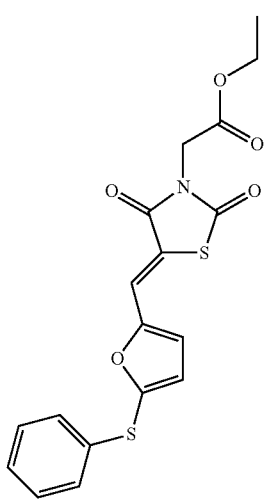
24
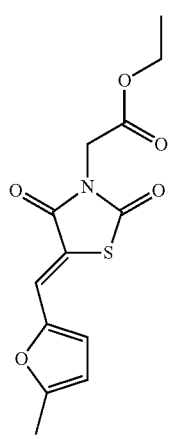
25
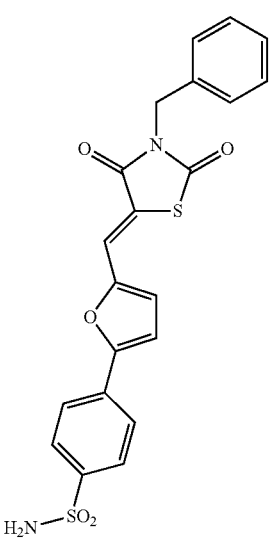
26
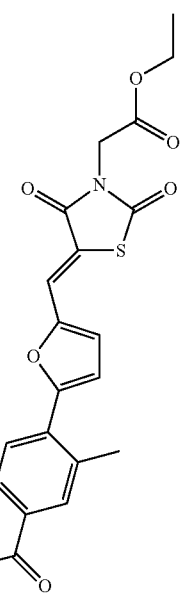
27

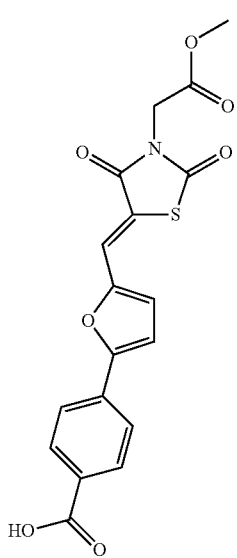

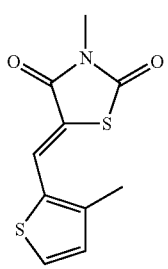

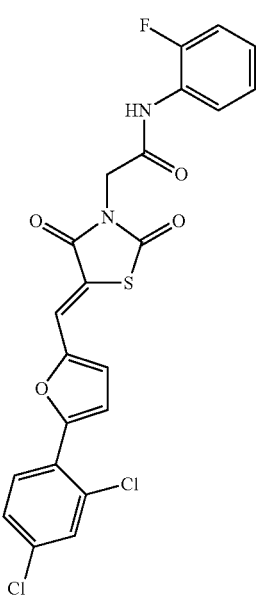

One aspect of the invention relates to a compound of Formula (III)

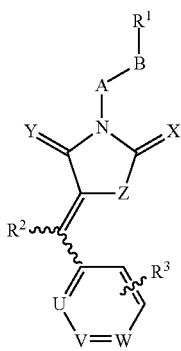

wherein
A is absent or is selected from alkyl and alkenyl;
B is absent or is selected from alkyl, alkenyl, O, S and $NR^4$;
N is nitrogen;
X and Y are independently selected from O and S;
Z is selected from $CR^4$, O, S and $NR^4$;
U, V and W are independently selected from $CR^4$, O, S and $NR^4$;
$R^3$ is 1-6 independent substituents present at position(s) 1-6 of the aryl ring;
$R^1$ and $R^3$ are independently selected from acyl, alkyl, alkenyl, alkynyl, hydroxyalkyl, aminoalkyl, thioalkyl, aryl, aralkyl, carboxyaryl, alkoxyalkyl, alkoxyaryl, alcoxycarbonylaryl, aminoaryl, amidoaryl, haloaryl, heteroaryl, heteroaralkyl, carbocyclyl, heterocyclyl, heterocyclylalkyl, alkoxycarbonyl, alkylaminocarbonyl, alkylthiocarbonyl, sulfonate, alkylsulfonate, arylsulfonate, sulfone, alkylsulfone, arylsulfone, sulfoxide, alkylsulfoxide, arylsulfoxide, alkylsulfonamide, arylsulfonamide, and sulfonamide, piperidinyl, morpholinyl, pyrrolidinyl, phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzyl, benzofuryl, dibenzofuryl, benzthienyl, benzoxazolyl, benzothiazolyl, benzimidazolyl, pyridoimidazolyl, pyrimidoimidazolyl, pyridopyrazolyl, pyrazolopyrimidinyl, and any of which is optionally substituted with 1-6 independent substituents;
$R^2$ selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl; and
$R^4$ is absent or is selected from hydrogen and alkyl.

In certain embodiments, Z is S. In certain embodiments, X and Y are O. In certain other embodiments, X and Y are S. In certain other embodiments, X is S and Y is O. In certain other embodiments, X and Y are O and Z is S. In certain other embodiments, X, Y and Z are S. In certain other embodiments, X and Z are S and Y is O. In certain embodiments, U is N and V and W are $CR^4$. In certain such embodiments, $R^4$ is hydrogen. In certain other embodiments, V is N and U and W are $CR^4$. In certain such embodiments, $R^4$ is hydrogen. In certain other embodiments, W is N and V and V are $CR^4$. In certain such embodiments, $R^4$ is hydrogen. In certain embodiments, B is alkyl and A is absent. In certain such embodiments, $R^1$ is selected from alkoxycarbonyl, aryl, heteroaryl, carbocyclyl, heterocyclyl and alkoxycarbonyl. In certain embodiments, B is methylene and A is absent. In certain such embodiments, $R^1$ is selected from alkoxycarbonyl, aryl, heteroaryl, carbocyclyl, heterocyclyl and alkoxycarbonyl. In certain such embodiments, B is methylene and A is absent. In certain embodiments, where A is alkyl and B is absent, $R^1$ is alkoxycarbonyl. In certain embodiments, A and B are both absent. In certain such embodiments, $R^1$ is selected from alkoxycarbonyl, aryl, heteroaryl, carbocyclyl, heterocyclyl and alkoxycarbonyl. In certain embodiments, $R^1$ substituent is further substituted with 1-6 independent substituents. In certain embodiments, $R^1$ is selected from furan, phenyl, benzyl, tetrahydrofuran, tetrahydrothiophene, pyrrolidine, tetrahydropyran, tetrahydrothiopyran, piperidine, piperazine, and morpholine. In certain embodiments $R^1$ is selected from tetrahydrofuran, tetrahydrothiophene, and pyrrolidine, preferably tetrahydrofuran. In certain embodiments, $R^1$ is phenyl, preferably substituted phenyl. In certain such embodiments, $R^1$ is phenyl substituted one to five, preferably one to three, more preferably one or two times. In certain such embodiments, $R^1$ is phenyl substituted with one or two, preferably one substituent independently selected from halogen, nitro, cyano, hydroxyl, thiol, amino, alkoxy, alkylamino, alkylthio, hydroxyalkyl, alkoxyalkyl, aminoalkyl, thioalkyl, and alkyl, more preferably from alkyl and halogen, e.g., from methyl, fluoro and chloro. In certain embodiments, $R^2$ is selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, $R^3$ is selected from alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, $R^2$ is hydrogen and $R^3$ is selected from aryl, aralkyl, heteroaryl, heteroaralkyl, carbocyclyl, carbocyclylalkyl, heterocyclyl, and heterocyclylalkyl, preferably aryl, heteroaryl, carbocyclyl, and heterocyclyl. In certain embodiments, $R^3$ is heteroaryl selected from pyrrole, furan, pyrimidine, oxazole, isooxazole and thiophene, preferably furan. In certain embodiments, $R^3$ is furan substituted one to three, preferably one to two times, more preferably once. In certain such embodiments, $R^3$ is furan substituted once with a substituent selected from aryl, aralkyl, heteroaryl, heteroaralkyl, carbocyclyl, carbocyclylalkyl, heterocyclyl and heterocyclylalkyl, preferably aryl, heteroaryl, carbocyclyl, and heterocyclyl. In certain embodiments, $R^3$ is furan substituted once with an aryl group, which itself is optionally substituted, preferably one to two times with alkyl, carboxyl, alkoxycarbonyl and halogen, e.g., chlorophenyl, dichlorophenyl, carboxyphenyl. In certain embodiments, $R^3$ is aryl, preferably phenyl. In certain such embodiments, $R^3$ is phenyl substituted with one or two, preferably two substituents independently selected from halogen, nitro, cyano, hydroxyl, thiol, amino, alkoxy, alkylamino, alkylthio, hydroxyalkyl, alkoxyalkyl, aminoalkyl, thioalkyl, and alkyl. In certain such embodiments, $R^3$ is phenyl substituted once with a halogen, preferably bromo.

The compounds of the present invention can have an inherent end-to-end polarity such that compounds are more polar on one end of the molecule, for example on the top-end (N-substituted side of the thiazolidine ring) or the bottom-end (substituted furanyl side of the thiazolidine ring) as drawn, as compared to the other end of the molecule. Alternatively, compounds with two polar ends can be disfavored.

The compounds of the invention can be in a pure or substantially pure single configuration, such as a Z-configuration.

Certain compounds of the present invention can exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms can be present in a substituent such as an alkyl group. All such isomers, as well as mixtures thereof, are intended to be included in this invention.

One aspect of the invention relates to non-blocking ligands of β2 integrins. In one aspect, the β2 (b2) integrin is CD11b/CD18. Non-limiting examples of non-blocking ligands is CD40L, soluble CD40L (sCD40L), uPAR and soluble uPAR (suPAR). In one aspect, the non-blocking ligands of b2 integrins are integrin agonists, such that they activate b2 integrins. In a related aspect, the non-blocking ligands of b2 integrins activate b2 integrins and promote their binding to other ligands of b2 integrins. As an example, sCD40L can be used to promote activation of CD11b/CD18 and binding of CD11b/CD18 to fibrinogen, ICAM-1, uPAR and iC3b.

One aspect of the invention relates to compounds and methods that regulate binding of non-blocking ligands of β2 integrins to β2 integrins. In one aspect, the β2 (b2) integrin is CD11b/CD18. Non-limiting examples of non-blocking ligands is CD40L, soluble CD40L (sCD40L), uPAR and soluble uPAR (suPAR). In one aspect, the compounds of the present invention regulate the binding of the non-blocking ligands of CD11b/CD18, such as sCD40L and suPAR, to CD11b/CD18. In a related aspect, the regulation of binding of the non-blocking ligands of b2 integrins to b2 integrins by the compounds of this invention changes intracellular signaling in the b2 integrin expressing cells.

The present invention provides for a method of treating inflammation, by administering an effective amount of a β2 integrin agonist to a patient, and reducing inflammation. Preferably, the β2 integrin is CD11b/CD18. Inflammation can be reduced by reducing inflammatory cell migration and recruitment by increasing CD11b/CD18-mediated cell adhesion. The inflammatory cells can be macrophages, or any other cells that contribute to inflammation.

Inflammation can also be reduced by binding the β2 integrin agonist to an allosteric pocket in the αA-domain in CD11b. Such binding occurs without inducing global conformational changes in CD11b/CD18 and prevents outside-in signaling. The binding further induces priming of CD11b/CD18 and converts CD11b/CD18 into a stabilized intermediate conformation. The binding of the β2 integrin agonist preferably occurs with one or more residues within the E162-L170 sequence of CD11b, i.e. SEQ ID NO: 1 (EQLKKSKTL).

Treating inflammation can further include reducing mechanical vascular injury and preventing and reducing neointimal hyperplasia. Inflammation can also be reduced by accelerating degradation of MyD88, inducing faster dampening of TLR4-mediated pathways, and inducing Syk phosphorylation. Various pro-inflammatory factors can be upregulated or downregulated by the administration of the β2 integrin agonist. Factors that can be upregulated include hsa-miR-125b, hsa-miR-330-3p, hsa-miR-363, hsa-miR-134, hsa-miR-523, hsa-miR-1266, hsa-miR-15b*, hsa-miR-877*, hsa-miR-130b*, hsa-miR-1237, hsa-miR-26b*, hsa-miR-191*, and combinations thereof. Factors that can be downregulated include hsa-miR-181d, hsa-miR-151-3p, hsa-miR-526b, hsa-miR-199α-3p, hsa-miR-361-5p, hsa-miR-95, hsa-miR-551a, hsa-miR-365*, hsa-miR-1908, hsamiR-624*, hsa-miR-1913, hsa-miR-330-5p, hsa-miR-520d-3p, hsa-miR-224*, hsa-miR-505*, and combinations thereof.

The present invention also provides for a method of treating cancer, by administering an effective amount of a β2 integrin agonist to a patient, and reducing tumor growth. Reducing tumor growth can involve reducing incidence and size of metastases, reducing the rate of tumor regrowth, reducing the amount of inflammatory leukocytes, reducing tumor vascularization, reducing tumor engraftment, and combinations thereof. Reducing tumor growth can further involve reducing T-cell proliferation, decreasing IFN-g production by T-cells, reducing TNF-α release.

One aspect of the invention relates to compositions and methods of inducing an intermediate form of b2 integrins by binding of an integrin agonist to a b2 integrin. In particular, the present invention is directed towards CD11b/CD18, where binding of novel agonists of this invention induces an intermediate conformation of CD11b/CD18 on CD11b/CD18 expressing cells. Induction of the intermediate conformation leads to different type of intracellular signaling than the signaling that is induced upon integrin activation with protein ligands. The binding of an agonist of the invention to a b2 integrin can induce different intracellular signaling than binding of an activating antibody to a b2 integrin. Therefore, the present invention generally provides for a method of activating β2 integrins, by interacting the β2 integrin with an agonist, and stabilizing the b2 integrin in an intermediate affinity conformation.

The agonists and methods of the present invention can be used in combination with agents targeting Syk, Btk, JAK, JAK1, JAK2, JAK3 and their dosing can be increased or can be lowered in combination with the compounds of the present invention. Ant-clotting drugs, steroids, sphingosine-phosphate receptor modulators, and drug-eluting stent media can also be administered. Due to the synergy with any of these compounds, doses can be lowered and negative side effects can be reduced or eliminated associated with typical doses.

The agonists and methods of the present invention can be used in combination with anti-inflammatory drugs, such as, but not limited to, non-steroidal anti-inflammatory drugs (NSAIDS) such as salicylates (aspirin), acetic acid derivatives (indomethacin), propionic acid derivatives (ibuprofen or naproxen), or CoxII inhibitors such as celecoxib (CELEBREX®, Pfizer, Inc.) or rofecoxib (VIOXX®, Merck). Dosing is generally 10 to 3200 mg for anti-inflammatory drugs per day, which can be lowered in combination with the agonists of the present invention due to synergy of the combination. Furthermore, due to the synergy, side effects can be reduced that are associated with a typical dose of the anti-inflammatory drugs.

The agonists and methods of the present invention can be used in combination with anti-cancer compounds such as, but not limited to, cilengitide, a cyclo(RGDfV) peptide. Dosing can generally be 120 to 2400 mg/m$^2$, and can be lowered in combination with the compounds of the present invention due to synergy of the combination, therefore reducing side effects associated with a typical dose of the anti-cancer compounds.

The agonists and methods of the present invention can be used in combination with anti-rejection drugs, such as, but not limited to, tacrolimus, cyclosporine, and various steroids. Dosing for tacrolimus can be 0.25 mg to 1 mg per day and can be lowered in combination with the agonists of the present invention. Dosing for cyclosporine can be 1 to 12 mg/kg per day and can be lowered in combination with the agonists of the present invention due to synergy of the combination.

The agonists and methods of the present invention can be used in combination with anti-cancer treatments, such as chemotherapy, radiation, or surgery. Dosing of the anti-cancer treatments can be lowered in combination with the compounds of the present invention due to synergy of the combination, and therefore reducing side effects associated with typical dosing of these treatments. Compounds of the present invention can also be used as adjuvants to various anti-cancer treatments, such as chemotherapy, radiation and surgery. Compounds of the present invention reduce the growth of tumors, re-growth of tumors, tumor vascularization, recruitment of leukocytes in response to tumor cells or injury to tumors, tumor metastasis, tumor engraftment, and obesity and its response to tumors.

The agonists of the present invention can also be used to prevent radiation exposure induced injury in patients and cells. The present invention provides for a method of preventing effects of radiation, by administering an effective amount of a β2 integrin agonist to a patient prior to radiation exposure, and preventing the effects of radiation exposure on the patient.

The compounds of the present invention can also be used to mitigate the effects of radiation exposure. In particular, the compounds of the present invention can be administered to patients after the radiation exposure (delayed administration). The compounds of the present invention also protect various organs and compartments from radiation damage, including the hematopoietic system. Compounds of the present invention are effective radiomitigants and can be used under a delayed treatment scenario. Additionally, treatment with compounds of the present invention accelerates recovery of hematopoiesis and results in significant improvement in the recovery of HSC compartment after radiation exposure, including sublethal radiation. Therefore, the present invention provides for a method of treating a patient exposed to radiation, by administering an effective amount of a β2 integrin agonist to the patient after radiation exposure, and mitigating the effects of radiation exposure in the patient.

Acquired bone marrow failure (BMF) develops after an injury to the bone marrow (BM) by ionizing radiation (IR), chemotherapy drugs and antibiotics (e.g. busulfan and chloramphenicol), toxic chemicals (benzene, carbon tetrachloride), or viral infection (hepatitis, HIV, CMV, parvovirus) (1). Another form of acquired BMF called aplastic anemia is an immune-mediated BMF that develops after lymphocyte infusion, and is characterized by an immune-mediated functional impairment of hematopoietic stem cells (HSCs). The agonists of the present invention can also be used to prevent, mitigate or delay the development acquired BMF or reduce the amplitude of acquired BMF. Therefore, the present invention provides for a method of treating acquired bone marrow failure (BMF), by administering an effective amount of a β2 integrin agonist to a patient.

The agonists of the present invention can further be used for improving re-vascularization in patients with vascular wall damage. The present invention also provides for a method of improving the health of damaged vasculature in a patient by administering a β2 integrin agonist to the patient, and improving re-vascularization in the patient.

The present invention provides for a method of activating β2 integrins by interacting the β2 integrin with an agonist, preferably one of the compounds described herein. The compounds of the present invention can stabilize the b2 integrin in an intermediate affinity conformation.

The agonists can also correct or reduce the functional deficit in cells that express mutant forms of β2 integrins. For example, mutations in CD11b, such as the R77H mutation, have been linked to lupus and lupus nephritis. The agonists of the present invention can reduce or overcome the functional defects in cells, organisms, and animals that carry mutant forms of the β2 integrins. Therefore, diseases or conditions can be treated or prevented that are associated with the activity of β2 integrins, such as, diabetic nephropathy, lupus and lupus nephritis.

More specifically, the present invention provides for a method of treating nephropathy, by administering an effective amount of a β2 integrin agonist to a patient, and improving the health of the patient's kidneys. The nephropathy can be diabetic nephropathy. The health of the kidneys is improved by reducing the number of infiltrating leukocytes in the kidneys, preserving kidney function, and reducing glomerular damage and glomerular mesangial sclerosis.

The agonists of the present invention can also more generally modulate biological function in vitro or in vivo, such as, but not limited to, gene expression, epigenetic profile, protein expression, protein levels, protein modifications, post-translational modifications, and signaling. Preferably, the agonists of the invention modulate biological function in leukocytes, microglia and stem cells. Alternatively, the agonists of the invention can modulate biological function in other cells or tissues.

The agonists of the present invention can also modulate other biological functions in vitro or in vivo, such as, differentiation of stem cells, differentiation of pluripotent cells, maintenance of cells in culture or in long term storage, mobilization of cells, such as leukocytes from bone marrow into circulation or endothelial progenitor cells to sites of inflammation or injury and increasing retention of certain cells into their niches, such as leukemia cells in the marrow.

The treatment of the patient in any of the above methods can be confirmed by detecting the activation of the β2 integrins. This can be accomplished by taking a sample from the patient and performing an assay, such as detection of levels of β2 integrin expression on the surface of leukocytes in the biological sample or the level of activated β2 integrin on such cells. Another approach for confirming the treatment of a patient is to evaluate levels of the other known markers in the patient that are typically associated with the said disease, such as levels of IL-6 in the blood samples, or disease symptoms in the patient.

Computer-based modeling algorithms can be used to analyze the structures and conformations of agonists that bind β2 integrins, especially CD11b/CD18, to identify structural features that contribute to successful binding. Such information can be analyzed in conjunction with information about the structure or conformation of CD11b/CD18 or a binding pocket thereof, such as structural information obtained by analysis of CD11b/CD18 using analytical techniques such as x-ray crystallography or nuclear magnetic resonance, to analyze interactions between binding agonists and the binding pocket they interact with. Such analysis can be used to predict the portion of CD11b/CD18 that interacts with the agonist, to select agonists that possess structural features correlated with desired binding activity from a library of test agonists, or to design structures that are expected to exhibit binding with CD11b/CD18 for testing in vivo or in vitro using assays as described herein.

The computer-based modeling algorithms can also be used to identify novel agonists that bind β2 integrins, especially CD11b/CD18, using structural features of the chemical compound agonists of this invention. Scaffold hopping, atom replacement, residue replacement and/or molecule replacement methods can be used. The information can be analyzed in conjunction with information about the structure or conformation of CD11b/CD18 or a binding pocket thereof, such as structural information obtained by analysis of CD11b/CD18 using analytical techniques such as x-ray crystallography or nuclear magnetic resonance, to analyze interactions between binding agonists and the binding pocket they interact with. Such analysis can be used to predict the portion of CD11b/CD18 that interacts with the agonist, to select agonists that possess structural features correlated with desired binding activity from a library of test agonists, or to design structures that are expected to exhibit binding with CD11b/CD18 for testing in vivo or in vitro using assays as described herein.

A method of detecting or diagnosing a condition or disease in a patient is provided, by administering a β2 integrin agonist as described herein, detecting binding of the β2 integrin agonist to a β2 integrin, and confirming the presence of the disease. Preferably, the β2 integrin is CD11b/CD18. In other words, if binding is present, the patient has a disease as described above. For example, the disease can be an inflammatory disease or autoimmune disease, and by detecting the binding of the agonist to CD11b/CD18, it can be confirmed that a patient has those diseases. Also an agonist of the present invention can be administered to biological samples obtained from a patient in order to detect or diagnose a condition or a disease in a patient. The administered agonist can be derivatized, tagged, polymerized, encapsulated or embedded in such a way that it allows easy detection. The agonist can be tagged with a tracer, a radio-label or a fluorescent tag using a linker. The agonist can be detected using Magnetic Resonance Imaging (MRI) and other such diagnostic techniques as known in the art. Another method of detection can be as follows. A biological sample can be taken from a patient, such as blood or plasma, and an assay can be performed, such as to detect the binding of the β2 integrin agonist to the β2 integrin or measuring other markers (for example, IL-6 levels) in the sample.

The present invention also provides for a method of improving the general wellness of a patient by administering an effective amount of a β2 integrin agonist, and activating β2 integrins. In other words, by administering the agonists of the present invention, a patient's health and wellness improves because the agonists treat many different diseases as described above.

The dosage of the agonists and/or compositions of the invention can vary depending on many factors such as the pharmacodynamic properties of the agonist, the mode of administration, the age, health and weight of the recipient, the nature and extent of the symptoms, the frequency of the treatment and the type of concurrent treatment, if any, and the clearance rate of the agonist in the animal to be treated. One of skill in the art can determine the appropriate dosage based on the above factors. The agonists of the invention can be administered initially in a suitable dosage that can be adjusted as required, depending on the clinical response.

The newly described small molecule agonists (termed "leukadherins") activate CD11b/CD18 by binding to the integrin's ligand-binding αA domain (also known as the CD11bA-domain and the aI-domain [54]), an approximately 200 amino acid von Willebrand factor type A (VWFA)

domain in the CD11b chain. Modeling studies showed that leukadherins bind to an allosteric pocket in the αA domain, shifting the equilibrium to its more active conformation, thereby promoting ligand engagement by CD11b/CD18 [55]. Leukadherin-mediated integrin activation increases CD11b/CD18-dependent adhesion of leukocytes, which leads to a significant reduction in their migration in vitro and in vivo and results in a significant decrease in inflammatory injury. A number of monoclonal antibodies (mAbs) that activate CD11b/CD18 and other b2 integrins or that bind in an activation-sensitive manner (together referred to as "activating mAbs") have also been previously described in the literature [56-65]. KIM127 is an activation-dependent antibody that also activates human CD11b/CD18 by recognizing sites in the CD18 EGF2 domain that are buried in the inactive integrin conformation [57, 61, 66]. Antibody 24 (mAb 24) detects and stabilizes the ligand-bound active conformation of human b2 integrins and recognizes an activation-sensitive epitope in the CD18 A-domain (αA domain) [59]. Similarly, activating antibodies against murine and rat b2 integrins have also been described in the literature. M18/2 recognizes the murine CD18 chain and simulates CD11b/CD18-dependent cell adhesion and rosetting [67-69]. The anti-rat CD11b antibodies ED7 and ED8 enhance CD11b/CD18-dependent granulocyte adhesion and homotypic aggregation, suggesting that they activate CD11b/CD18 [70].

As a therapeutic agent, the small molecule compounds and the antibody-based biologics each have distinct advantages and disadvantages. While small molecules are easily delivered (typically orally), they are rapidly cleared and require frequent dosing, although the oral route of administration makes it an easy process. The route of administration of antibody-based biological agents is less than desirable, as they are typically injected intravenously into the circulation, although their long in vivo half-life means that they need to be typically administered weekly or every other week. However, this delayed clearance of antibody-based biologics is also a liability, in case they lead to serious side effects, as the side effects take a much longer time to subside. Additionally, biologics have the potential to develop an immune response against them, generating new complications in the treated patients. Having established that CD11b/CD18 activation is a novel and pharmacologically useful mechanism for the development of anti-inflammatory therapeutics, we wondered if both types of integrin agonists—small molecule based chemical compounds and the antibody based biologics—would be equally effective and reasonable to use in vivo to treat inflammation via this mechanism of action (MOA). To address this question, a head-to-head testing was performed of the two types of agents using the newly developed leukadherins compounds and a number of anti-CD11b/CD18 activating antibodies that are widely available.

Here, the findings are reported that indeed CD11b/CD18 activation via both types of reagents (the chemical leukadherins and the biologic activating mAbs) increases integrin-mediated cell adhesion and decreases cell migration and wound healing in vitro, showing that both types of agents have a similar mechanism of action. However, it is also shown that while leukadherins do not induce CD11b/CD18 clustering on cell surface or intracellular signaling pathways in the treated cells, the activating antibodies produced significant CD11b/CD18 clustering and increased phosphorylation of key intracellular signaling proteins. This shows that unlike the binding with leukadherins, engagement of CD11b/CD18 with activating mAbs mimics a ligand-bound state and induces significant outside-in signaling. Further mechanistic investigations using conformation-specific probes showed that leukadherin binding did not induce large global conformational changes in CD11b/CD18 that are typically associated with binding of ligands or activating antibodies [28, 71, 72]. This explains the lack of ligand-mimetic outside-in signaling by leukadherins. Finally, in a head-to-head comparison in a vascular injury model in vivo, while both LA1 and ED7 similarly and significantly reduced the influx of macrophages into the injured arteries, only leukadherin LA1 dose-dependently reduced vascular injury and showed significantly higher efficacy than the anti-CD11b activating antibody ED7. The results show that these small molecule agonists of CD11b/CD18 have a clear therapeutic advantage over the biologic activating antibody. Together, the data presented here show that small molecule agonists of CD11b/CD18 have significant advantages over biological agonists, which can require significant optimization before biologic agonists can be used in vivo to take advantage of this new mechanism of action for the development of novel anti-inflammatory therapeutics. Thus, leukadherins represent a preferred class of agents for development into future anti-inflammatory therapeutics.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include; U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Methods of Synthesis.

Compounds of the present invention may be readily synthesized using techniques known to those skilled in the art, such described, for example, in Advanced Organic Chemistry. March, 4th Ed., John Wiley and Sons, New York, N.Y., 1992; Advanced Organic Chemistry, Carey and Sundberg, Vol. A and B, 3rd Ed., Plenum Press, Inc., New York, N.Y., 1990; Protective groups in Organic Synthesis, Green and Wuts, 2"d Ed., John Wiley and Sons, New York, N.Y., 1991; Comprehensive Organic Transformations, Larock, VCH Publishers, Inc., New York, N.Y., 1988 and references cited therein. The starting materials for the compounds described in this invention may be prepared using standard synthetic transformations of chemical precursors that are readily available from commercial sources, such as, Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Arcos, (Pittsburgh, Pa.) and Trans World Chemicals (Rockville, Md.).

Material and Methods, Reagents, and Antibodies.

The anti-CD11b monoclonal antibody (mAb) 44a (an immunoglobulin G (IgG) 2a (IgG2a) isotype) [73], the heterodimer-specific mAb 1B4 (IgG2a) [74, 75], the activating anti-CD18 mAb KIM127 (IgG1) [61] and the anti-CD11b mAb ED8 (IgG1) [76] were from ATCC. The activating anti-CD18 mAb 24 (IgG1) [59] was obtained from Abcam, the activating anti-CD11b mAb ED7 (IgG1) [76] was from Sigma-Aldrich, the activating anti-CD18 mAb M18/2 (IgG2a) [67] was from ebiosciences, the blocking anti-CD11b mAb OX42 (IgG2a) [77] was obtained from Millipore and the isotype control antibodies clone X40 (IgG1) and clone X39 (IgG2a), fluorescein isothiocyanate (FITC)-conjugated mAb A85-1 (rat anti-mouse IgG1), FITC-conjugated R19-15 (rat anti-mouse IgG2a), FITC-conjugated goat antibody against mouse immunoglobulin, rat antibody against mouse GR-1 (GR1-FITC), and phycoerythrin (PE)-conjugated rat antibody against mouse CD11b were obtained from BD Pharmingen. M1/70, a rat mAb against mouse CD11b (IgG2b) [78] was from the monoclonal antibody core at University of California, San Francisco (UCSF). Human fibrinogen (depleted of plasminogen, von Willebrand factor, and fibronectin) was from Enzyme Research Laboratories, bovine serum albumin (BSA) was from Sigma, LPS (O111:B4) was from Invivogen, and phorbol-12-myristate-13-acetate (PMA) was from Cell Signaling. Maxisorp and Highbind 384-well plates were obtained from Nalgene and Corning, respectively. Non-fat milk was obtained from BioRad. All cell culture reagents were from Invitrogen Corp. and Mediatech. Fetal bovine serum (FBS) was purchased from Atlanta Biologicals, Inc. The antibiotic G418 was purchased from Invivogen.

The wild type Sprague-Dawley (SD) rats were purchased from Harlan Laboratories. Animal care and procedures were approved by the Institutional Animal Care and Use Committee (IACUC) and were performed in accordance with institutional guidelines.

Cells and Cell Lines.

K562 cells stably transfected with plasmid encoding wild-type integrin CD11b/CD18 (K562 WT cells) have been described previously [49, 79] and were maintained in Iscove's Modified Dulbecco's Medium (IMDM) supplemented with 10% FBS and G418 (0.5 mg/ml). The murine macrophage cell line (RAW 264.7 cells) was obtained from ATCC and the cells were maintained in DMEM supplemented with 10% heat-inactivated FBS according to the manufacturer's instructions. The primary rat peritoneal macrophages were isolated from the wild type Fisher 344 rats that had been previously injected with 5 mL of Brewer's thioglycolate broth (Sigma-Aldrich). Macrophage purity was directly analyzed by single channel flow cytometry using rat macrophage specific monoclonal antibodies ED1 (AbD Serotec, Raleigh, N.C.), WT.5 (BD Biosciences) and His36 (BD Biosciences). Purity was typically >85%. Macrophages were used in assays immediately upon isolation.

Cell Adhesion Assays.

Cell adhesion assays using K562 WT, murine RAW 264.7 cells and the primary rat macrophages were performed as previously described and used immobilized fibrinogen as the ligand of CD11b/CD18 [49]. A stock solution of the leukadherin family of small-molecule agonists LA1, LA2, and L15 was prepared by dissolving each compound in DMSO at a concentration of 10 mM. The final concentration of DMSO in the assay was approximately 1%. Cells were suspended in serum-free DMEM and incubated in the presence of various agents in ligand-coated wells in a 384-well plate for 10 minutes at 37° C. LA1, LA2, and LA15 were used at a final concentration of 15 µM each and the mAbs were used at a final concentration of 20 □g/mL each in the assays (LA2 and LA15 are shown in FIG. 10). The assay plates were then gently inverted and kept in the inverted position for 30 minutes at room temperature to dislodge the nonadherent cells. The remaining adherent cells were fixed using 4% formaldehyde and quantified by imaging microscopy as previously described (22, 63). Assays were performed in triplicate wells. Data reported are from one of at least three independent experiments.

Wound Healing Assay.

Murine RAW 264.7 macrophage cells were grown in DMEM 10% FBS medium in T75 flasks to 70% confluence. The cells were detached by trypsin treatment for 10 minutes at 37° C. and evenly reseeded in 24 well plates and allowed to attain >70% confluency. A scratch was introduced horizontally across the well using 200 □L tip applying even force throughout the well and holding the tip at approximately an 80 degree angle. The wells were subsequently washed and fresh medium containing various treatment groups was introduced. The wound was imaged using 10× objective. The cells were allowed to grow for 48 hours and the wound was reimaged at the same field after 48 hours. The average extent of wound closure was evaluated by measuring the width of the wound. The area healed was analyzed using ImageJ software and is expressed as percentage healing after 48 hours.

Immunofluorescence Microscopy.

To examine localization and clustering of CD11b/CD18 on the cell surface, 1×104 K562 CD11b/CD18 cells were suspended in serum-free IMDM and incubated in the presence of control DMSO (1%), leukadherins LA1, LA2, or LA15 (15 µM each), mAb KIM127 (1:100 dilution of ascites), mAb 24 (20 □g/mL) or Mn2+ (1 mM) for 1 hour at 37° C., as described previously [55, 72]. To visualize changes upon ligand binding, fibrinogen (50 µg/mL) was also added to the cell suspension media in a second set of incubations. The cells were fixed in suspension and incubated with mAb 184, which is specific for CD11b/CD18, followed by Alexa Fluor 488-conjugated goat antibody against mouse Ig (Sigma). Fluorescence images were recorded with a Leica DMI16000 deconvolution microscope using an HCX APO 40×/0.75 DRY objective with a DCF360FX camera and with Leica LAS-AF software. A 3-dimensional representation of CD11b/CD18 fluorescence intensity and the analysis of the number of CD11b/CD18 clusters per cell was performed using ImageJ software as described [80]. Clustering determination was carried out by counting individual fluorescent peaks that were projected from the basal to the apical side of the cell and were at least 50% above the base line levels. The images presented are representative of at least 20 cells analyzed for each condition from at least three independent experiments.

Western Blotting Analysis.

K562 WT cells were incubated with LA1, LA2, LA15 (15 µM), or fibrinogen (200 µg) in serum-free medium for 1 hour at 37° C. Cell lysates were resolved on 4-12% NuPAGE Bis-Tris SDS-PAGE gels using MES running buffer and transferred to a polyvinylidene difluoride (PVDF) membrane (ThermoScientific) using established protocols. Membranes were incubated with a 1:1,000 dilution of the anti-phospho-protein antibodies (anti phospho-p44/42 MAPK (pERK1/2) antibody (Thr202/Tyr204, Cell Signaling) or anti-phospho-SAPK/JNK (pJNK) antibody (Thr183/Tyr185, Cell Signaling #81E11)), or with an antibody against either total ERK1/2 (p44/42 MARK (Erk1/2), Cell Signaling #137F5) or total JNK (SAPK/JNK, Cell Signaling #56G8) and developed according to the manufacturer's instructions (ThermoScientific). Proteins were quantified by densitometry using ImageJ software. Data presented are representative of two to three independent experiments.

Flow Cytometry.

Flow cytometric analyses of K562 WT cells were performed according to published protocols [55, 57, 81]. Briefly, cells were suspended in the assay buffer (Tris-buffered saline (TBS) containing 1 mM of ions Ca2+ and/or Mg2+ and 0.1% BSA). Cells (5×105) were incubated with primary mAb (1:100 dilution of IB4 ascites or the isotype controls, 1:50 dilution of KIM127 ascites or 15 □g/mL of mAb 24) in 100 DL buffer in the absence or presence of 20 □M agonist LA1 on ice (except for mAbs KIM127 and 24 and the relevant isotype controls, where incubations were performed at 37 □C) for 30 minutes. Subsequently, the cells were washed three times with the assay buffer and incubated with goat anti-mouse-APC (1 □g/ml, Invitrogen) for 20 minutes at 4° C. Cells were washed twice with the assay buffer and analyzed using FACSCaliber flow cytometer (BD Biosciences, CA), counting at least 10,000 events. Data was analyzed using the CellQuest software (BD Biosciences). Data shown is from one of at least three independent experiments.

Balloon-Induced Arterial Injury in Rats.

All surgeries were performed under anesthesia by isoflurane (Baxter). Activating mAb ED7 (4 mg/kg/d), the isotype control mIgG1 (4 mg/kg/d, Rockland) and the leukadherin LA1 (1 mg/kg/d) were each administered intra peritoneally (i.p.) in saline daily until the end of the experiment. Balloon injury in the right iliac artery was inflicted with a 2F Fogarty catheter (Baxter) adapted to a custom angiographic kit (Boston Scientific, Scimed) [82]. An aortotomy in the abdominal aorta was made to insert a catheter to the level of the right iliac artery. The balloon was inflated to 1.5 to 1.6 atmospheres and retracted to the arteriotomy site three times. The aortic excision was repaired with eight sutures. The abdominal cavity was closed by planes with an interrupted suture pattern. Arterial specimens were collected 21 days after injury and fixed in 4% formalin-PBS (Sigma-Aldrich) for 5 minutes and analyzed by histology and immunostaining. Neointima were measured in H&E stained slides using ImagePro.

Flow cytometric analyses for quantitation of arterial macrophages in injured arteries.

Agonist treated and control balloon-injured Fisher 344 rats were sacrificed 7 days post surgery at the onset of inflammation. The injured and non-injured iliac arteries were microdissected and digested with Collagenase/Elastase mix (Worthington Biochemical, NY) in DMEM containing 2% FBS for 2 hours at 37° C. The resulting single cell suspension was washed with cold PBS containing 2% FBS and filtered through 70 □M sieve. Cells were re-suspended cold PBS containing 2% FBS at a concentration of 106 cells per 100 µl and stained with biotinylated anti-rat CD11b antibody (clone WT.5, BD Biosciences) for 1 hour at 4° C. Subsequently, cells were washed and incubated with APC-Streptavidin for 30 minutes at 4° C. Stained cells were fixed with formalin 4% in PBS for 10 minutes. Cells were washed twice with the assay buffer and analyzed using FACS II Canto cytometer and the data were analyzed using FlowJo (Tree Star Inc.) software. Data presented is from 4-6 independent samples/group.

Statistical Analysis.

Data were analyzed with GraphPad Prism and compared with the Student's t test or by one-way analysis of variance (ANOVA) with posthoc analysis, where appropriate. P<0.05 was considered statistically significant.

Flow Chamber Assay.

The flow chamber assay was performed as described in literature (Chen, J. F., Salas, A. & Springer, T. A. Bistable regulation of integrin adhesiveness by a bipolar metal ion cluster. *Nat. Struct. Biol.* 10, 995-1001 (2003)). A polystyrene Petri dish was coated with a 5 mm diameter, 20 μL spot of 20 μg/mL purified h-ICAM-1/Fc (R&D) or 20 μg/mL Fibrinogen in coating buffer (PBS, 10 mM $NaHCO_3$, pH 9.0) for 1 hour at 37° C., followed by 2% BSA in coating buffer for 1 hour at 37° C. to block nonspecific binding sites. Transient transfected 293T cells were washed twice with wash buffer (20 mM Hepes, 150 mM NaCl, pH 7.4, 5 mM EDTA/0.5% BSA), subsequently once with HBS containing 1 mM $Ca^{2+}$ and 1 mM $Mg^{2+}$ ($HBS^{++}$), and finally resuspended at the concentration of $5\times10^6$/mL in $HBS^{++}$ ($Ca^{2+}$ and $Mg^{2+}$-free HBS, 0.5% BSA) and kept on ice. Cells were incubated in 2% DMSO with or without 25 μM LA1 at 37° C. for 30 minutes. And subsequently infused in the flow chamber using a Harvard apparatus programmable syringe pump. Cells were allowed to settle down for 5 minutes, and accumulate for 30 seconds at 0.3 $dyn/cm^2$ and 10 seconds at 0.4 $dyn/cm^2$. Then, shear stress was increased every 10 seconds from 1 $dyn/cm^2$ up to 32 $dyn/cm^2$, in 2-fold increments. The number of cells remaining abound at the end of each 10-sec interval were determined. Rolling velocity at each shear stress was calculated from the average distance traveled by rolling cells in 3 seconds. Rolling adherent cells were defined with a velocity more than 1 μm/s. Adhesive behavior of vehicle-, $Mn^{2+}$ or LA-treated CD11b/CD18 transfectants under the wall shear stress is shown.

Results

Integrin agonists have several advantages over antagonists. Research with antagonists over last several years has shown them to be suboptimal. First, it has been showed that suppressing leukocyte recruitment with antagonists requires occupancy of >90% of active integrin receptors [2], usually requiring high levels of blocking antibodies in vivo. Second, complete blockade of cell surface-expressed CD11b/CD18 even with antibodies is difficult due to availability of a large mobilizable intracellular pool of CD11b/CD18 [30, 31]. Third, several other antagonists, such as ligand-mimetic neutrophil inhibitory factor (NIF) [67] and recombinant αA-domain [68], were effective in animal models but their large size and immunogenicity preclude their use as a therapeutic agent. Recombinant NIF (UK-279276) failed in clinical trials. Likewise, peptides derived from either anti-CD11b/CD18 antibodies or CD11b/CD18 ligands are not very efficacious in blocking ligand binding in vitro [69], perhaps owing to their improper conformation in solution or to their small size relative to the ligand-binding region on CD11b/CD18. Finally, many antagonistic antibodies (such as rhuMAb CD18, anti-CD18 LeukArrest (Hu23F2G) and anti-ICAM1 mAb Enlimomab (R6.5)) failed in treating inflammatory/autoimmune diseases in several clinical trials [28, 29] and β2 integrin blockers have also shown unexpected side effects and have had to be withdrawn from the market [33].

Chemical and biological agonists of integrin CD11b/CD18 enhance cell adhesion. It was proposed that integrin activation could be a novel mechanism for the development of next-generation anti-inflammatory therapeutics that reduce inflammatory cell migration and recruitment by enhancing, rather than reducing, cell adhesion [49, 55]. To that end, Applicant recently described novel small molecule agonists of CD11b/CD18, which Applicant termed leukadherins [55], that Applicant identified using a cell-based high-throughput screening assay [49, 50]. Leukadherin-1 (LA1) showed high-affinity for CD11b/CD18 and increased cell adhesion by binding to an allosteric pocket of the ligand-binding αA-domain (also known as aI-domain) of CD11b and stabilizing it in an active form [55—see FIG. 1B]. Applicant also identified additional analogs of LA1 that showed similar activity (including LA2 and LA15, FIG. 10). Similarly, a number of biological agonists of CD11b/CD18 (and other b2 integrins), in the form of activating antibodies, have been developed over the years by others, including anti-CD18 monoclonal antibody (mAb) KIM127 [83] and anti-CD18 mAb 24 [59].

Figure 11:
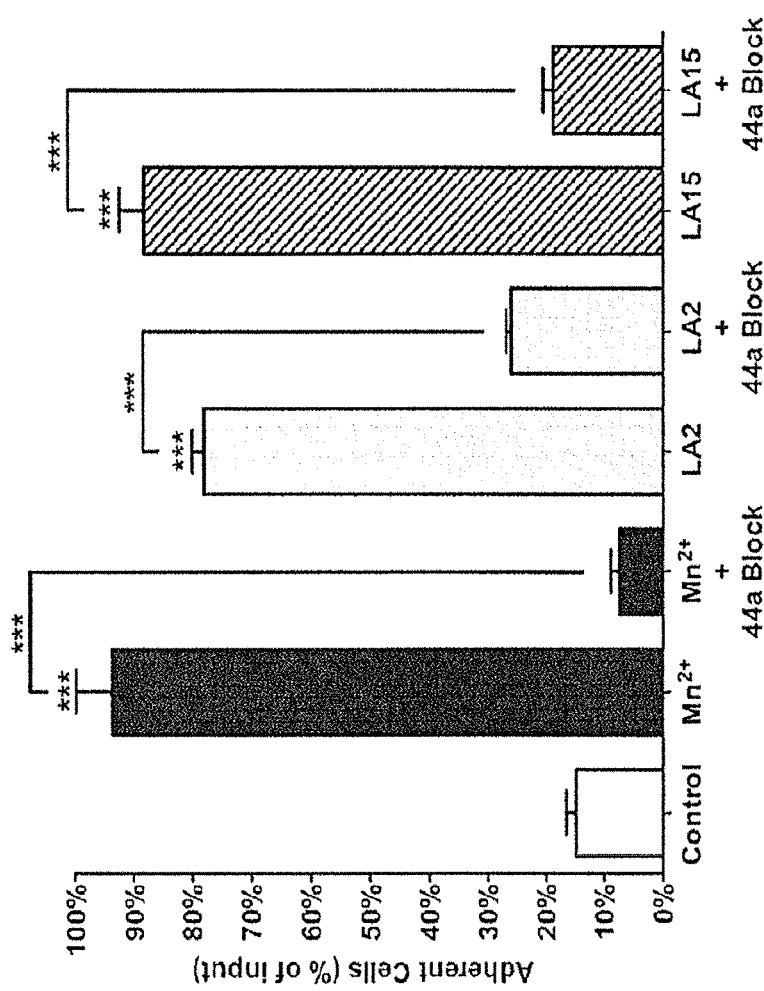
FIG. 11 is a histogram showing that cells expressing CD11b/CD18 show increased adhesion in the presence of leukadherins.

To determine how the two types of agonists—chemical (LA1) and biological (mAbs KIM127 and 24)—affect ligand binding by CD11b/CD18, a head-to-head comparison was performed of LA1, mAb KIM127, and mAb 24 for their relative abilities to increase adhesion of CD11b/CD18 to immobilized physiologic ligand fibrinogen using K562 cells stably expressing wild type CD11b/CD18 (K562 WT). K562 WT cells constitutively express wild type CD11b/CD18 in a low affinity state (as in normal leukocytes) [66, 79], thus, providing an excellent system to examine the level of integrin activation afforded by various agents [55, 66]. K562 WT showed minimal adhesion to immobilized fibrinogen in the presence of physiologic divalent cations (Ca2+ plus Mg2+, each at 1 mM). The known non-selective integrin activator Mn2+ [84, 85] significantly enhanced cell adhesion, increasing it to a maximal level, which was significantly blocked to basal levels by a blocking anti-CD11b antibody 44a that binds to the αA-domain [73]. Similarly, agonists LA1 and activating mAbs KIM127 and 24 significantly increased K562 WT cell adhesion to immobilized fibrinogen, as compared to the basal Ca2+ plus Mg2+ condition. However, it was found that agonist mAb 24 produced a lower increase in the level of cell adhesion as compared to the other two agonists—LA1 and KIM127. In all cases, the adhesion of K562 WT to immobilized fibrinogen was also significantly reduced by the anti-CD11b blocking mAb 44a, further confirming that the increased cell adhesion by all of these agonists was mediated by CD11b/CD18. As Applicant has shown before, this agonistic effect of leukadherins is not limited to a single compound, as additional leukadherins LA2 and LA15 similarly enhanced CD11b/CD18-mediated cell adhesion (FIG. 11). FIG. 11 is a histogram showing percentage adhesion of K562 WT cells to immobilized fibrinogen in the presence of physiologic 1 mM $Ca^{2+}$ and 1 mM $Mg^{2+}$ ions (Control), the non-selective integrin agonist $Mn^{2+}$ (1 mM), or the agonists LA2 (15 μM) and LA15 (15 μM) in the absence or presence of blocking anti-CD11b antibody 44a (1:100 dilution of ascites fluid). Data shown are mean±the standard error of the mean (SEM) (n=3 to 6 replicates per condition) and are from one of at least three independent experiments. ***p<0.0001.

Next, to examine if the chemical and biological agonists of CD11b/CD18 have a similar effect on ligand binding by CD11b/CD18 from different species, the murine macrophage cell line RAW 264.7 and the primary rat macrophages that have constitutive CD11b/CD18 surface expression were used. The small molecule compound LA1 binds to an allosteric pocket in the αA-domain of CD11b (referred to as Socket for Isoleucine (SILEN) [86] in CD11b or IDAS in CD11a [87]) that is highly conserved across various species [88], suggesting that LA1 should be able to activate CD11b/CD18 from various species. However, the biological agonists (e.g.; activating mAbs) are highly species-selective. Therefore, a well-characterized anti-mouse activating antibody (M1812) [67] was used with the murine RAW 264.7 cells and the anti-rat anti-CD11b activating antibody ED7 [70, 76] was used with the primary rat macrophages. The anti-mouse CD18 mAb M18/2 is a non-blocking antibody that has been reported to simulate CD11b/CD18-dependent cell adhesion and rosetting [67-69]. The anti-rat CD11b antibodies ED7 (and another mAb ED8) have been shown to enhance CD11b/CD18-dependent granulocyte adhesion and homotypic aggregation under certain conditions, suggesting that they activate CD11b/CD18 [70].

The RAW 264.7 cells showed minimal level of adhesion to immobilized fibrinogen in the presence of physiologic 1 mM Ca2+ and Mg2+, which significantly increased (to maximal levels) with the agonist Mn2+. As with K562 WT cells, agonists LA1 and the activating mAb (M18/2) significantly and similarly increased the level of cell adhesion, as compared to the basal condition. Furthermore, in both cases, addition of blocking anti-CD11b mAb M1/70 [78] eliminated the increase in cell-adhesion due to the two agonists, again confirming that CD11b/CD18 mediated the increased cell adhesion by both types of agonists. Similarly, the primary rat macrophages showed almost no adhesion to immobilized fibrinogen in the presence of non-activating, physiologic Ca2+ and Mg2+ ions, but bound significantly more upon activation with Mn2+. Again, both types of agonists—the chemical LA1 and the activating mAb ED7—significantly enhanced the level of macrophage adhesion as well, as compared to the non-activating condition, and, in both cases, addition of blocking anti-CD11b mAb OX42 [77] greatly reduced the effects of the two agonists, confirming that the increased rat macrophage cell adhesion by both agonists was mediated by CD11b/CD18. Surprisingly, ED8, which has been reported as an agonist similar to ED7 and having an overlapping epitope with ED7 [70, 76], did not produce any significant enhancement in the adhesion of the primary rat macrophages to immobilized fibrinogen (data not shown), showing that ED7 is a stronger agonist than ED8. Taken together, these results show that selective agonists of the integrin CD11b/CD18, be it chemical or biological, enhance CD11b/CD18-dependent cell adhesion. Additionally, it shows that while biologics have strong species dependence, leukadherins are equally effective on human, murine and rat CD11b/CD18.

Activation of CD11b/CD18 Reduces Macrophage Cell Migration and Wound-Healing.

Wound-healing assays are routinely used as a classic method for studying cell migration and to assess the effects of various perturbations of the underlying biological processes on such a key cellular function [89, 90]. Macrophages play a significant role in wound-healing [91] and confluent monolayers of macrophages, when artificially wounded or scratched with a pipette tip, respond to the disruption of cell-cell contacts by healing the wound through a combination of proliferation and migration [89]. Macrophages and other leukocytes use CD11b/CD18 dependent cell adhesion (as well as other b2 integrins) to migrate over two-dimensional surfaces [92]. Applicant has previously shown that CD11b/CD18 agonist LA1, by freezing integrin in a ligand-bound state, impairs neutrophil chemotaxis [55]. However, how LA1 compares to a biological agonist of the integrin CD11b/CD18 in a head-to-head comparison is not known.

Here, a murine macrophage cell-based wound-healing assay was used to compare the relative efficacy of LA1 with a biological agonist of CD11b/CD18 (the anti-CD18 activating mAb M18/2) using the RAW 264.7 cells [93]. The RAW 264.7 cells were plated to confluence and the cells were 'wounded' by scraping a marked location on the plate with a pipette tip.

Figure 4A:
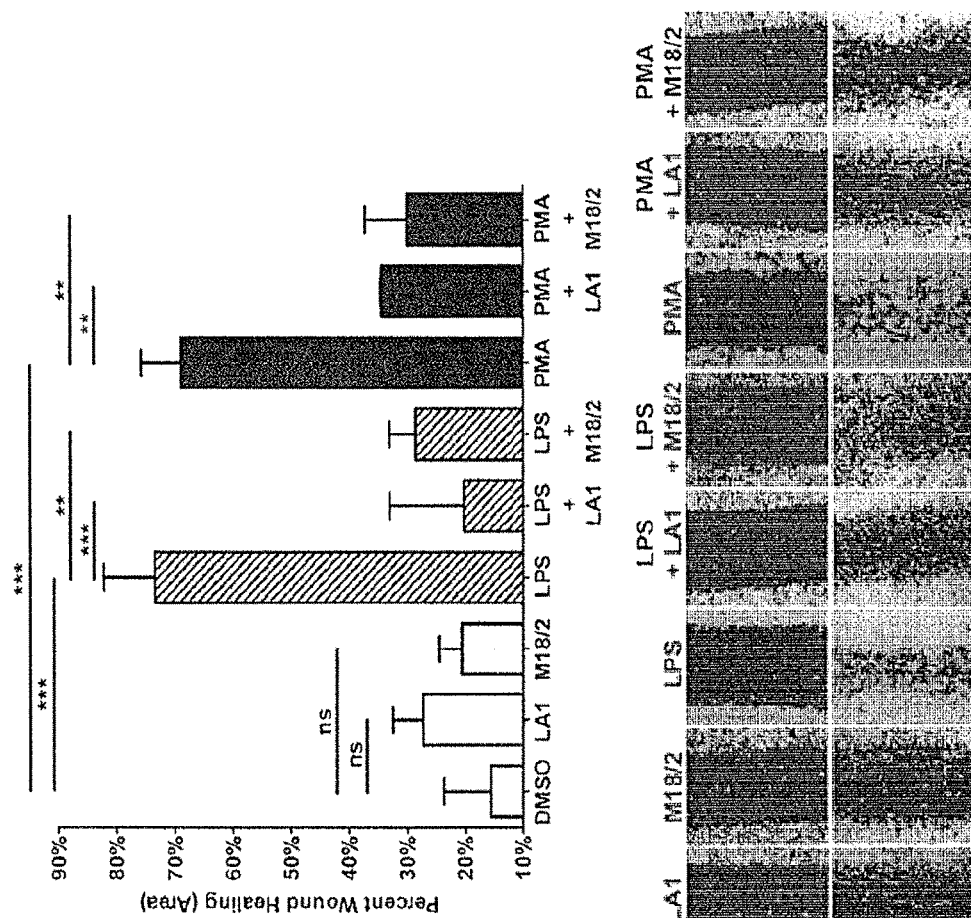
FIGS. 4A-4B show that increasing macrophage adhesion decreases cell migration and in vitro wound healing.
Figure 4B:
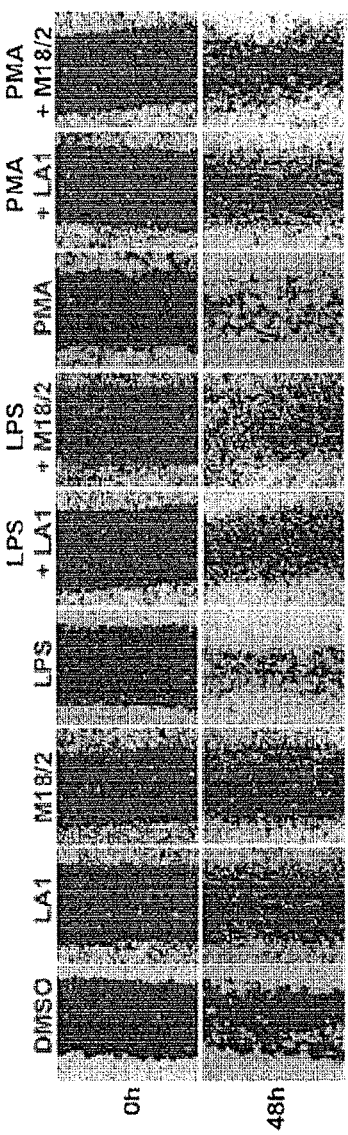

As shown in FIGS. 4A and 4B, stimulation with either lipopolysaccharide (LPS) or with the phorbol ester phorbol-12-myristate-13-acetate (PMA) significantly induced the migration of macrophages back into the wound area, as compared to the unstimulated cells (DMSO). The plot in FIG. 4A shows percentage of wound area that is healed via migration of RAW 264.7 macrophages into the wound under various conditions 48 hours after the pipette tip induced injury. p<0.001, *p<0.0001, ns=not significant. For FIG. 4B, RAW 264.7 cells were plated in 24-well tissue culture plates ($2 \times 10^6$ cells/well) and allowed to adhere in complete media for 12 hours. The cell monolayers were treated with vehicle (DMSO, agonist LA1 (15 □M), activating antibody M18/2 (20 □g/mL) and with LPS (100 ng/mL) or PMA (100 nM) that accelerate cell migration and wound-healing, for 1 hour prior to wounding with a pipette tip. Furthermore, cell monolayers in additional wells were treated with LPS (100 ng/mL) or PMA (100 nM) in the presence of LA1 (15 □M) or M18/2 (20 □g/mL) to investigate whether increasing CD11b/CD18-dependent cell adhesion will impact the wound-healing process under these conditions. Subsequently, the wounded monolayer cell cultures were incubated for 48 hours. Images of the cells in culture were obtained immediately prior to (0 hours) and after the completion of the experiment (48 hours) using an inverted phase contrast microscope attached to a video camera.

Figure 12:
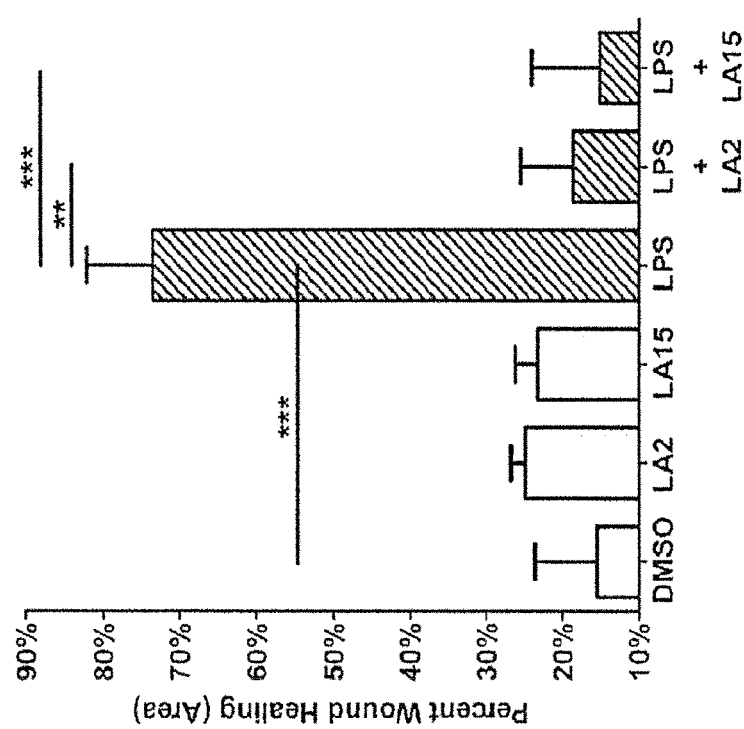
FIG. 12 is a histogram showing increasing macrophage adhesion with leukadherins decreases cell migration and in vitro wound healing.

Expectedly, treatment with the agonists LA1 and M18/2 alone showed no significant increase in the migration of macrophages into the wound area, as compared to unstimulated cells (DMSO). However, both CD11b/CD18 agonists significantly, and to a similar extent, reduced the migration of LPS- or PMA-stimulated macrophages. Additionally, the compounds LA2 and LA15 similarly reduced the migration of LPS-stimulated macrophages (FIG. 12), showing that the leukadherins family of compounds has a similar effect on macrophage migration. FIG. 12 is a histogram showing percentage of wound area that is healed via migration of RAW 264.7 macrophages into the wound under various conditions 48 hours after the pipette tip induced injury. RAW 264.7 cells were plated in 24-well tissue culture plates ($2 \times 10^6$ cells/well) and allowed to adhere in complete media for 12 hours. The cell monolayers were treated with vehicle (DMSO), agonist LA2 (15 □M), or agonist LA15 (15 □M) and with LPS (100 ng/mL) for 1 hour prior to wounding with a pipette tip. Furthermore, cell monolayers in additional wells were treated with LPS (100 ng/mL) in the presence of LA2 (15 □M) or LA15 (15 □M) to investigate whether increasing CD11b/CD18-dependent cell adhesion will impact the wound-healing process under these conditions. Subsequently, the wounded monolayer cell cultures were incubated for 48 hours. Images of the cells in culture were obtained immediately prior to (0 hours) and after the completion of the experiment (48 hours) using an inverted phase contrast microscope attached to a video camera and quantitated with ImageJ. Representative data shown here are from a triplicate well experiment from one of at least two to three independent experiments. p<0.001, *p<0.0001.

These results show that integrin CD11b/CD18 activation via either type of agonist equally impairs the migratory capacity of macrophages.

Activating Antibodies, but not LA1, Induce Integrin Clustering and Intracellular Signaling.

Next, it was evaluated if there were any significant differences in the integrin binding mediated signaling that is induced by the two types of agonists. While the activating antibodies and leukadherins both enhance CD11b/CD18-dependent cell adhesion and reduce cell migration, it is possible that integrin activation can induce undesirable intracellular signaling, such as those that have been described for the integrin antagonists, which can limit their effectiveness and utility in the clinic [94-100]. For example, aIIbb3 and aVb3 antagonists induce outside-in signaling [94, 96]. Similarly, CD11b/CD18 ligation with ligands or blocking antibodies induces CD11b/CD18 clustering [28] and outside-in signaling via activation and phosphorylation of mitogen activated protein kinases (MAPKs), including the c-Jun NH2-terminal kinase (JNK), the p38 MAPK and the extracellular signal-regulated kinase (ERK) [28, 33, 71, 101], thereby up-regulating the pro-inflammatory NF-kB signaling [29, 32, 102]. Additionally, both inactive and active CD11b/CD18 can be induced to form macro clusters, but the two types of macro clusters transduce different intracellular signals [28], suggesting that an analysis of both clustering and intracellular signaling is needed to fully study the effects of the two types of CD11b/CD18 agonists.

Therefore, to investigate, a combination of confocal microscopy (to study clustering) and western blotting assays (to study intracellular signaling) using K562 WT cells were used. First, CD11b/CD18 cell-surface distribution and macro clustering was studied under various conditions using confocal microscopy. K562 WT cells in suspension were incubated with various agonists, fixed with paraformaldehyde and the surface expressed CD11b/CD18 was fluorescently stained with anti-CD11b/CD18 mAb 1B4. The results are presented in FIGS. 5A and 5B. For FIG. 5A, cell suspensions were incubated for 45 minutes at 37° C. with DMSO (vehicle), non-selective agonist $Mn^{2+}$+(1 mM), agonist LA1 (15 uM), activating mAb KIM127 (1:100 dilution of ascites fluid), or the activating mAb 24 (20 μg/mL) in the absence (top panel, −Fg) or the presence of the ligand fibrinogen (50 μg/mL) (bottom panel, +Fg) and the cells were fixed with paraformaldehyde (4%) prior to labeling the surface expressed CD11b with anti-CD11b/CD18 mAb IB4 and imaged. The fluorescence images shown are representative of three independent experiments. White scale bar represents 25 μm. Also shown below each image is a 3D representation of CD11b fluorescence intensity for selected cells, analyzed in ImageJ In FIG. 5B, data shown are mean±SEM from >40 cells per condition and from >3 independent experiments for each condition. ***p<0.0001, ns=not significant.

Figure 5A:
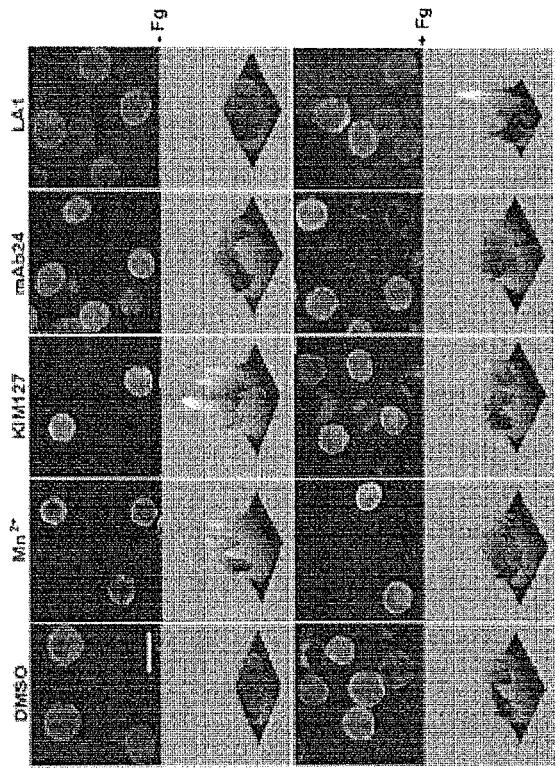
FIGS. 5A-5B show that activating antibodies, but not LA1, induce CD11b/CD18 clustering on live cells.
Figure 5B:
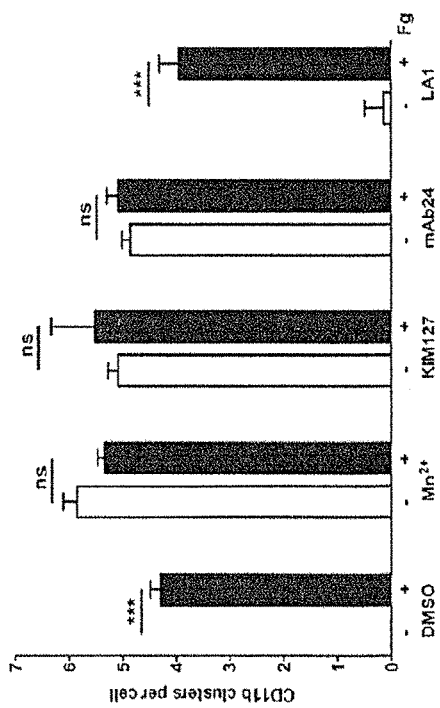
Figure 13A:
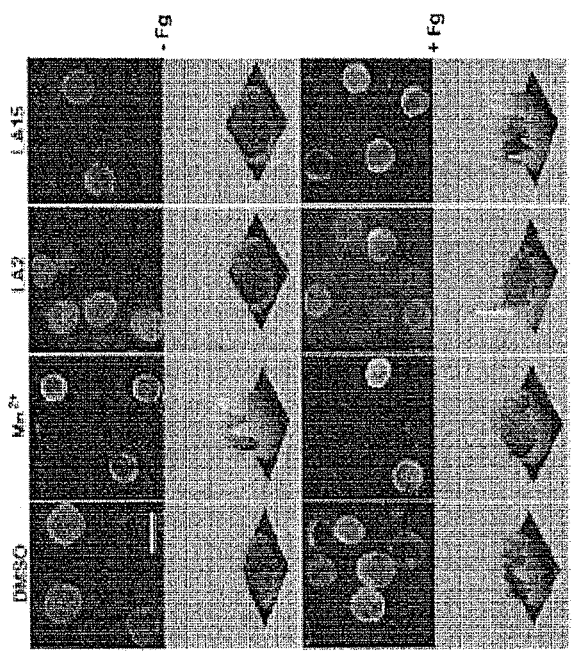
FIGS. 13A-13B show that activating antibodies, but not leukadherins LA2 and LA15, induce CD11b/CD18 clustering on live cells.
Figure 13B:
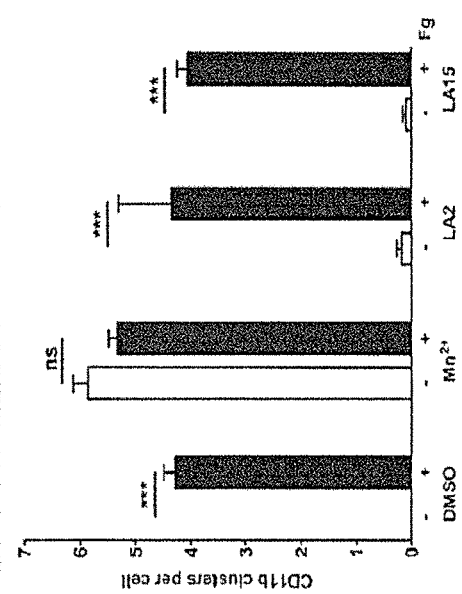

K562 WT cells showed uniform distribution of CD11b/CD18 on the cell surface, with minimal macro clustering, in the absence of any stimulus, ligands, agonists or antibodies (FIG. 5A, top panel, DMSO). As has been reported before, incubation of cells with ligand fibrinogen (Fg) resulted in significant CD11b/CD18 macro clustering (FIG. 5A, bottom panel, DMSO) when quantitated using ImageJ [80] (FIG. 5B). The agonist Mn2+, which has been shown to also induce CD11b/CD18 clustering [28], reproduced the clustering phenotype here (FIGS. 5A and 5B). Incubation of cells with the activating antibodies KIM127 and mAb 24 also resulted in significant CD11b/CD18 macro clustering on the cells surface and this increased level of integrin macro-clustering did not significantly change upon addition of the physiologic ligand fibrinogen, suggesting that activating anti-CD11b/CD18 antibodies induce CD11b/CD18 activation and clustering even in the absence of a ligand. Previous studies have also shown that other activating anti-CD11b antibodies, including VIM12 (which binds near the extracellular C-terminal region of CD11b [56]) and the full-length immunoglobulin (IgG) as well as the Fab-fragment of LFA-1/2 (which binds the EGF3 domain of CD18 [57, 58]), induce CD11b/CD18 clustering [28, 71]. However, incubation of the cells with the agonist LA1 alone did not induce any significant CD11b/CD18 macro clustering (FIG. 5A, top panel, LA1) in the absence of ligand fibrinogen, but did so in the presence of fibrinogen [55]. The leukadherins LA2 and LA15 showed similar results (FIGS. 13A and 13B). In FIG. 13A, cell suspensions were incubated for 45 minutes at 37° C. with DMSO (vehicle), non-selective agonist $Mn^{2+}$ (1 mM), the agonist LA2 (15 uM) or the agonist LA15 (15 uM) in the absence (top panel, −Fg) or the presence of the ligand fibrinogen (50 μg/mL) (bottom panel, +Fg) and the cells were fixed with paraformaldehyde (4%) prior to labeling the surface expressed CD11b with anti-CD11b/CD18 mAb IB4 and imaged. The fluorescence images shown are representative of three independent experiments. White scale bar represents 25 μm. Also shown below each image is a 3D representation of CD11b fluorescence intensity for selected cells, analyzed in ImageJ. For FIG. 13B, data shown are mean±SEM from >40 cells per condition and from >3 independent experiments for each condition. ***p<0.0001, ns=not significant. These data in FIGS. 5A-5B and 13A-13B show that the two types of integrin agonists have very different effects on the integrins on the distribution and clustering of CD11b/CD18 on the surface of live cells.

Figure 6A:
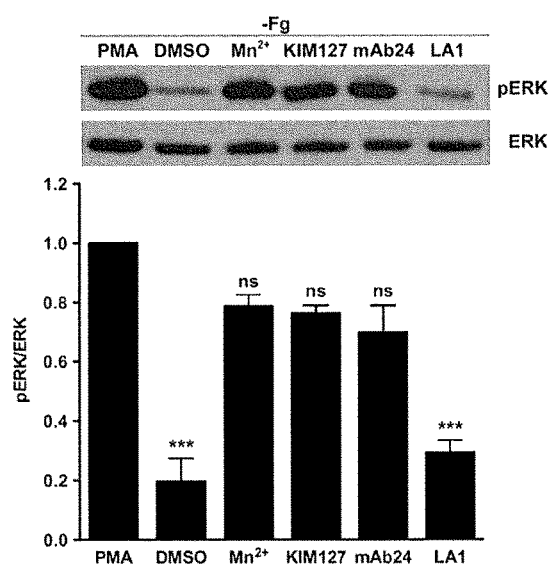
FIGS. 6A-6D are graphs and immunoblots showing that activating antibodies induce intracellular MAPK signaling that mimics ligand-bound state, but LA1 does not.
Figure 6C:
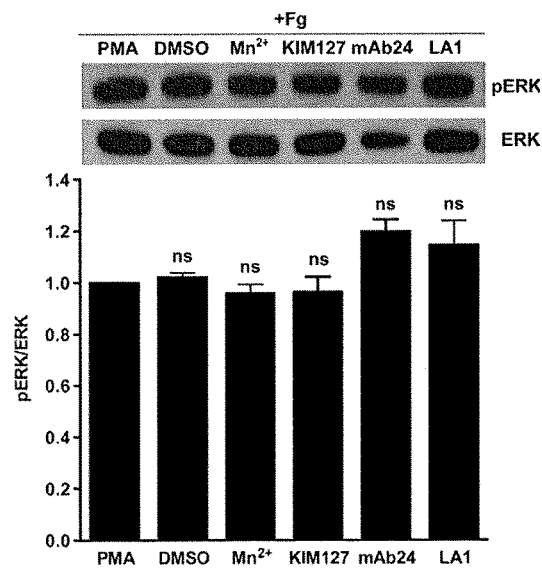
Figure 6B:
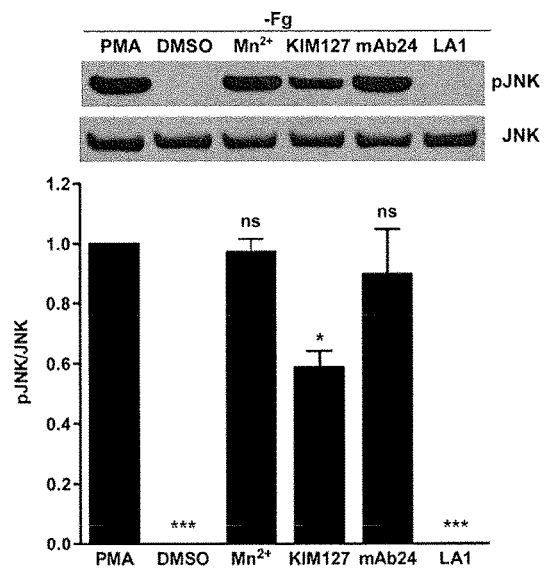
Figure 6D:
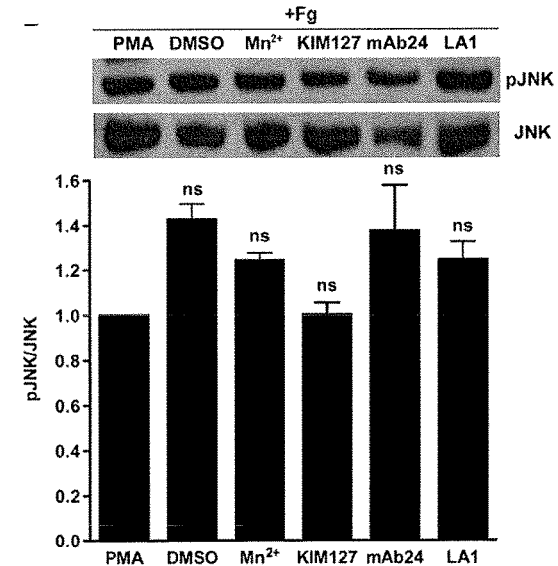

Second, an effect of integrin ligation, macro clustering and redistribution in the plasma membrane is the triggering of outside-in intracellular signaling in cells via various MAPKs [103]. Triggering of such MAPK signals also rapidly stimulates transcription and secretion of a variety of pro-inflammatory cytokines and chemokines in leukocytes [29]. To test, two such MAPK pathways were investigated—the ERK pathway and the c-Jun NH2-terminal kinase (JNK) pathway—by measuring the relative levels of phosphorylated ERK (pERK) and phosphorylated JNK (pJNK) using western blotting. K562 WT cells incubated with vehicle (DMSO) alone showed minimal ERK and JNK activation (FIGS. 6A-6D) as compared to cells that were incubated with ligand fibrinogen or were activated with the protein kinase C (PKC) agonist phorbol ester PMA (positive control, [104]). In FIGS. 6A-6B, immunoblot results from two independent experiments were quantified using ImageJ software and ratio of phosphorylated protein to total protein was determined. Histograms showing this quantitation for each set are also shown. Data shown are mean±SEM. *p<0.05, ***p<0.0001, ns=not significant. In FIGS. 6C-6D, immunoblot results from two independent experiments were quantified and are also shown, as in 6A and 6B.

Incubation of cells with agonist Mn2+ or the activating antibodies KIM127 or mAb 24 showed a significant activation of both ERK and JNK. Previously published studies have also shown that incubation of CD11b/CD18 expressing cells with either the agonist Mn2+ [101], blocking mAbs, ligand ICAM- or other anti-integrin activating mAbs [71], similarly induces ERK phosphorylation and MAPK signaling. Incubation of the cells with the agonist LA1 alone did not induce any significant pERK or pJNK in the absence of ligand fibrinogen. Additionally, the leukadherins LA2 and LA15 showed similar results (not shown). CD11b/CD18 ligation with fibrinogen showed high levels of both pERK and pJNK under all conditions, suggesting that such MAPK signaling may mimic a ligand-bound state of the cell. Thus, it is concluded that CD11b/CD18 binding to activating antibodies mimics its ligand-bound state and induces intracellular MAPK signaling, whereas CD11b/CD18 binding to leukadherins does not. It is worth noting that leukocytes from knock-in animals expressing constitutively active integrins CD11a/CD18 (LFA-1) or 0407 do not show MAPK signaling in the absence of ligand [105-107], similar to the results obtained with the leukadherins.

Collectively, these results show that while the two types of integrin agonists may have some common functional effects on CD11b/CD18 expressing cells (that they enhance ligand binding and cell adhesion), they can also have significant differences that show that one can be more beneficial for in vivo use over the other.

LA1 does not induce global conformational changes in CD11b/CD18. Ligand binding induces extension of the integrin heterodimer and large, global conformational changes leading to outside-in signaling [28, 69, 71]. Binding of activating antibodies also induces global conformational changes in the integrin heterodimer and such large conformational changes mimic those induced upon ligand binding [71, 72]. For example, activating antibody KIM127 recognizes a region in the EGF2 domain of CD18 that is buried in the inactive, bent conformation of the integrin CD11/CD18 heterodimers and stabilizes an extended conformation upon binding [57, 61, 66], which also leads to the separation of the cytoplasmic tails of the heterodimer [71, 108]. Thus, mAb KIM127 is often used as a reporter for the extended conformation of β2 integrins [70, 79, 83]. Similarly, mAb 24 binds to an activation-dependent epitope in the αA domain that mimics the ligand-bound conformation of the various CD11/CD18 heterodimers [59]. To determine the mechanistic basis for the lack of outside-in signaling by LA1 in the treated cells, the extent of the conformational changes caused by LA1 binding to cell-surface expressed CD11b/CD18 in K562 cells was investigated, using mAbs KIM127 and 24 as reporters of large/global conformational changes. Incubation of K562 WT cells in physiologic buffer alone showed basal level of KIM127 and mAb 24 binding, as measured by flow cytometry (FIGS. 7A and 7B). The binding by isotype IgG1 control antibody (15 ug/mL) is shown in the topmost panels. Cells were incubated with mAbs KIM127 or 24 in the absence of agonists (Control), in the presence of LA1 (15 uM) or $Mn^{2+}$ ions (1 mM). Data shown are representative of at least three independent experiments.

Expectedly, addition of integrin agonist Mn2+ ions was sufficient to induce maximal increase in the amount of bound KIM127 and mAb 24, mimicking the ligand binding induced global changes in the CD11b/CD18 heterodimer as has been reported in the literature [59, 70, 79, 83]. However, incubation of these cells with small molecule agonist LA1 produced a very small increase in the KIM127 binding (FIG. 7B), indicating that the LA1-mediated DA activation does not expose the KIM127 epitope in the EGF2 of CD18 and showing that LA1 binding leads to domain-limited conformational changes, but not large global conformational changes in the CD11b/CD18 heterodimer on live cell surfaces. The global conformational changes in integrins trigger cytoplasmic leg-separation and generate outside-in signaling [71, 108]. Similarly, LA1 binding showed a small increase in the binding of the second conformational reporter probe, the mAb 24, over the basal level of binding by mAb 24 to cell surface-expressed CD11b/CD18. In both cases, the level of reporter probe binding to CD11b/CD18 in the presence of LA1 was substantially less as compared to their binding in the presence of ligand-mimetic agonist Mn2+ ions.

While LA1 significantly reduces mechanical vascular injury in rats, the anti-CD11b activating antibody ED7 is ineffective. Percutaneous coronary intervention (PCI) is one of the most effective methods to unblock occluded arteries and facilitates coronary revascularization in humans [109]. Despite significant technological advances in PCI, restenosis (re-narrowing) secondary to neointimal hyperplasia remains a major complication limiting the success of coronary interventions in 5-25% of patients [110-112]. The recruitment of inflammatory macrophages and other leukocytes precedes neointimal hyperplasia [5]. The denudation of endothelial cell lining at the site of mechanical vascular injury during a PCI procedure leads to the deposition of fibrin and platelets, where selective binding between the platelet cell surface receptor GP lb☐ and leukocytic CD11b/CD18 leads to the migration and recruitment of these inflammatory cells [113]. Indeed, in experimental models, it has been shown that the genetic ablation of CD11b (CD11b−/− animals) or its blockade (using biological antagonists) can reduce neointima formation after angioplasty or stent implantation [5, 39]. Applicant has also previously demonstrated that LA1 significantly reduces macrophage accumulation at the site of mechanical vascular injury, resulting in significantly reduced neointimal hyperplasia [55]. Here, this experimental arterial balloon injury model was used to examine the relative efficacy of the two types of agonists, in a head-to-head comparison, on inflammatory responses in vivo. First, the dose-dependence of LA1 in this model system was determined. LA1 was administered at two different doses (0.05 or 1 mg/kg/d, intraperitoneal (i.p.)), or the vehicle (DMSO), in a saline solution to SD male rats 30 minutes prior to injury and continued daily injections for the next three weeks and subsequently measured the extent of vascular injury via tissue histology (FIGS. 14A-14D). Data shown are mean±SEM. *p<0.05, **p<0.001. The injured arteries of LA1-treated rats developed significantly less neointimal hyperplasia (FIGS. 14B and 14C) as compared to those of animals receiving vehicle alone (FIG. 14A). Additionally, LA1 showed a dose-dependent reduction in the extent of balloon catheter-induced mechanical vascular injury, with the higher dose producing a more significant reduction in it as compared to the vehicle treated control.

Next, to determine whether either type of agonist (chemical LA1 and biologic activating antibody) has a therapeutic advantage over the other, a head-to-head comparison was performed using this in vivo model. As the study involves use of rats as the experimental model system, the anti-rat CD11b activating mAb ED7 was chosen for comparison with LA1. Previous reports show that administration of ED7 reduced kidney and inflammatory bowel disease in rats [114, 115]. The mAb ED7 was obtained with high purity from ascites fluid according to published protocols [116]. Staining and flow cytometric analysis showed high degree of binding by the anti-CD11b mAb ED7, but not the control mAb mIgG1, to the purified primary rat macrophages and a selective enhancement in macrophage cell adhesion to immobilized fibrinogen by ED7 vs the control mAb IgG1. To examine the effects of the two types of agonists on migration and influx of inflammatory macrophages into injured arteries in this model of vascular injury, LA1 or ED7 was administered to wild type rats 30 minutes prior to balloon injury and continued daily for the next 7 days. The dosage of ED7 used was based on the published studies [114, 115, 117]. Next, the arteries were analyzed to quantify the number of infiltrated macrophages in the presence of agonists LA1 or ED7 and compared it to vehicle treated animals. The arteries were harvested from animals 7 days after balloon injury and single cell suspensions were analyzed by flow cytometry (using anti-rat CD11b antibody WT.5) to quantitate CD11b+ macrophages in each sample. The flow cytometry data, shown in FIGS. 8A-8D, reflects the distribution of macrophages within the arterial wall and the surrounding adventitia. Data shown are representative of at least 4-6 independent measurements. Data shown are mean±SEM. *p<0.05, **p<0.001, ns=not significant. Consistent with previous findings, injured arteries of LA1 treated animals contained significantly less CD11b/CD18 macrophages than those in the control vehicle treated rats. It was also found that ED7 treatment also similarly and significantly decreased the amount of infiltrated macrophages in the injured artery and in a dose dependent fashion (two doses of 1 mg/kg/d and 3.3 mg/kg/d were tested), showing the doses of ED7 used here to be highly effective in vivo. These results show that both types of agonists can similarly reduce macrophage influx into the tissue.

Next, in order to examine the relative efficacy of LA1 and ED7, LA1 (1 mg/kg/d) or ED7 (4 mg/kg/d) were administered to SD male rats 30 minutes prior to balloon injury and continued daily for the next 21 days. An isotype control antibody (mIgG1, 4 mg/kg/d) was administered to the control group of animals. Histochemical analysis of the injured rat arteries showed reduced neointimal thickening in ED7- and LA1-treated animals, as compared to the control mAb IgG1-treated group (FIGS. 9A-9D). Data shown are mean±SEM. *p<0.05, ***p<0.0001, ns=not significant. However, only LA1 showed a significant reduction in neointimal hyperplasia (NIH), as compared to the control group and also showed significantly less neointima formation as compared to the ED7 group, showing that LA1 is more efficacious than the CD11b-activating mAb ED7 in vivo in the rat balloon injury model. Together, these results show that leukadherin LA1 dose-dependently reduces vascular injury (as measured by neointimal thickening) and shows higher efficacy than anti-CD11b activating mAb ED7 in vivo and thus, has a clear therapeutic advantage.

Leukadherins are a family of small molecule compounds that are novel integrin CD11b/CD18 agonists. Leukadherins increase CD11b/CD18-dependent cell adhesion, reduce leukocyte migration and inflammatory injury in vivo. The in vitro and in vivo efficacy of leukadherins suggested that many agents that activate CD11b/CD18 and enhance cell adhesion could be developed into pharmacologically useful therapeutics to treat inflammation. However, in this study, it was found that not all integrin agonists are equal and that, as compared to the small molecule chemicals (leukadherins), biological agonists of CD11b/CD18, such as anti-CD11b activating antibodies, have additional effects on intracellular signaling by CD11b/CD18 that can reduce their potential as therapeutics. Such effects have also been reported with a number of ligand-mimetic integrin antagonists that have shown worsened clinical outcomes, perhaps due to induction of outside-in integrin signaling [118, 119]. It is found that CD11b/CD18 activation via both types of reagents (the chemical leukadherins and the biologic activating mAbs) increases integrin-mediated cell adhesion and decreases cell migration and wound healing in vitro. However, unlike leukadherins, the biologic anti-CD11b/CD18 activating antibodies induced clustering of the cell surface expressed CD11b/CD18 and the phosphorylation of key intracellular signaling proteins, including the JNK and ERK MAP kinases, showing that CD11b/CD18 engagement with activating antibodies mimics ligand-bound state. FIGS. 6A-6D clearly show that while both types of CD11b/CD18 agonists, the chemical LA1 and the activating antibodies, bind and allosterically activate the integrin receptors, the two types of agonists clearly induce different outside-in signaling in cells in the absence of a ligand (fibrinogen). FIGS. 6A-6D also show that at a high concentration of ligand, the two types of agonists do not interfere with the typical ligand-binding induced outside-in signaling, and such signaling is the same under both cases. However, clearly an activating antibody alone is sufficient to induce significant outside-in signaling whereas LA1 binding per se did not induce any such signaling. It is important to note here that fibrinogen becomes appreciable for leukocyte adhesion and activation only after surface deposition [120-122]. Fibrinogen deposition on the endothelial surface exposes the cryptic γ390-396 residues in fibrinogen that is recognized by the integrin CD11b/CD18 on leukocytes for high-affinity engagement, which leads to recruitment of leukocytes from circulation into the injured arteries. Furthermore, conformation-specific antibody probes were used to illustrate a potential reasoning behind these observed differences in signaling between the two types of agonists. Leukadherin binding did not induce large global conformational changes in the integrin CD11b/CD18, whereas the activating antibodies have been shown to induce such changes that mimic a ligand-bound integrin [71, 72]. Thus, while binding activating antibodies induce ligand-mimetic outside-in signaling in cells, binding of leukadherins seems to induce more modest, local changes in the integrin, which are likely not enough to induce outside-in signaling in cells (FIGS. 9A-9D). It has also been previously reported in literature that constitutively active integrin mutants, where the ligand-binding □A-domain of CD11b is locked in its active conformation, do not induce intracellular signaling [72]. Similarly, knock-in mice expressing constitutively active integrin mutants (□4□7 [106], CD11a/CD18 [107]) do not show any increase in outside-in signaling in leukocytes expressing constitutively active integrins. This shows that □A-domain activation, by itself, is likely not sufficient for inducing ligand-binding mimetic conformational changes and outside-in signaling, whereas binding of large, antibody agonists, certainly induces global conformational changes in integrins, thereby producing ligand-binding mimetic outside-in signaling. Thus, it further shows that the use of biologic activating antibodies can have additional unforeseen consequences, while the chemical leukadherins seem to have limited negative effects on leukocyte function. Additionally, when compared in a head-to-head study in a vascular injury model in vivo, while both types of agents similarly reduced the influx of inflammatory macrophages into the injured arteries, leukadherin LA1 dose-dependently reduced vascular injury and showed significantly higher efficacy than the anti-CD11b activating antibody ED7, showing that this small molecule agonist of CD11b/CD18 has a clear therapeutic advantage over the biologic activating antibody. However, more detailed mechanistic studies in the future will also be needed to provide more insights into the differences between the in vivo functions of the two types of agonists. Taken together, the data presented herein shows that leukadherins, which are newly discovered novel small molecule agonists of CD11b/CD18, are effective anti-inflammatory agents in vivo, and can be developed into novel therapeutics, whereas biological agonists of CD11b/CD18, in the form of anti-CD11b/CD18 activating antibodies, are sub-optimal and can require significant amount of optimization before they are ready for in vivo use.

Over the last more than 15 years, there have been at least three published reports on the use of anti-CD11b activating antibody ED7 in reducing inflammatory injury in vivo [114, 115, 117]. Thus, it was quite surprising to find that it was not more effective in reducing the balloon catheter induced vascular injury in rats here. There could be several reasons for this lack of efficacy of ED7. First, it is conceivable that the dose of ED7 used here (4 mg/kg/d) was inadequate. It is not believed that this was an issue here because it has previously been shown (in multiple studies) that similar doses of ED7 effectively reduced—a) the mobilization of leukocytes into the peritoneal cavity after thioglycollate-injection [123], b) intestinal damage in a model of acute colitis [115], and c) structural and functional injury in rats with Adriamycin-induced nephrosis [114]. Previous literature also shows that an even lower dose of ED7 (1-3 mg/kg) is effective even when administered every other day or even weekly [114, 115, 117] and that such amounts of anti-CD11b antibodies are sufficient enough to completely coat circulating leukocytes in the blood within 1 hour after injection and maintain it for at least 48 hours [115, 124]. Activating antibodies at such high level of integrin receptor binding on cells have also been previously reported in literature to have an effect on ligand binding—that they increase ligand binding at these doses [71]. Therefore, it was chosen to use this "effective" reported ED7 dose in animals with injured arteries to prevent inflammation and diseases development. Second, ED7 is a mouse anti-rat antibody and one could argue that immune-clearance by the rodent system limited its efficacy. However, as ED7 has previously been shown to have at least some in vivo efficacy in wild type rats and intraperitoneal administration of ED7 was shown to reduce Adriamycin induced nephropathy in animals [114, 115, 117], it is believed this is less of an issue as well. Third, as only ED7 was tested as a model test agent representing activating antibodies, it could be reasoned that other activating antibodies can be more efficacious biological agents in vivo. While not necessarily so (see the next point), it is believed that future studies with additional anti-CD11b activating antibodies would be a logical step to investigate such a possibility. A limitation here is that there aren't very many anti-CD11b/CD18 activating antibodies available for use in rodents, and that they do not have cross-reactivity between species, thus limiting their validation in multiple species. Fourth, the full IgG molecule of ED7 was used in the studies presented here. Since the ED7 IgG would, in addition to activating CD11b/CD18, dimerize CD11b/CD18 upon binding the integrin on the leukocyte cell surface, it is also plausible that a reason for the differences observed between the two types of agonists was due to the IgG induced dimerization, suggesting that a non-dimerizing Fab fragment of the activating antibodies may be better. However, Lefort, et al. recently showed that non-dimerizing Fab-fragments of activating anti-CD1b mAbs are sufficient to induce outside-in signaling in cells, whereas the Fab of non-activating, blocking anti-CD11b mAb 44 are not [71]. They also showed that CD11b/CD18 activation using activating mAbs, but not clustering, was sufficient to induce outside-in signaling in cells. Recent reports have suggested that activating antibodies can induce global conformational changes in the integrin heterodimer and that such changes mimic ligand binding induced outside-in signaling [71, 72]. It has also been previously reported that constitutively active integrin mutants, where the ligand-binding □A-domain of CD11b is locked in its active conformation, do not affect intracellular signaling [72]. These observations and our data suggests that LA1 binding to the □A-domain of CD11b may induce only local, domain-limited conformational changes in CD11b/CD18, whereas activating antibodies (whether IgG or Fab) and ligands induce a more global conformational activation of the entire integrin heterodimer and the concomitant outside-in signaling. It is likely that small molecule agonists, like LA1, prime integrin CD11b/CD18 and induce intermediate affinity conformations [70]. This might be relevant in the setting of vascular repair where the findings herein would suggest that ED7-bound leukocytes could be more "pro-inflammatory" in nature and enhance disease as compared to the LA1-bound cells. Future structural and functional studies will further define the actual activation state of LA1-bound CD11b/CD18. Thus, while it is plausible that Fab fragments of other biological agonists of CD11b/CD18 can show efficacy in a select few inflammatory models, it is also quite possible that anti-integrin activating antibodies in general, due to their display of some of the undesirable side-effects that have been described for the integrin antagonists [94-100], can have limited effectiveness and utility as a therapeutic. This shows that small molecules are better suited for the development of integrin agonists as therapeutics.

In conclusion, small molecule based agonists of CD11b/CD18 represent a preferred and effective pharmacological approach for the design of novel agents to treat a variety of inflammatory and autoimmune diseases in mammals.

Example 2

TLR4-mediated signaling requires participation of the adaptor protein MyD88 (43) and MyD88−/− mice are protected from kidney damage following IRI. TLR4 activation leads to the binding and stabilization of adaptor protein MyD88, which recruits downstream kinases to initiate Nf-kB-mediated pro-inflammatory signaling. Subsequently, TLR4 signaling induces a negative feedback loop by endogenous activation of CD11b/CD18, which activates Syk to phosphorylate MyD88, tagging it for ubiquitin-mediated destruction. This shows that CD11b/CD18 agonists lead to accelerated degradation of MyD88, thereby inducing a faster dampening of TLR4-mediated pro-inflammatory signaling pathways. A pilot experiment was carried out to validate this hypothesis by determining the levels of MyD88 in human monocytic THP-1 cells. It was found that TLR4 agonist LPS produced a robust MyD88 signal that was stable for at least 4 hours (FIG. 1). However, co-treatment of cells with LA1 lead to a much faster degradation of MyD88. Indeed, incubation of cells with LA1 alone (in the absence of LPS) resulted in a complete degradation of MyD88 in less than 2 hours, showing that activation of CD11b/CD18 can down-modulate MyD88-dependent intracellular signaling in leukocytes. This supports the statements that leukadherins mediated priming of integrins for activation negatively regulates intracellular signaling, including the inflammatory NF-kB signaling. Additionally, LA1 treatment of cells resulted in induction of Syk phosphorylation in leukocytes by Western blot based analysis of pSyk (not shown). Leukocytes were incubated with LA1 for 0-60 minutes and the levels of phosphorylated Syk, total Syk and GAPDH were assayed, showing that LA1 induces Syk phosphorylation.

Example 3

In this experiment, four groups of tumor-bearing animals were used (n=16/group) and tumor growth is shown in FIG.

Figure 2A:
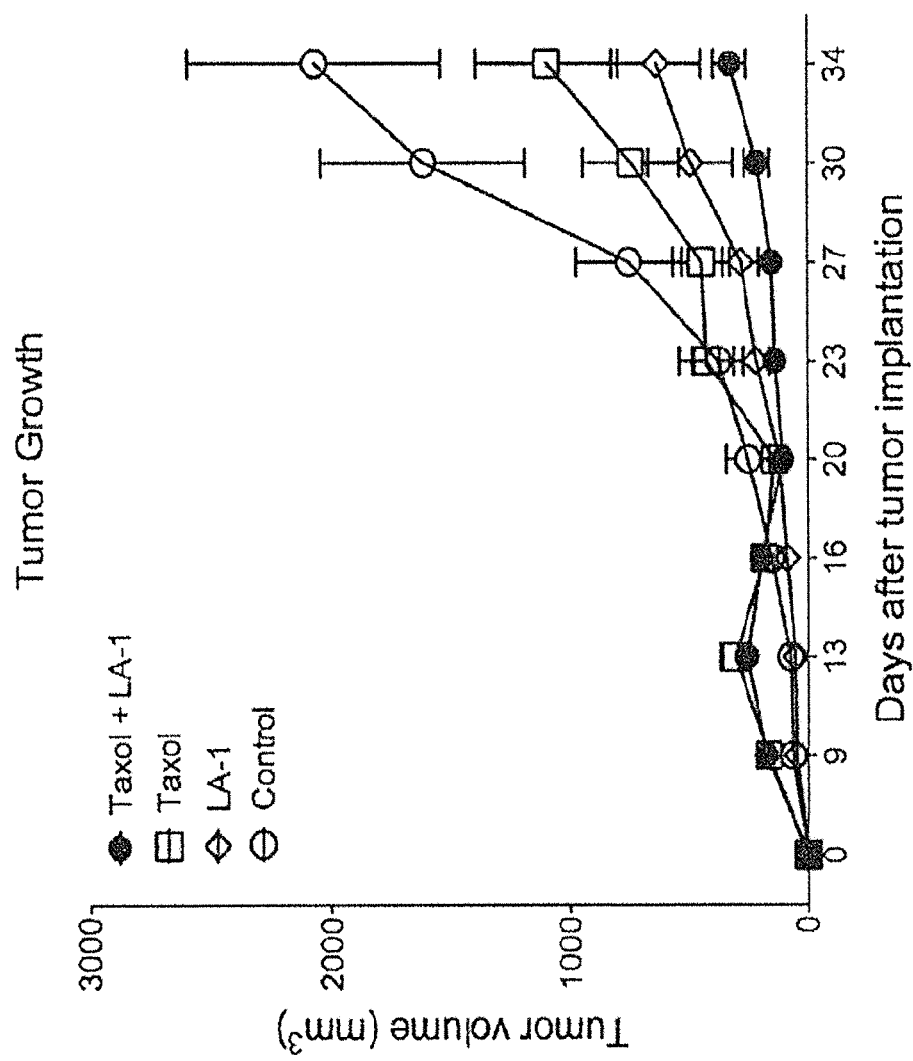
FIGS. 2A-2C shows that leukadherin LA1 reduces the rate of tumor growth upon treatment.
Figure 2B:
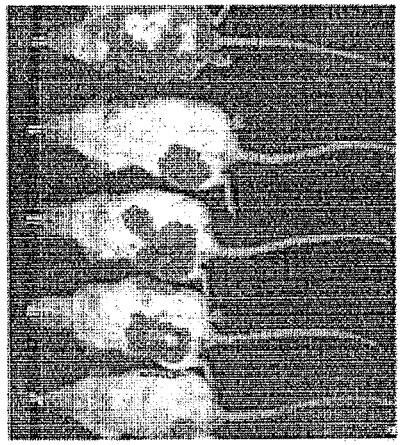
Figure 2C:
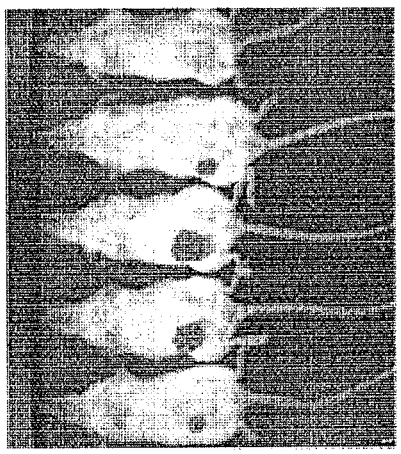

2A: 1) Treatment with vehicle alone (control, blue line), 2) Treatment with leukadherin LA1 alone (green line), 3) Treatment with taxol alone (purple line) and 4) Co-treatment with LA1 and Taxol (red line). The syngeneic murine mammary adenocarcinoma cell line Cl66 (moderately metastatic and is related to the highly metastatic 4T1 cell line) was orthotopically introduced in Balb/c animals, by injecting ~5×105 Cl66 cells under the left mammary fat pad of WT BALB/c mice (approx. 8-10 weeks old). The tumor size was measured using calipers every other day until the end of the experiment (approx. 5 weeks). 7-days post implantation, the tumors in all animals became palpable, with an average size of ~100 mm3. At that time, animals in each group were treated as described. LA1 was administered daily for the first two weeks and then every other day until the end of the experiment. Animals in Group 1 received Saline injections, as control. The results in this figure show a significant reduction in the rate of tumor growth in Taxol and, surprisingly, in LA1 treated animals (FIG. 2C, control group is shown in FIG. 2B). Additionally, and similarly surprisingly, animals co-treated with the compound LA1 and Taxol showed the highest reduction in the rate of tumor growth. This shows that leukadherins-mediated reduction in inflammatory leukocytes can significantly reduce tumor growth. It can also enhance the efficacy of traditional chemotherapy in various cancers, including breast cancer, to produce a synergistic response to the treatment. It can also reduce the incidence and the size of metastases.

Example 4

Figure 3:
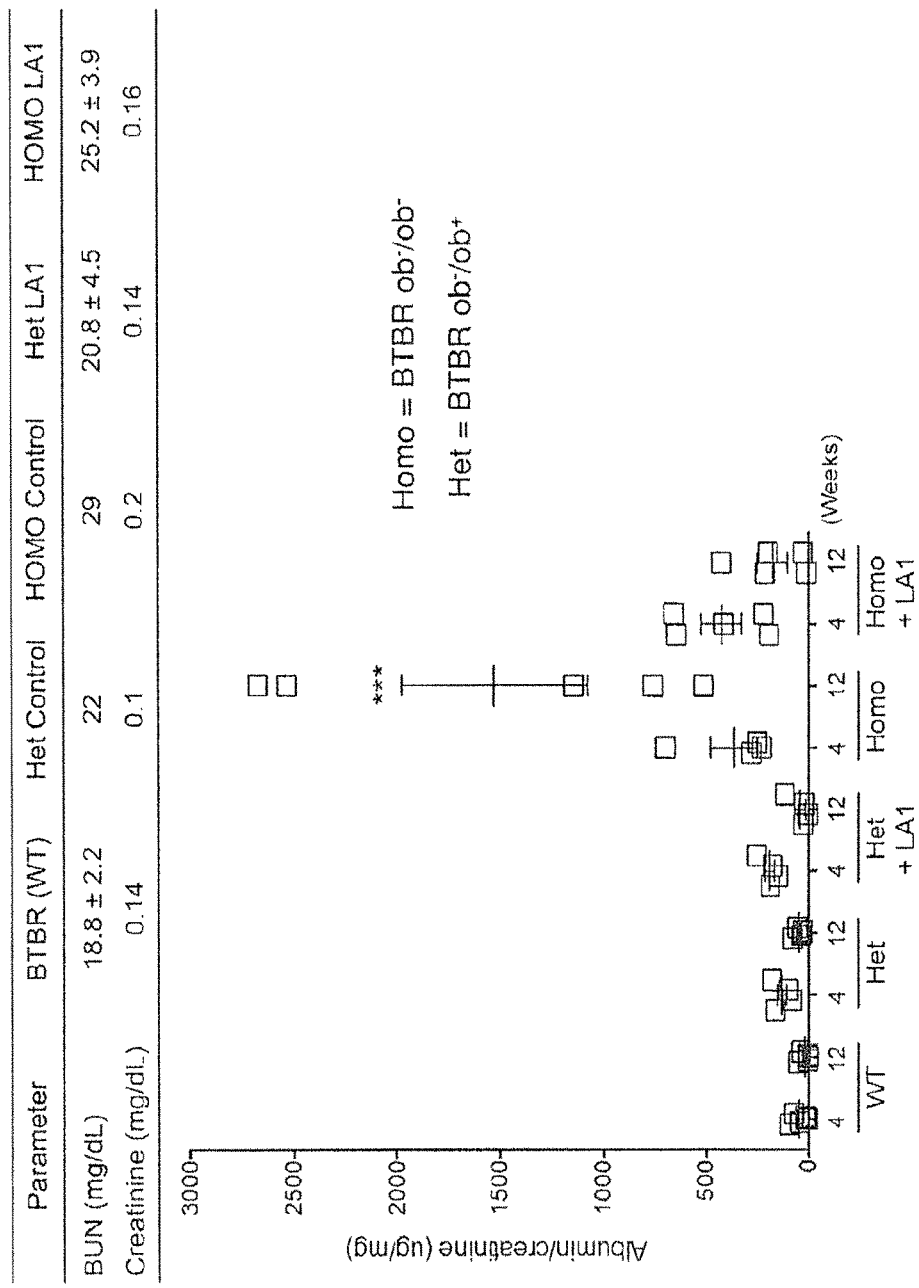
FIG. 3 is a graph showing that leukadherins reduce renal injury in diabetic animals.

The efficacy of LA1 was tested in an experimental model of Diabetic nephropathy (DN), where inflammation plays a major role. It was surmised that reducing leukocyte activation, recruitment and influx can be a beneficial strategy for developing therapeutics against DN. It was found that LA1 significantly prevents and/or treats DN, as seen in a murine model, which has been shown to more closely mimic the human disease (the BTBR ob/ob mouse model). Daily administration of our compound significantly reduced the number of infiltrating leukocytes in the kidney and preserved kidney function in fully diabetic animals. LA1 reduced glomerular damage and glomerular mesangial sclerosis. Data is shown in FIG. 3.

Additionally, in a model of allograft transplantation, co-treatment of animals with LA1 (with cyclosporine) provided much better engraftment of the donated kidney, suggesting that LA1 has therapeutic value for allograft nephropathy and other similar transplants (data not shown).

Example 5

It was shown that β2 integrin agonist leukdherin LA1 modulates the expression levels of various pro-inflammatory factors in cells. Human macrophages were treated with LPS in the absence or presence of LA1 in vitro and determined the levels of mRNA in the cells at various time points using Nanostring inflammation array (184 genes) and exiqon microRNA panels. The data shows that mRNA levels (and thus expression) of a number of pro-inflammatory factors (FIGS. 15A-15G and FIGS. 16A-16G, list in FIG. 17), that are upregulated by LPS treatment of these cells is significantly reduced in cells co-treated with LA1.

This supports the finding that leukadherins mediated priming of integrins for activation negatively regulates intracellular signaling, including the inflammatory NF-kB signaling.

Example 6

Figure 18A:
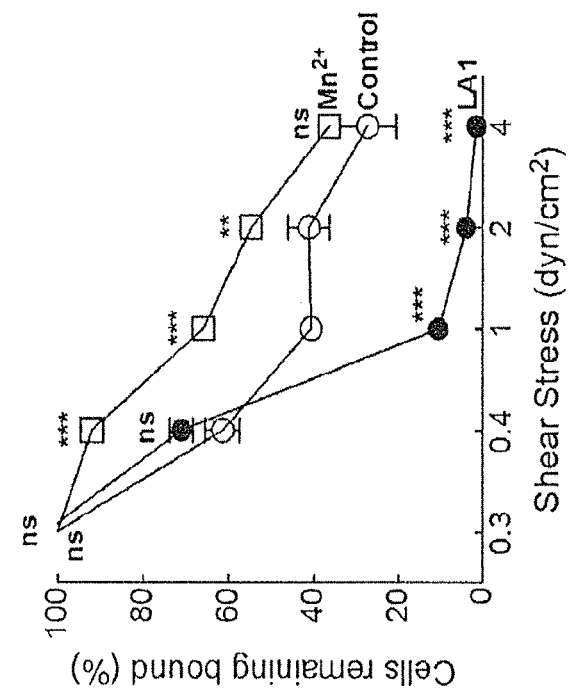
FIGS. 18A-18B are graphs showing cells resistant to detachment in shear flow.
Figure 18B:
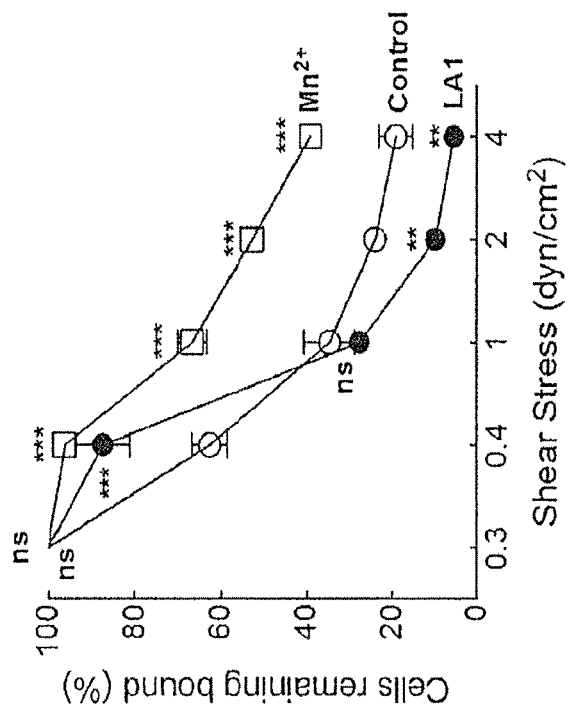

FIGS. 18A-18B and FIGS. 19A-19B show adhesive behavior of vehicle-, Mn2+ or LA-treated various CD11b/CD18 transfectant cells under the wall shear stress. FIGS. 18A-18B show cells resistant to detachment in shear flow. The total number of cells remaining bound at the end of each shear stress were plotted Error bars are ±s:d: (n=3).*: P<0.05; : P<0.01; *: P<0.001; and ns, not significant. In FIGS. 19A-19B, error bars are ±s:d: (n=3).*: P<0.05; : P<0.01; *: P<0.001; and ns, not significant. The results show that LA1, unlike Mn2+, induces priming of CD11b/CD18 and converts it into intermediate conformation.

Example 7

LA1 is non-toxic in vivo. A subacute toxicity assessment of LA1 in rats was performed. IP administered LA1 (~3 mg/kg/d for 21 d) failed to induce any overt toxicity or mortality in SD rats of both sexes. FIG. 20 shows that the biochemical measurements in serum and liver of LA1-treated rats revealed no appreciable changes in enzyme levels or serum constituents, such as proteins, cholesterol, urea and creatinine. Haematological constants in LA1-treated rats were on par with those of controls.

LA1 had no effect on the daily food intake or growth. Autopsy revealed no alterations in relative organ weights of various vital organs (lung, heart, spleen, liver, and kidney) or their histoarchitecture (FIG. 21). This shows that LA1 does not produce any significant acute and cumulative toxicity at the doses administered.

Example 7

FIGS. 22A-22E show that leukadherins are harmless to endothelial cells and are confocal images of DAPI-stained Human Umbilical Vein Endothelial Cells (HUVECs, blue) showing that LA1-mediated adhesion of neutrophils does not increase HUVEC apoptosis as measured by the Terminal deoxynucleotidyl transferase dUTP nick end labeling (TUNEL) assay, where incorporation of labeled dUTP marks apoptotic cells (Green). It shows that while positive control cells show a lot of TUNEL staining (green), LA1 treated cells do not. Leukadherins only temporarily promote the natural interaction between inflamed or denuded endothelium and leukocytes, but not to "healthy endothelium" (as the healthy cells do not express CD11b/CD18 ligands, such as ICAM-1 and CD40). In support of this argument, neither we nor others studying knock-in animals that express constitutively active mutants of integrins LFA-1 [54, 55] and □4□7 [56] have observed any signs of vascular injury in any experimental model. FIGS. 22A-22E show an absence of apoptosis in co-cultures of LA-1 activated leukocytes and HUVEC cells.

Figure 23:
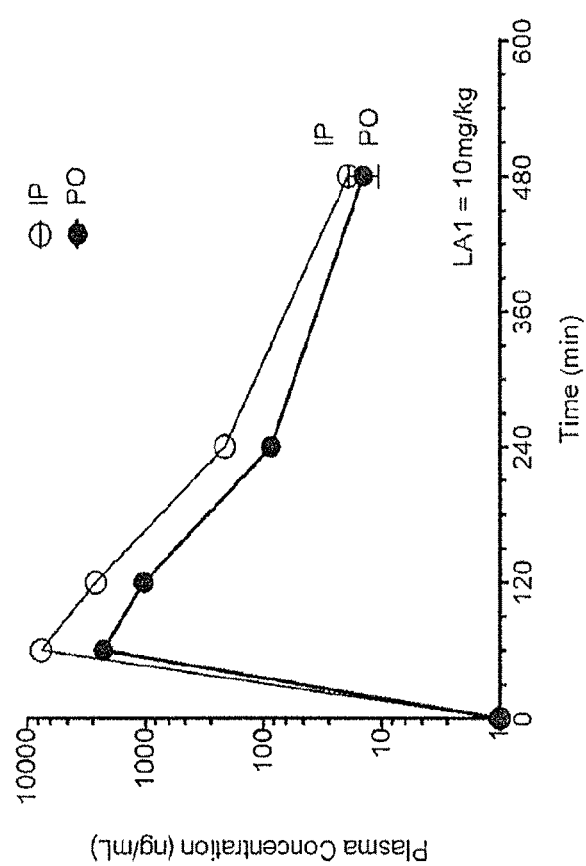
FIG. 23 is a graph showing leukadherin LA1 concentration in mouse blood over time after administration via two different routes.

FIG. 23 shows leukadherin LA1 concentration in mouse blood over time after administration via two different routes, showing that it is bioavailable in animals. With both oral (PO) and intraperitoneal (IP) dosing of LA1 at 10 mg/kg into animals (mice) showed high concentrations of LA1 in plasma (as measured by LC-MS), showing that LA1 is bioavailable and has micromolar levels in blood with mean residence time of at least a few hours.

Figure 24B:
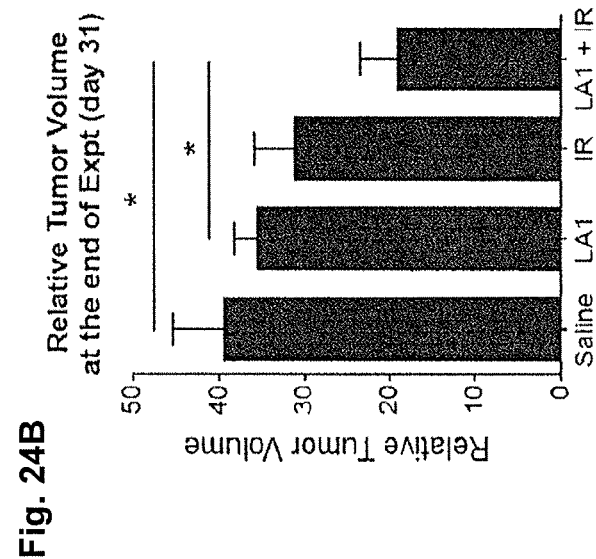
FIG. 24A is a graph of relative tumor growth and FIG. 24B is a chart of relative tumor volume.
Figure 24A:
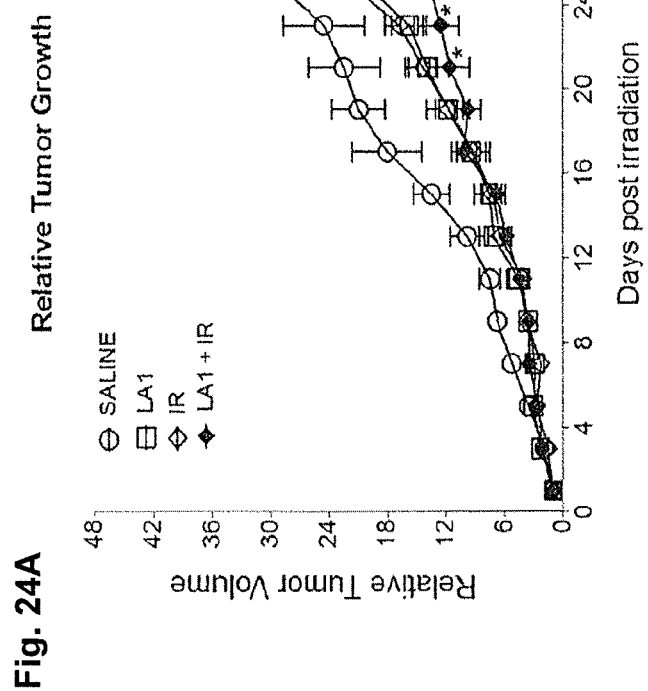

FIGS. 24A-24B show that leukadherin LA1 reduces the rate of tumor re-growth upon treatment. It shows (24A) the rate of tumor growth in animals in the various groups as well as (24B) the relative tumor volume in animals at the end of the study. Data shown are means±SEM. *, P<0.05; **, P<0.001 (by one-way ANOVA). In this experiment, four groups of tumor-bearing animals were used (n=11/group): 1) Treatment with saline alone (red line), 2) Treatment with leukadherins LA1 alone (orange line), 3) Treatment with a single dose of 20 Gy irradiation (two 10%+10% vertices) alone (black line) and 4) Treatment with a single dose of 20 Gy irradiation and then daily LA1 (at −2 hours) (blue line). The syngeneic murine mammary adenocarcinoma cell line Cl66 (moderately metastatic and is related to the highly metastatic 4T1 cell line) was orthotopically introduced in Balb/c animals, by injecting approximately 5×105 Cl66 cells under the left mammary fat pad of WT BALB/c mice (approximately 10 weeks old). The tumor size was measured using calipers every other day until the end of the experiment (approximately 5 weeks). 7-days post implantation, the tumors in all animals became palpable, with an average size of ~100 mm3. At that time, animals in groups 3 and 4 were treated with irradiation. Animals in group 4 received LA1, starting at 2 hours prior to irradiation. LA1 was administered daily for the first week and then every other day until the end of the experiment (when the tumor size reached 10% of the body weight). Animals in Group 1 received Saline injections, as control. The results in FIGS. 24A-24B show a significant reduction in the rate of tumor growth post-irradiation in LA1 treated animals. Additionally, and quite surprisingly, animals treated with the compound LA1 alone, in the absence of any irradiation (Group 2) also showed a reduced rate of tumor growth, to the level similar to the rate that was observed with irradiation alone.

Figure 25:
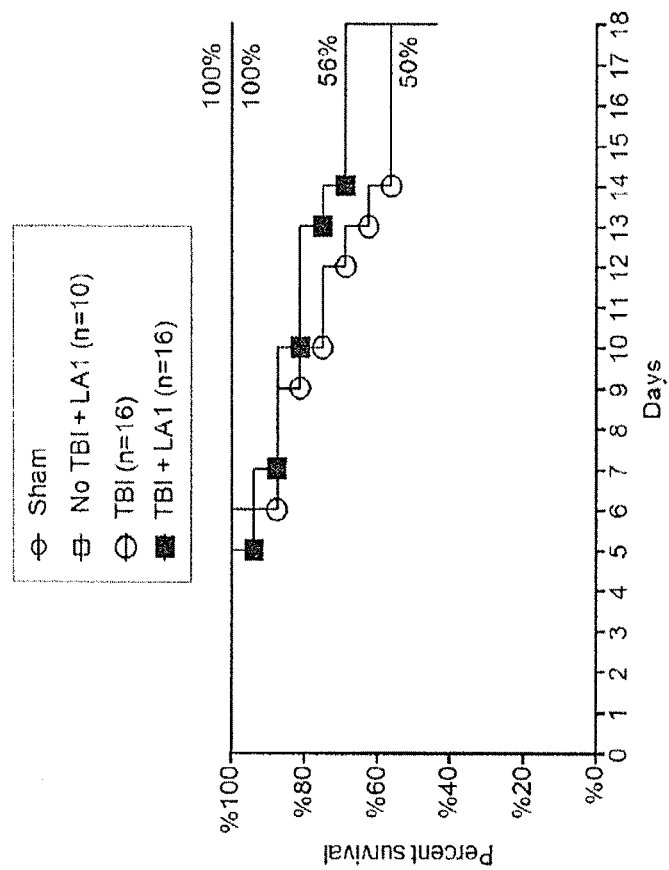
FIG. 25 is a graph of percent survival of different treatment groups.

FIG. 25 shows a survival curve showing that treatment of animals with leukadherin LA1, with or without sublethal total body irradiation, does not negatively affect animal mortality. Control groups (16 mice per group) of 6-8 weeks old C57BL/6J mice received a single sublethal dose (6 Gy) of total body radiation (TBI) and were monitored for survival with radiation alone. The experimental groups (16 mice per group) of 6-8 weeks old C57BL/6J received a single sublethal dose (6 Gy) of total body radiation (TBI) and were administered leukadherin LA1 (20 µg/animal) for seven consecutive days. Additionally, two additional control groups of animals were monitored—animals with no treatment at all or animals that were administered LA1 for seven consecutive days in the absence of any irradiation. The results, shown in FIG. 25, demonstrate that treatment of LA1 did not result in any increase in animal mortality over LA1-untreated animals. In fact, LA1 treatment shows a protective effect, showing an optimized dose of LA1 would be even more protective.

FIGS. 26A-26C show the analysis of hematopoiesis and HSC compartment in LA1 (Red bars), Vehicle control (Blue bars) treated groups of mice at 4 weeks after 6 Gy of total body irradiation (TBI), showing that LA1 is highly radioprotective and a radio-mitigator. FIGS. 26A-26C show that LA1 protects hematopoiesis and HSC compartments and cells after sublethal IR even when the LA1 treatment is delayed, thus effectively mitigating the adverse effects of sublethal IR on the hematopoietic system and HSCs. Mice were exposed to 6 Gy of TBI (at 0.5 Gy/min), and treated intraperitoneally (i.p.) with LA1 (1 mg/kg) or vehicle alone for 7 consecutive days starting at 24 hours post TBI. Analysis of HSCs 4-weeks post TBI showed a significant improvement in the LA1 treated group, as measured by BM cellularity, the frequency of LKS+ BM cells and LKS+ CD150+ CD48− BM cells (highly enriched for LTR-HSCs). The same trend was observed at 8 and 12 weeks after TBI (data not shown), indicating that delayed treatment with LA1 accelerates recovery of hematopoiesis and either preserves HSCs or facilitates the recovery of HSC compartment after sublethal IR.

Figure 27:
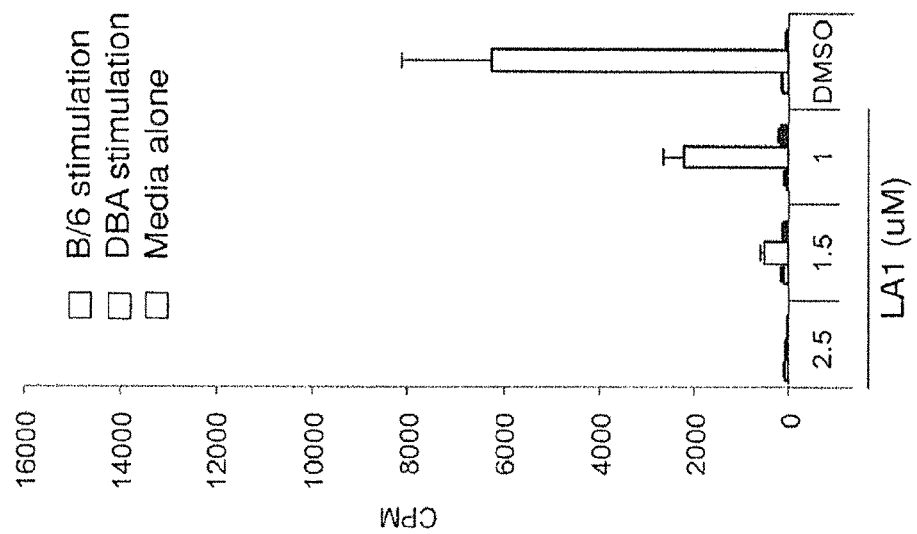
FIG. 27 is a graph showing T cell proliferation with doses of LA1.

FIG. 27 shows LA1 dose-dependently reduces T-cell proliferation, as measured by a Mixed lymphocyte reaction (MLR). Additionally, LA1 decreased IFN-□ production by T-cells in an antigen dose-dependent fashion (MOG-peptide, data not shown) when antigen-reactive T cells from the draining lymph nodes of mice were assessed.

Figure 28:
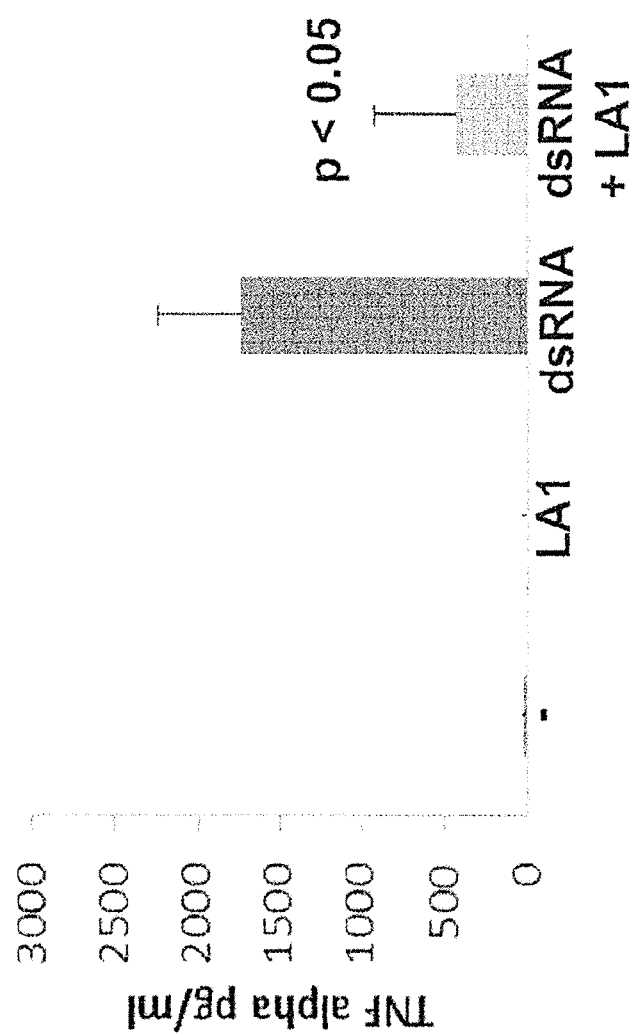
FIG. 28 is a graph of TNF-α release.

FIG. 28 shows that LA1 treatment of human macrophages from lupus patients with dsRNA (a lupus antigen) significantly reduced the TNF-α release, whereas exposure of macrophages to LA1 alone had no effect on cellular morphology and LA1 alone did not induce TNF-α over 24 hrs. This also shows that LA1 significantly attenuates pro-inflammatory phenotype in macrophages and neutrophils from lupus patients, including those from subjects with the coding variant of R77H.

Figure 29:
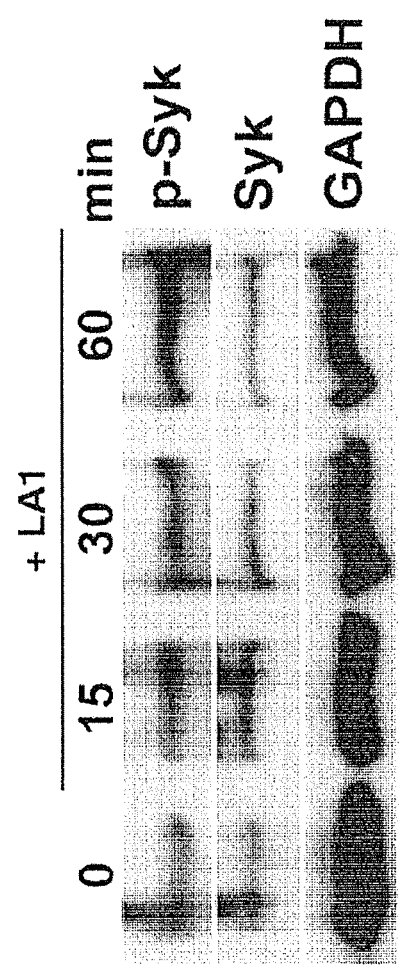
FIG. 29 is a Western blot of Syk phosphorylation.

FIG. 29 shows that LA1 induces Syk phosphorylation in leukocytes by Western blot based analysis of Syk phosphorylation. Leukocytes were incubated with LA1 for 0-60 minutes and the levels of phosphorylated Syk, total Syk and GAPDH were assayed, showing that LA1 induces Syk phosphorylation.

Results

LA1 is non-toxic in viva A pilot in vitro ADME assay (neutrophils, hepatocytes, hERG) showed no adverse findings with LA1 (at up to 100 □M) (not shown). Next, a subacute toxicity assessment was performed of LA1 in rats in the Comparative Pathology core. IP administered LA1 (~3 mg/kg/d for 21 d) failed to induce any overt toxicity or mortality in SD rats of both sexes. Further, no significant alterations either in relative organ weights or their histology were discernible at terminal autopsy. LA1 had no effect on the daily food intake or growth. Autopsy revealed no alterations in relative organ weights of various vital organs (lung, heart, spleen, liver, and kidney) or their histoarchitecture. Haematological constants in LA1-treated rats were on par with those of controls. The biochemical measurements in serum and liver of LA1-treated rats revealed no appreciable changes in enzyme levels or serum constituents, such as proteins, cholesterol, urea and creatinine. This shows that LA1 does not produce any significant acute and cumulative toxicity at the doses administered.

Pilot oral vehicle evaluation. Five different salts of LA1 (Na, K, NH4, Ca and Mg) were characterized using XPRD, DCS and TGA and tested for aqueous solubility (not shown), which showed improved crystalline form for LA1 in its magnesium salt, although poor equilibrium aqueous solubility (~0.6 µg/ml). Additionally, eight different vehicle formulations were prepared using the Mg-salt of LA1, using methylcellulose (MC), MC/SDS mixture, Tween, ETPGS, Captisol, sucrose, gelatin or propylene glycol. 10 mg/mL slurry samples of LA1 were prepared in each of the eight formulations and LA1's solubility was examined using LC-MS. At least three—10% Tween80, 20% ETPGS and 30% Captisol—showed enhanced solubility of LA1 (3-4 mg/mL). Subsequently, re-dispersability of LA1 was tested using two simulated biological fluids—simulated gastric fluid (SGF) and Fasted State Simulated Gastric Fluid (FaSSIF). Results showed that LA1 had much higher solubility in each of the three formulations, up to ~0.15 mg/mL in the case of 10% Tween80, showing that such vehicle screening approaches have the potential to significantly improve delivery and dosing of LA1 to animals.

A syngeneic xenograft model was used to address the effects of inflammatory cell recruitment on tumor cell regrowth after radio-therapy. In this pilot experiment, it was decided to use four groups of tumor-bearing animals (n=11/group): 1) Treatment with saline alone, 2) Treatment with leukadherins LA1 alone, 3) Treatment with a single dose of 20 Gy irradiation (using the LATTICE method, two 10%+ 10% vertices) alone and 4) Treatment with a single dose of 20 Gy irradiation and LA1 (at −2 h). The murine mammary adenocarcinoma cell line Cl66 (moderately metastatic and is related to the highly metastatic 4T1 cell line) was orthotopically introduced in all animals, by injecting ~5×105 Cl66 cells under the left mammary fat pad of WT BALB/c mice (10 weeks old). The tumor size was measured using calipers every other day until the end of the experiment (approximately 5 weeks). 7-days post implantation, the tumors, in all animals became palpable, with an average size of ~100 mm³. At that time, animals in groups 3 and 4 were treated with irradiation. Animals in group 4 received LA1, starting at 2 hours prior to irradiation. LA1 was administered daily for the first week and then every other day until the end of the experiment (when the tumor size reached 10% of the body weight). Animals in Group 1 received Saline injections, as control. Preliminary results of this experiment are presented in FIGS. 24A-24B. They show a significant reduction in the rate of tumor growth post-irradiation in LA1 treated animals. Additionally, and quite surprisingly, animals treated with the compound LA1 alone, in the absence of any irradiation (Group 2) also showed a reduced rate of tumor growth, to the level similar to the rate that was observed with irradiation alone.

Treatment of human macrophages (as well as dendritic cells and neutrophils, not shown) from normal healthy volunteers and from lupus patients with ds RNA antigen (R848) significantly stimulated TNF-α release compared with macrophages alone, as shown in FIG. 28 (n=14). When cells were exposed to R848 and LA1, their ability to release TNF-α was significantly impaired (p=0.05). Note that exposure of cells to LA1 alone had no effect on cellular morphology and LA1 alone did not induce TNF-α over 24 hrs. Similar results were obtained with FMLP and other reagents. Thus, the compounds of the present invention significantly attenuate pro-inflammatory phenotype in leukocytes (such as macrophages, dendritic cells and neutrophils) from patients, including those from subjects with the coding variant of CD11b, such as the R77H variant.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Mayadas, T. N. and X. Cullere, *Neutrophil beta2 integrins: moderators of life or death decisions*. Trends Immunol, 2005. 26(7): p. 388-95.
2. Ley, K., et al., *Getting to the site of inflammation: the leukocyte adhesion cascade updated*. Nat Rev Immunol, 2007. 7(9): p. 678-89.
3. Hynes, R. O., *Integrins: bidirectional, allosteric signaling machines*. Cell, 2002. 110(6): p. 673-87.
4. Arnaout, M. A., *Leukocyte adhesion molecules deficiency: its structural basis, pathophysiology and implications for modulating the inflammatory response*. Immunol Rev, 1990. 114: p. 145-80.
5. Simon, D. I., et al., *Decreased neointimal formation in Mac-1(−/−) mice reveals a role for inflammation in vascular repair after angioplasty*. J Clin Invest, 2000. 105(3): p. 293-300.
6. Cao, C., et al., *A specific role of integrin Mac-1 in accelerated macrophage efflux to the lymphatics*. Blood, 2005. 106(9): p. 3234-41.
7. Tang, T., et al., *A role for Mac-1 (CDIIb/CD18) in immune complex-stimulated neutrophil function in vivo: Mac-1 deficiency abrogates sustained Fcgamma receptor-dependent neutrophil adhesion and complement-dependent proteinuria in acute glomerulonephritis*. J Exp Med, 1997. 186(11): p. 1853-63.
8. Plow, E. F., et al., *Ligand binding to integrins*. J Biol Chem, 2000. 275(29): p. 21785-8.
9. Soriano, S. G., et al., *Mice deficient in Mac-1 (CD11b/CD18) are less susceptible to cerebral ischemia/reperfusion injury*. Stroke, 1999. 30(1): p. 134-9.
10. Ophascharoensuk, V., et al., *Role of intrinsic renal cells versus infiltrating cells in glomerular crescent formation*. Kidney Int, 1998. 54(2): p. 416-25.
11. Le Hir, M., et al., *Podocyte bridges between the tuft and Bowman's capsule: an early event in experimental crescentic glomerulonephritis*. J Am Soc Nephrol, 2001. 12(10): p. 2060-71.
12. Tang, T., et al., *A role for Mac-1 (CDIIb/CD18) in immune complex-stimulated neutrophil function in vivo: Mac-1 deficiency abrogates sustained Fcgamma receptor-dependent neutrophil adhesion and complement-dependent proteinuria in acute glomerulonephritis*. J Exp Med, 1997. 186(11): p. 1853-63.
13. Kubota, Y., et al., *M-CSF inhibition selectively targets pathological angiogenesis and lymphangiogenesis*. J Exp Med, 2009. 206(5): p. 1089-102.
14. Ahn, G. O., et al., *Inhibition of Mac-1 (CD11b/CD18) enhances tumor response to radiation by reducing myeloid cell recruitment*. Proc Natl Acad Sci USA. 107 (18): p. 8363-8.
15. Zhao, W. and M. E. Robbins, *Inflammation and chronic oxidative stress in radiation-induced late normal tissue injury: therapeutic implications*. Curr Med Chem, 2009. 16(2): p. 130-43.
16. Robbins, M. E. and W. Zhao, *Chronic oxidative stress and radiation-induced late normal tissue injury: a review*. Int J Radiat Biol, 2004. 80(4): p. 251-9.
17. Moulder, J. E. and E. P. Cohen, *Future strategies for mitigation and treatment of chronic radiation-induced normal tissue injury*. Semin Radiat Oncol, 2007. 17(2): p. 141-8.
18. Klaunig, J. E., L. M. Kamendulis, and B. A. Hocevar, *Oxidative stress and oxidative damage in carcinogenesis*. Toxicol Pathol, 2010. 38(1): p. 96-109.
19. Pazhanisamy, S. K., et al., *NADPH oxidase inhibition attenuates total body irradiation-induced haematopoietic genomic instability*. Mutagenesis, 2011. 26(3): p. 431-5.
20. Ito, K., et al., *Reactive oxygen species act through p38 MAPK to limit the lifespan of hematopoietic stem cells*. Nat Med, 2006. 12(4): p. 446-51.

21. Osawa, M., et al., *Long-term lymphohematopoietic reconstitution by a single CD34-low/negative hematopoietic stem cell.* Science, 1996. 273(5272): p. 242-5.
22. Kondo, M., I. L. Weissman, and K. Akashi, *Identification of clonogenic common lymphoid progenitors in mouse bone marrow.* Cell, 1997. 91(5): p. 661-72.
23. Zhao, W. and M. E. C. Robbins, *Inflammation and chronic oxidative stress in radiation-induced late normal tissue injury: therapeutic implications.* Curr Med Chem, 2009. 16(2): p. 130-43.
24. Robbins, M. E. C. and W. Zhao, *Chronic oxidative stress and radiation-induced late normal tissue injury: a review.* Int J Radiat Biol, 2004. 80(4): p. 251-9.
25. Wang, Y., et al., *Total body irradiation causes residual bone marrow injury by induction of persistent oxidative stress in murine hematopoietic stem cells.* Free Radic Biol Med, 2010. 48(2): p. 348-56.
26. Spitz, D. R., et al., *Metabolic oxidation/reduction reactions and cellular responses to ionizing radiation: a unifying concept in stress response biology.* Cancer Metastasis Rev, 2004. 23(3-4): p. 311-22.
27. Fan, S. T. and T. S. Edgington, *Coupling of the adhesive receptor CD11b/CD18 to functional enhancement of effector macrophage tissue factor response.* J Clin Invest, 1991. 87(1): p. 50-7.
28. Whitlock, B. B., et al., *Differential roles for alpha(M) beta(2) integrin clustering or activation in the control of apoptosis via regulation of akt and ERK survival mechanisms.* J Cell Biol, 2000. 151(6): p. 1305-20.
29. Rezzonico, R., et al., *Ligation of CD11b and CD11c beta(2) integrins by antibodies or soluble CD23 induces macrophage inflammatory protein 1alpha (MIP-1alpha) and MIP-1 beta production in primary human monocytes through a pathway dependent on nuclear factor-kappaB.* Blood, 2001. 97(10): p. 2932-40.
30. Guha, M. and N. Mackman, *The phosphatidylinositol 3-kinase-Akt pathway limits lipopolysaccharide activation of signaling pathways and expression of inflammatory mediators in human monocytic cells.* J Biol Chem, 2002. 277(35): p. 32124-32.
31. Rubel, C., et al., *Fibrinogen-CD11b/CD18 interaction activates the NF-kappa B pathway and delays apoptosis in human neutrophils.* Eur J Immunol, 2003. 33(5): p. 1429-38.
32. Kettritz, R., et al., *Integrins and cytokines activate nuclear transcription factor-kappaB in human neutrophils.* J Biol Chem, 2004. 279(4): p. 2657-65.
33. Giancotti, F. G. and E. Ruoslahti, *Integrin signaling.* Science, 1999. 285(5430): p. 1028-32.
34. Han, C., et al., *Integrin CD11b negatively regulates TLR-triggered inflammatory responses by activating Syk and promoting degradation of MyD88 and TRIF via Cbl-b.* Nat Immunol. 11(8): p. 734-42.
35. Cao, C., et al., *The efficacy of activated protein C in neurine endotoxemia is dependent on integrin CD11b.* J Clin Invest. 120(6): p. 1971-80.
36. Means, T. K. and A. D. Luster, *Integrins limit the Toll.* Nat Immunol. 11(8): p. 691-3.
37. Zen, K., et al., *Cleavage of the CD11b extracellular domain by the leukocyte serprocidins is critical for neutrophil detachment during chemotaxis.* Blood, 2011. 117(18): p. 4885-94.
38. Jaeschke, H., et al., *Functional inactivation of neutrophils with a Mac-1 (CD11b/CD18) monoclonal antibody protects against ischemia-reperfusion injury in rat liver.* Hepatology, 1993. 17(5): p. 915-23.
39. Rogers, C., E. R. Edelman, and D. I. Simon, *A mAb to the beta2-leukocyte integrin Mac-1 (CD11b/CD18) reduces intimal thickening after angioplasty or stent implantation in rabbits.* Proc Natl Acad Sci USA, 1998. 95(17): p. 10134-9.
40. Wilson, I., et al., *Inhibition of neutrophil adherence improves postischeinic ventricular performance of the neonatal heart.* Circulation, 1993. 88(5 Pt 2): p. 11372-9.
41. Plow, E. F. and L. Zhang, *A MAC-1 attack: integrin functions directly challenged in knockout mice.* J Clin Invest, 1997. 99(6): p. 1145-6.
42. Yonekawa, K. and J. M. Harlan, *Targeting leukocyte integrins in human diseases.* J Leukoc Biol, 2005. 77(2): p. 129-40.
43. Hu, X., et al., *beta2-integrins in demyelinating disease: not adhering to the paradigm.* J Leukoc Biol, 2010. 87(3): p. 397-403.
44. Dove, A., *CD18 trials disappoint again.* Nat Biotechnol, 2000. 18(8): p. 817-8.
45. Shimizu, K., et al., *Leukocyte integrin Mac-1 promotes acute cardiac allograft rejection.* Circulation, 2008. 117(15): p. 1997-2008.
46. Ramamoorthy, C., et al., *CD18 adhesion blockade decreases bacterial clearance and neutrophil recruitment after intrapulmonary E. coli, but not after S. aureus.* J Leukoc Biol, 1997. 61(2): p. 167-72.
47. Lum, A. F., et al., *Dynamic regulation of LFA-1 activation and neutrophil arrest on intercellular adhesion molecule 1 (ICAM-1) in shear flow.* J Biol Chem, 2002. 277(23): p. 20660-70.
48. Allison, M., *PML problems loom for Rituxan.* Nat Biotechnol, 2010. 28(2): p. 105-6.
49. Park, J. Y., M. A. Arnaout, and V. Gupta, *A simple, no-wash cell adhesion-based high-throughput assay for the discovery of small-molecule regulators of the integrin CD11b/CD18.* J Biomol Screen, 2007. 12(3): p. 406-17.
50. Faridi, M. H., et al., *Identification of novel agonists of the integrin CD11b/CD18.* Bioorg Med Chem Lett, 2009. 19(24): p. 6902-6.
51. Nath, S. K., et al., *A nonsynonymous functional variant in integrin-alpha(M) (encoded by ITGAM) is associated with systemic lupus erythematosus*, Nat Genet, 2008. 40(2): p. 152-4.
52. Shimaoka, M., et al., *Structures of the alpha L I domain and its complex with ICAM-1 reveal a shape-shifting pathway for integrin regulation.* Cell, 2003. 112(1): p. 99-111.
53. Gaestel, M., A. Kotlyarov, and M. Kracht, *Targeting innate immunity protein kinase signalling in inflammation.* Nat Rev Drug Discov, 2009. 8(6): p. 480-99.
54. Arnaout, M. A., *Integrin structure: new twists and turns in dynamic cell adhesion.* Immunol Rev, 2002. 186: p. 125-40.
55. Maiguel, D., et al., *Small molecule-mediated activation of the integrin CD11b/CD18 reduces inflammatory disease.* Sci Signal, 2011. 4(189): p. ra57.
56. Stockl, J., et al., *Granulocyte activation via a binding site near the C-terminal region of complement receptor-type 3 alpha-chain (CD11b) potentially involved in intramembrane complex formation with glycosylphosphatidylinositol-anchored Fc gamma RIIIB (CD16) molecules.* J Immunol, 1995. 154(10): p. 5452-63.
57. Lu, C., et al., *Epitope mapping of antibodies to the C-terminal region of the integrin beta 2 subunit reveals regions that become exposed upon receptor activation.* J Immunol, 2001. 166(9): p. 5629-37.

58. Petruzzelli, L., L. Maduzia, and T. A. Springer, *Activation of lymphocyte function-associated molecule-1 (CD11a/CD18) and Mac-1 (CD11b/CD18) mimicked by an antibody directed against CD18.* J Immunol, 1995. 155(2): p. 854-66.
59. Dransfield, I. and N. Hogg, *Regulated expression of Mg2+ binding epitope on leukocyte integrin alpha subunits.* EMBO J, 1989. 8(12): p. 3759-65.
60. Andrew, D., et al., *KIM185, a monoclonal antibody to CD18 which induces a change in the conformation of CD18 and promotes both LFA-1- and CR3-dependent adhesion.* Eur J Immunol, 1993. 23(9): p. 2217-22.
61. Stephens, P., et al., *KIM127, an antibody that promotes adhesion, maps to a region of CD18 that includes cysteine-rich repeats.* Cell adhesion and communication, 1995. 3(5): p. 375-84.
62. Orchekowski, R. P., et al., *AlphaMbeta2 (CD11b/CD18, Mac-1) integrin activation by a unique monoclonal antibody to alphaM I domain that is divalent cation-sensitive.* Journal of leukocyte biology, 2000. 68(5): p. 641-9.
63. Beals, C. R., et al., *CD18 activation epitopes induced by leukocyte activation.* J Immunol, 2001. 167(11): p. 6113-22.
64. Huth, J. R., et al., *NMR and mutagenesis evidence for an I domain allosteric site that regulates lymphocyte function-associated antigen 1 ligand binding.* Proc Natl Acad Sci USA, 2000. 97(10): p. 5231-6.
65. Zhang, H., et al., *Structural basis of activation-dependent binding of ligand-mimetic antibody AL-57 to integrin LFA-1.* Proc Natl Acad Sci USA, 2009. 106(43): p. 18345-50.
66. Ortlepp, S., et al., *Antibodies that activate beta 2 integrins can generate different ligand binding states.* Eur J Immunol, 1995. 25(3): p. 637-43.
67. Sanchez-Madrid, F., et al., *Mapping of antigenic and functional epitopes on the alpha- and beta-subunits of two related mouse glycoproteins involved in cell interactions, LFA-1 and Mac-1.* J Exp Med, 1983. 158(2): p. 586-602.
68. Sharfuddin, A. A. and B. A. Molitoris, *Pathophysiology of ischemic acute kidney injury.* Nat Rev Nephrol, 2011. 7(4): p. 189-200.
69. Varga, G., et al., *Active MAC-1 (CD11b/CD18) on DCs inhibits full T-cell activation.* Blood, 2007. 109(2): p. 661-9.
70. Draskovic-Pavlovic, B., et al., *Differential effects of anti-rat CD11b monoclonal antibodies on granulocyte adhesiveness.* Immunology, 1999. 96(1): p. 83-9.
71. Lefort, C. T., et al., *Outside-in signal transmission by conformational changes in integrin Mac-1.* J Immunol, 2009. 183(10): p. 6460-8.
72. Pluskota, E., et al., *Neutrophil apoptosis: selective regulation by different ligands of integrin alphaMbeta2.* J Immunol, 2008. 181(5): p. 3609-19.
73. Arnaout, M. A., et al., *Inhibition of phagocytosis of complement C3- or immunoglobulin G-coated particles and of C3bi binding by monoclonal antibodies to a monocyte-granulocyte membrane glycoprotein (Mol).* J Clin Invest, 1983. 72(1): p. 171-9.
74. Wright, S. D., et al., *Identification of the C3bi receptor of human monocytes and macrophages by using monoclonal antibodies.* Proc Natl Acad Sci USA, 1983. 80(18): p. 5699-703.
75. Hogg, N., et al., *A novel leukocyte adhesion deficiency caused by expressed but nonfunctional beta2 integrins Mac-1 and LFA-1.* J Clin Invest, 1999. 103(1): p. 97-106.
76. Damoiseaux, J. G., et al., *Heterogeneity of macrophages in the rat evidenced by variability in determinants: two new anti-rat macrophage antibodies against a heterodimer of 160 and 95 kd (CD11/CD18).* Journal of leukocyte biology, 1989. 46(6): p. 556-64.
77. Robinson, A. P., T. M. White, and D. W. Mason, *Macrophage heterogeneity in the rat as delineated by two monoclonal antibodies MRC OX-41 and MRC OX-42, the latter recognizing complement receptor type 3.* Immunology, 1986. 57(2): p. 239-47.
78. Springer, T., et al., *Mac-1: a macrophage differentiation antigen identified by monoclonal antibody.* Eur J Immunol, 1979. 9(4): p. 301-6.
79. Gupta, V., et al., *The beta-tail domain (betaTD) regulates physiologic ligand binding to integrin CD11b/CD18.* Blood, 2007. 109(8): p. 3513-20.
80. Szczur, K., Y. Zheng, and M. D. Filippi, *The small Rho GTPase Cdc42 regulates neutrophil polarity via CD11b integrin signaling.* Blood, 2009. 114(20): p. 4527-37.
81. Xiong, J. P., et al., *New insights into the structural basis of integrin activation.* Blood, 2003. 102(4): p. 1155-9.
82. Gabeler, E. E., et al., *A comparison of balloon injury models of endovascular lesions in rat arteries.* BMC Cardiovasc Disord, 2002. 2: p. 16.
83. Nishida, N., et al., *Activation of Leukocyte beta(2) Integrins by Conversion from Bent to Extended Conformations.* Immunity, 2006. 25(4): p. 583-94.
84. Altieri, D. C., *Occupancy of CD11b/CD18 (Mac-1) divalent ion binding site(s) induces leukocyte adhesion.* J Immunol, 1991. 147(6): p. 1891-8.
85. Dransfield, I., et al., *Divalent cation regulation of the function of the leukocyte integrin LFA-1.* J Cell Biol, 1992. 116(1): p. 219-26.
86. Xiong, J. P., et al., *An isoleucine-based allosteric switch controls affinity and shape shifting in integrin CD11b A-domain.* J Biol Chem, 2000. 275(49): p. 38762-7.
87. Weitz-Schmidt, G., et al., *Statins selectively inhibit leukocyte function antigen-1 by binding to a novel regulatory integrin site.* Nat Med, 2001. 7(6): p. 687-92.
88. Weitz-Schmidt, G., et al., *Improved lymphocyte function-associated antigen-1 (LFA-1) inhibition by statin derivatives: molecular basis determined by x-ray analysis and monitoring of LFA-1 conformational changes in vitro and ex vivo.* J Biol Chem, 2004. 279(45): p. 46764-71.
89. Yarrow, J. C., et al., *A high-throughput cell migration assay using scratch wound healing, a comparison of image-based readout methods.* BMC biotechnology, 2004. 4: p. 21.
90. Lampugnani, M. G., *Cell migration into a wounded area in vitro.* Methods in molecular biology (Clifton, N.J.), 1999. 96: p. 177-82.
91. Martin, P. and S. J. Leibovich, *Inflammatory cells during wound repair: the good, the bad and the ugly.* Trends in cell biology, 2005. 15(11): p. 599-607.
92. Lammeimann, T., et al., *Rapid leukocyte migration by integrin-independent flowing and squeezing.* Nature, 2008. 453(7191): p. 51-5.
93. Suen, P. W., et al., *Impaired integrin-mediated signal transduction, altered cytoskeletal structure and reduced motility in Hck/Fgr deficient macrophages.* Journal of cell science, 1999. 112 (Pt 22): p. 4067-78.
94. Alghisi, G. C., L. Ponsonnet, and C. Ruegg, *The integrin antagonist cilengitide activates alphaVbeta3, disrupts VE-cadherin localization at cell junctions and enhances permeability in endothelial cells.* PLoS One, 2009. 4(2): p. e4449.
95. Cox, D., *Oral GPIIb/IIIa antagonists: what went wrong?* Current pharmaceutical design, 2004. 10(14): p. 1587-96.

96. Peter, K., et al., *Induction of fibrinogen binding and platelet aggregation as a potential intrinsic property of various glycoprotein IIb/IIIa (alphaIIbbeta3) inhibitors.* Blood, 1998. 92(9): p. 3240-9.

97. Mahalingam, B., et al., *Stable Coordination of the Inhibitory Ca2+ Ion at the Metal Ion-Dependent Adhesion Site in Integrin CD11b/CD18 by an Antibody-Derived Ligand Aspartate: Implications for Integrin Regulation and Structure-Based Drug Design.* Journal of immunology, 2011. 187(12): p. 6393-401.

98. Zhu, J., et al., *Closed headpiece of integrin alphaIIb-beta3 and its complex with an alphaIIbbeta3-specific antagonist that does not induce opening.* Blood, 2010. 116(23): p. 5050-9.

99. Chew, D. P., et al., *Increased mortality with oral platelet glycoprotein antagonists: a mew-analysis of phase III multicenter randomized trials.* Circulation, 2001. 103(2): p. 201-6.

100. Gao, C., et al., *Eptifibatide-induced thrombocytopenia and thrombosis in humans require FcgammaRIIa and the integrin beta3 cytoplasmic domain.* The Journal of clinical investigation, 2009. 119(3): p. 504-11.

101. de Bruyn, K. M., et al., *The small GTPase Rap1 is required for Mn(2+)- and antibody-induced LFA-1- and VLA-4-mediated cell adhesion.* J Biol Chem, 2002. 277(33): p. 29468-76.

102. Walzog, B., et al., *A role for beta(2) integrins (CD11/CD18) in the regulation of cytokine gene expression of polymorphonuclear neutrophils during the inflammatory response.* The FASEB journal: official publication of the Federation of American Societies for Experimental Biology, 1999. 13(13): p. 1855-65.

103. Johnson, G. L. and R. Lapadat, *Mitogen-activated protein kinase pathways mediated by ERK, JNK, and p38 protein kinases.* Science, 2002. 298(5600): p. 1911-2.

104. Yu, H., et al., *Dissociation of mitogen-activated protein kinase activation from the oxidative burst in differentiated HL-60 cells and human neutrophils.* J Biol Chem, 1995. 270(26): p. 15719-24.

105. Semmrich, M., et al., *Importance of integrin LFA-1 deactivation for the generation of immune responses.* J Exp Med, 2005. 201(12): p. 1987-98.

106. Park, E. J., et al., *Aberrant activation of integrin alpha4beta7 suppresses lymphocyte migration to the gut.* J Clin Invest, 2007. 117(9): p. 2526-38.

107. Park, E. J., et al., *Distinct roles for LFA-1 affinity regulation during T-cell adhesion, diapedesis, and interstitial migration in lymph nodes.* Blood, 2010. 115(8): p. 1572-81.

108. Kim, M., C. V. Carman, and T. A. Springer, *Bidirectional transmembrane signaling by cytoplasmic domain separation in integrins.* Science, 2003. 301(5640): p. 1720-5.

109. Stroupe, K. T., et al., *Cost-effectiveness of coronary artery bypass grafts versus percutaneous coronary intervention for revascularization of high-risk patients.* Circulation, 2006. 114(12): p. 1251-7.

110. Ajani, A. E., et al., *Contemporary treatment of in-stent restenosis and the incidence of recurrent in-stent restenosis in the era of drug-eluting stents.* Heart Lung Circ, 2007. 16(4): p. 269-73.

111. Chen, M., et al., *Bare metal stent restenosis is not a benign clinical entity.* American heart journal, 2006. 151(6): p. 1260-1264.

112. Kaltoft, A., et al., *Long-term outcome after drug-eluting versus bare-metal stent implantation in patients with ST-segment elevation myocardial infarction: 3-year follow-up of the randomized DEDICATION (Drug Elution and Distal Protection in Acute Myocardial Infarction) Trial.* J Am Coll Cardiol, 2010. 56(8): p. 641-5.

113. Wang, Y., et al., *Leukocyte engagement of platelet glycoprotein Ibalpha via the integrin Mac-1 is critical for the biological response to vascular injury.* Circulation, 2005. 112(19): p. 2993-3000.

114. Wang, Y., et al., *Partial depletion of macrophages by ED7 reduces renal injury in Adriamycin nephropathy.* Nephrology (Carlton), 2005. 10(5): p. 470-7.

115. Palmen, M. J., et al., *Anti-CD11b/CD18 antibodies reduce inflammation in acute colitis in rats.* Clin Exp Immunol, 1995. 101(2): p. 351-6.

116. Palmen, M. J., et al., *Anti-CD11b/CD18 antibodies reduce inflammation in acute colitis in rats.* Clinical and experimental immunology, 1995. 101(2): p. 351-6.

117. Huitinga, I., et al., *Treatment with anti-CR3 antibodies ED7 and ED8 suppresses experimental allergic encephalomyelitis in Lewis rats.* European journal of immunology, 1993. 23(3): p. 709-15.

118. Cox, D., M. Brennan, and N. Moran, *Integrins as therapeutic targets: lessons and opportunities.* Nat Rev Drug Discov, 2010. 9(10): p. 804-20.

119. Quinn, M. J., E. F. Plow, and E. J. Topol, *Platelet glycoprotein IIb/IIIa inhibitors: recognition of a two-edged sword?* Circulation, 2002. 106(3): p. 379-85.

120. Lishko, V. K., et al., *Regulated unmasking of the cryptic binding site for integrin alpha M beta 2 in the gamma C-domain of fibrinogen.* Biochemistry, 2002. 41(43): p. 12942-51.

121. Flick, M. J., X. Du, and J. L. Degen, *Fibrin(ogen)-alpha M beta 2 interactions regulate leukocyte function and innate immunity in vivo.* Experimental biology and medicine, 2004. 229(11): p. 1105-10.

122. Flick, M. J., et al., *Leukocyte engagement of fibrin(ogen) via the integrin receptor alphaMbeta2/Mac-1 is critical for host inflammatory response in vivo.* J Clin Invest, 2004. 113(11): p. 1596-606.

123. Huitinga, I., et al., *Treatment with anti-CR3 antibodies ED7 and ED8 suppresses experimental allergic encephalomyelitis in Lewis rats.* Eur J Immunol, 1993. 23(3): p. 709-15.

124. Ahn, G. O., et al., *Inhibition of Mac-1 (CD11b/CD18) enhances tumor response to radiation by reducing myeloid cell recruitment.* Proc Natl Acad Sci USA, 2010. 107(18): p. 8363-8.

What is claimed is:

1. A method for treating diabetic nephropathy, the method comprising:

administering to a patient in need thereof an effective amount of a β2 integrin activating agent and improving the health of the patient's kidneys, wherein the β2 integrin activating agent is selected from the group consisting of:

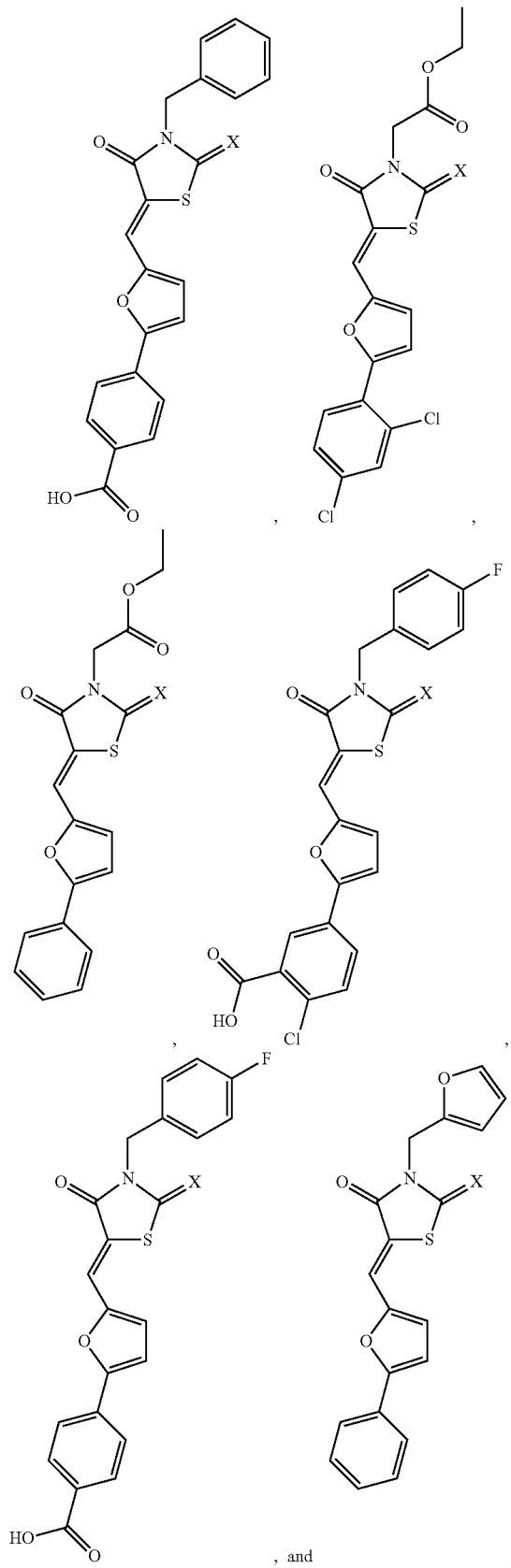
wherein X is selected from O and S,
and pharmaceutically acceptable salts thereof.
2. The method of claim 1, wherein the β2 integrin activating agent is selected from the group consisting of:
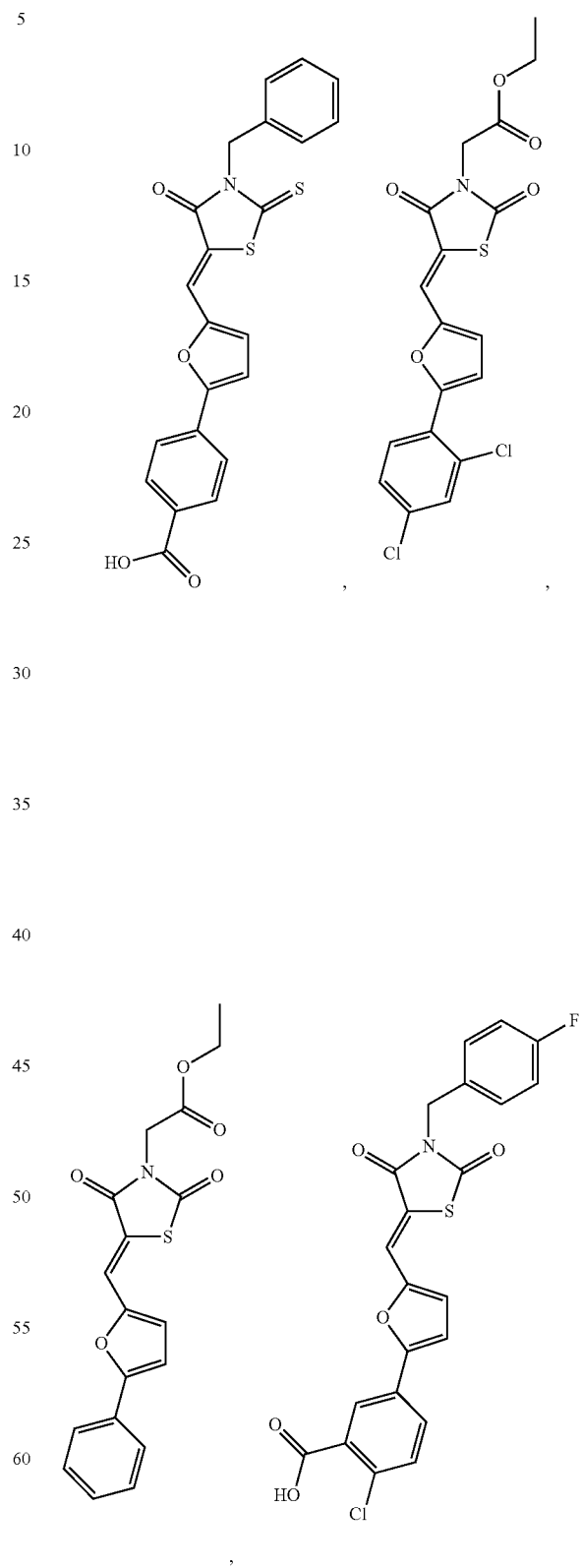

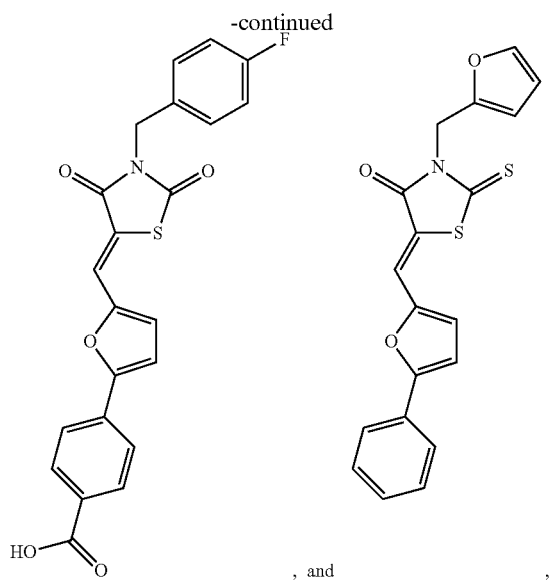
, and
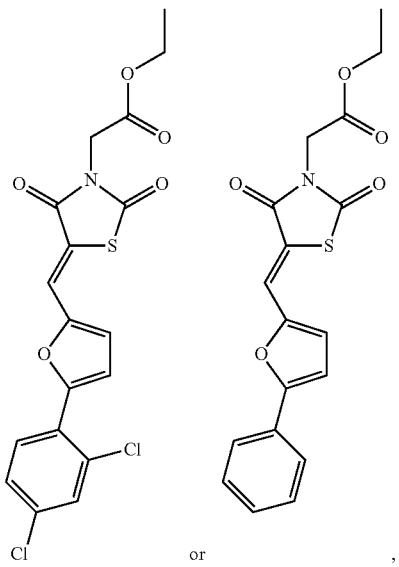
and pharmaceutically acceptable salts thereof.
3. The method of claim 1, wherein the β2 integrin activating agent is:
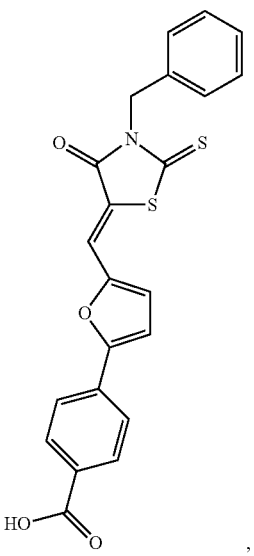 [SMILES: O=C(O)c1ccc(-c2ccc(/C=C3\SC(=S)N(Cc4ccccc4)C3=O)o2)cc1]
or a pharmaceutically acceptable salt thereof.
4. The method of claim 1, wherein the β2 integrin activating agent is:
or a pharmaceutically acceptable salt thereof.
5. The method of claim 1, wherein the β2 integrin activating agent is:
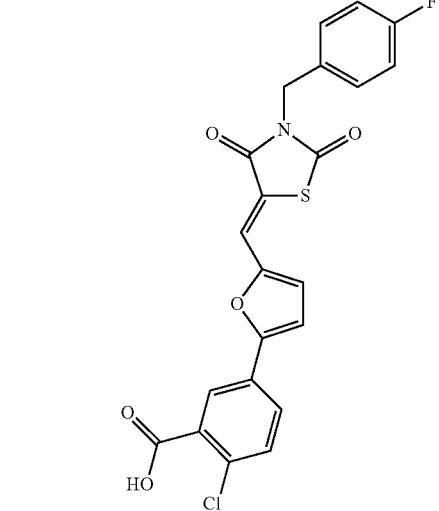
or

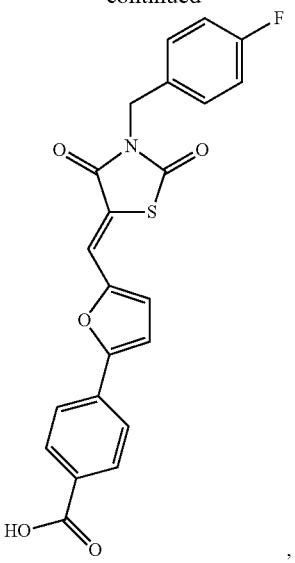
or a pharmaceutically acceptable salt thereof.
6. The method of claim 1, wherein the β2 integrin activating agent is:
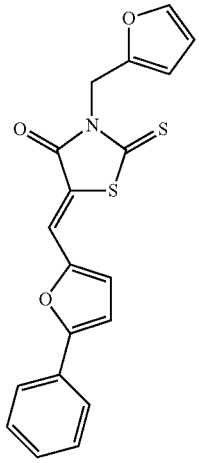
or a pharmaceutically acceptable salt thereof.
* * * * *